US008629283B2

(12) United States Patent
Shaw et al.

(10) Patent No.: US 8,629,283 B2
(45) Date of Patent: Jan. 14, 2014

(54) COMPOUNDS THAT MODULATE NEGATIVE-SENSE, SINGLE-STRANDED RNA VIRUS REPLICATION AND USES THEREOF

(75) Inventors: Megan L. Shaw, New York, NY (US); Hans-Heinrich Hoffmann, New York, NY (US); Adolfo Garcia-Sastre, New York, NY (US); Peter Palese, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 375 days.

(21) Appl. No.: 12/921,077

(22) PCT Filed: Mar. 6, 2009

(86) PCT No.: PCT/US2009/001474
§ 371 (c)(1),
(2), (4) Date: Dec. 13, 2010

(87) PCT Pub. No.: WO2009/136979
PCT Pub. Date: Nov. 12, 2009

(65) Prior Publication Data
US 2011/0105423 A1  May 5, 2011

Related U.S. Application Data

(60) Provisional application No. 61/034,459, filed on Mar. 6, 2008.

(51) Int. Cl.
*C07D 271/113* (2006.01)

(52) U.S. Cl.
CPC .................................. *C07D 271/113* (2013.01)
USPC ....................................................... 548/144

(58) Field of Classification Search
None
See application file for complete search history.

(56) References Cited

U.S. PATENT DOCUMENTS

| | | | |
|---|---|---|---|
| 6,384,064 | B2 | 5/2002 | Camden |
| 8,278,342 | B2 | 10/2012 | Ricciardi |
| 2005/0123902 | A1 | 6/2005 | Meneses et al. |
| 2005/0239906 | A1 | 10/2005 | Garaci et al. |
| 2009/0162831 | A1 | 6/2009 | Delwart et al. |
| 2010/0035887 | A1 | 2/2010 | Ricciardi |

FOREIGN PATENT DOCUMENTS

WO  WO 2011/150413 A1  12/2011

OTHER PUBLICATIONS

Hoffmann et al., "Broad-spectrum antiviral that interferes with de novo pyrimidine biosynthesis" PNAS (2011) vol. 108 No. 14 pp. 5777-5782.*
Rigaut et al., 1991, "Inhibition of VSV infection by staurosporine", J Cell Biol; 115(3Part2):476A.
Ciien et al., 2004, "Influenza A virus PB1-F2 gene in recent Taiwanese isolates", Emerging Infectious Diseases; 10(4):630-635.
Fabbri et al., 1994, "Export of protein from the endoplasmic reticulum is regulated by a diacylglycerol/phorbol ester binding protein", J Biol Chem; 269(43):26848-26857.
Gschwendt et al., 1994, "Rottlerin, a novel protein kinase inhibitor", Biochem Biophys Res Commun; 199(1):93-98.
Guggino et al., 2000, "Amiloride-sensitive sodium channels contribute to the woes of the flu", Proc Natl Acad Sci USA, 97(18):9827-9829.
Iioffmann et al., 2008, "Modulation of influenza virus replication by alteration of sodium ion transport and protein kinase C activity", Dept.of Microbiology, Mount Sinai School of Medicine, New York, NY 10029.
Hoffmann et al., 2008, "Modulation of influenza virus replication identified via a high-throughput screening approach", Dept.of Microbiology, Mount Sinai School of Medicine, New York, NY 10029.
International Search Report of International application No. PCT/US2009/001474, dated Jan. 18, 2010.
International Search Report of International application No. PCT/US2011/38515, dated Sep. 13, 2011.
Kistner et al., 1989, "Differential phosphorylation of the nucleoprotein of influenza A viruses", J Gen Virol; 70:2421-2431.
Kleyman et al., 1988, "Amiloride and its analogs as tools in the study of ion transport", J Membrane Biol; 105:1-21.
U.S. Appl. No. 13/700,049, filed Nov. 26, 2012, Shaw.
KunzelmAnn et al., 2000, "Influenza virus inhibits amiloride-sensitive $Na^+$ channels in respiratory epithelia", Proc Natl Acad Sci USA; 97(18):10282-10287.
Kurokawa et al., 1990, "Inhibitory effect of protein kinase C inhibitor on the replication of influenza type A virus", J Gen Virol; 71(Pt 9):2149-2155.
Lee ct al., 2007, "Crystal structure of the VP4 protcasc from infectious pancreatic necrosis virus reveals the acylenzyme complex for an intermolecular self-cleavage reaction", J Biol Chem; 282(34):24928-24937.
Link et al., 1966, "Interaction of heart glycosides and viruses", Acta Virol; 10:455-461.
Mahmoudian et al., 2009, "Influenza A virus proteins PB1 and NS1 are subject to functionally important phosphorylation by protein kinase C", J Gen Virol; 90(Pt 6):1392-1397.
Nagai et al., 1972, "Inhibition of virus growth by ouabain: effect of ouabain on the growth of HVJ in chick embryo cells", J Virol; 9(2):234-243.
Patterson et al., 1979, "Studies on the mechanism of influenza virus entry into cells", J Gen Virol; 43(223-229).
Root et al., 2000, "Entry of influenza viruses into cells is inhibited by a highly specific protein kinase C inhibitor", J Gen Virol; 81(Pt 11):2697-2705.

(Continued)

*Primary Examiner* — Eric S Olson
(74) *Attorney, Agent, or Firm* — Jones Day

(57) ABSTRACT

The present invention relates to compounds that modulate the replication of negative-sense, single-stranded RNA viruses, such as influenza virus, and the use of such compounds. The invention relates to methods for increasing the titer of negative-sense, single-stranded RNA viruses, such as influenza virus, in substrates for virus propagation (e.g., tissue culture). The invention also relates to the use of compounds that decrease virus replication as antiviral agents. The invention further relates to methods for identifying compounds that modulate the replication of negative-sense, single-stranded RNA viruses, in particular, influenza virus.

6 Claims, 13 Drawing Sheets

(56) References Cited

OTHER PUBLICATIONS

Figure 1:
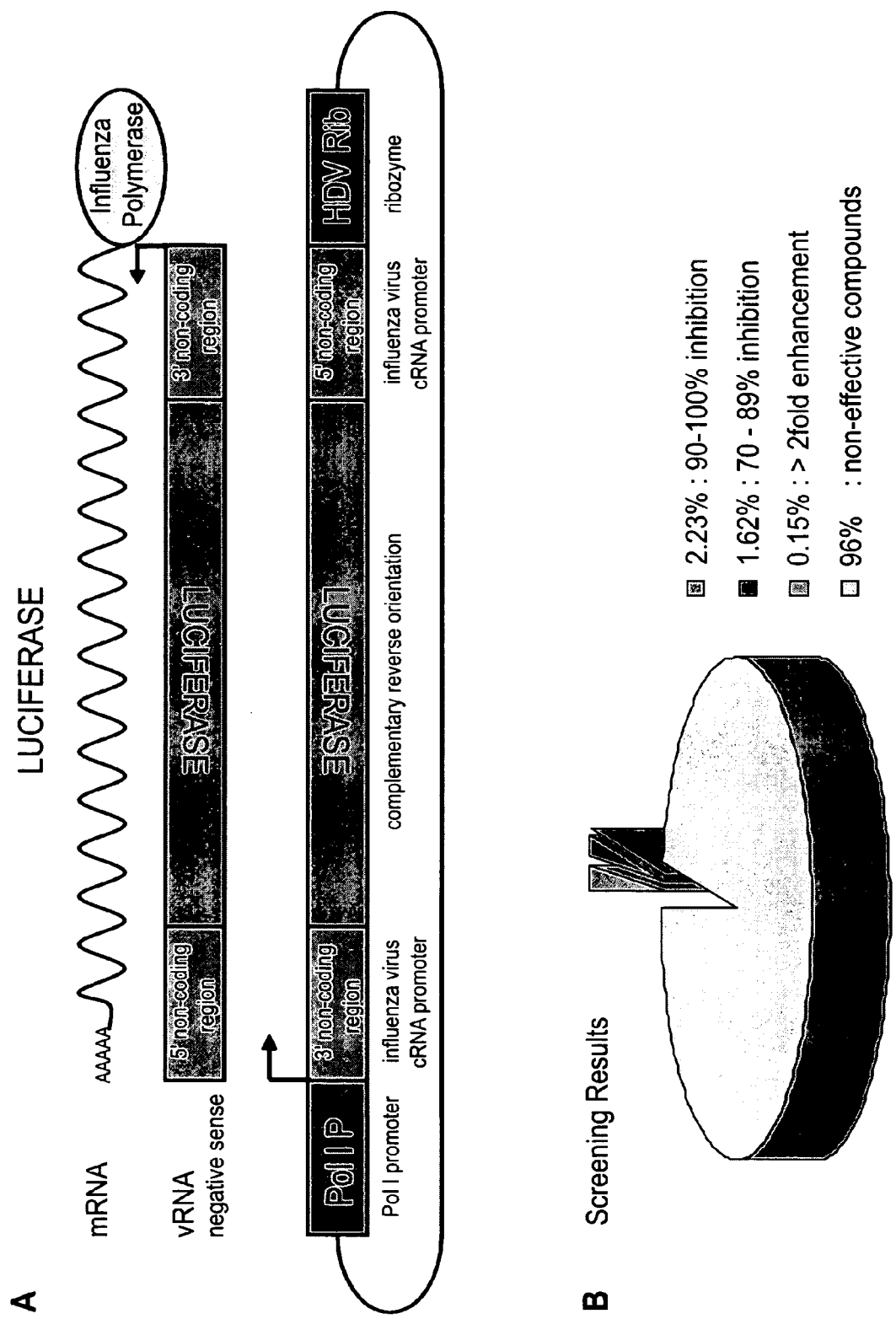

Salvatore et al., 2007, "α-defensin inhibits influenza virus replication by cell-mediated mechanism(s)", JID; 196:835-843.

Scholtissek et al., 1986, "Influence of insulin and 12-O-tetradecanoylphorbol-13-acetate (TPA) on influenza virus multiplication", Virus Res; 6:287-294.

Shaw et al., 2008, "Opposing effects on influenza growth by compounds targeting both sodium channels and protein kinase C", Dept. of Microbiology, Mount Sinai School of Medicine, New York, NY 10029 (Abstract only).

Sieczkarski et al., 2003, "Role of protein kinase C βII in influenza virus entry via late endosomes", J Virol; 77(1):460-469.

Wright et al., 2009, "Inhibition of simian virus 40 replication by targeting the molecular chaperone function and ATPase activity of T antigen", Virus Res; 141(1):71-80.

Written Opinion of International application No. PCT/US2009/001474, dated Jan. 18, 2010.

Written Opinion of International application No. PCT/US2011/38515, dated Sep. 13, 2011.

Yi et al., 2008, "A secondary gate as a mechanism for inhibition of the M2 proton channel by amantadine", J Phys Chem; 112(27):7977-7979.

\* cited by examiner

A  Enhancement of influenza A virus by Na$^+$-channel inhibitors

B  Enhancement of influenza A virus by PKC activators

Fig. 5

Fig. 7

A. Enhancement of influenza A/Wyoming/03/2003 virus
B. Enhancement of influenza A/Moscow/10/99 virus
C. Enhancement of the 6:2 reassortant virus H5N1/PR8 viral titer (log$_{10}$ PFU/mL)
hours post infection

— mezerein 250nM
— 2',4'-dichlorobenzamil 400nM
— untreated control (MOI=0.01) - A and B
— untreated control (MOI=0.001) - C

Enhancement of influenza A virus by amiloride derivatives

Fig. 8

A

B

COMPOUNDS THAT MODULATE NEGATIVE-SENSE, SINGLE-STRANDED RNA VIRUS REPLICATION AND USES THEREOF

This application is a national stage application of International Application No. PCT/US2009/001474, filed Mar. 6, 2009, which claims the benefit of U.S. Provisional Application No. 61/034,459, filed Mar. 6, 2008, each of which is incorporated herein by reference in its entirety.

This invention was made with government support under Grant Nos. AI057158, AI074539 and HHSN266200700010C awarded by the National Institutes of Health. The government has certain rights in the invention.

1. INTRODUCTION

The present invention relates to compounds that modulate the replication of negative-sense, single-stranded RNA viruses, such as influenza virus, and the use of such compounds. The invention relates to methods for increasing the titer of negative-sense, single-stranded RNA viruses, such as influenza virus, in substrates for virus propagation (e.g., tissue culture). The invention also relates to the use of compounds that decrease virus replication as antiviral agents. The invention further relates to methods for identifying compounds that modulate the replication of negative-sense, single-stranded RNA viruses, in particular, influenza virus.

2. BACKGROUND

Influenza viruses are enveloped RNA viruses that belong to the family of Orthomyxoviridae (Palese and Shaw, 2007). Influenza A and B viruses are considered to be major human pathogens and in a normal season they can cause between 3-5 million cases of severe illness and up to 500,000 deaths worldwide (World Health Organization, 2003). Influenza A viruses can also cause pandemics such as those that occurred in 1918, 1957 and 1968. These outbreaks resulted in high mortality rates because of the lack of pre-existing immunity against the new virus strain. Since the emergence of the highly pathogenic avian H5N1 influenza virus in the late 1990s (Claas et al., 1998), there have been concerns that it may be the next pandemic virus, which has sparked renewed interest in the development of anti-influenza virus drugs.

Currently there are only four U.S. Food and Drug Administration (FDA)-approved drugs available for the treatment and prevention of influenza. The adamantanes (amantadine and rimantadine) block the M2 ion channel of the virus and prevent the release of the viral genome into the host cell (Pinto and Lamb, 1995; Wharton et al., 1994). These drugs are effective if used prophylactically and if administered within 48 hours of infection but are not effective against influenza B viruses. However, the development of widespread resistance has precluded the use of adamantanes in recent influenza seasons (Bright et al., 2006) and isolates of the H5N1 influenza virus have been shown to be resistant to these drugs due to mutations in M2 (Cheung et al., 2006).

The preferred treatment for influenza virus infection is now the use of the neuraminidase inhibitors, oseltamivir and zanamivir (Garman and Layer, 2004). By targeting the neuraminidase, these compounds prevent the release of the virus from the infected cell and halt the spread of the virus. As part of its pandemic preparedness plan, the World Health Organization (WHO) has advised that supplies of the neuraminidase inhibitors be stockpiled, but it is always advantageous to have at least two antiviral drugs (aimed at different targets) available due to the possible emergence of resistant virus strains. In fact the 2007-2008 influenza season in the Northern hemisphere has shown a marked increase in the number of H1N1 isolates that are resistant to oseltamivir (World Health Organization, 2008) and concerns have also been raised regarding oseltamivir-resistant H5N1 influenza viruses isolated from patients in Southeast Asia (Le et al., 2005).

Vaccination is one means of preventing infection or at least minimizing the severity of disease. Based on knowledge of the current circulating influenza virus strains, the WHO makes an annual decision as to which virus strains should be included in the influenza vaccine for the following season. Manufacturers therefore have a relatively short time period in which to generate new vaccine stocks and this, combined with the increase in demand from the population, sometimes leads to shortages. Vaccine viruses are currently grown in embryonated chicken eggs which generally support high levels of virus growth; however the use of eggs has certain limitations. Vaccine production cannot easily be scaled up at short notice, as would be required during a pandemic, due to the reliance on a continuous supply of embryonated eggs. Furthermore, if the pandemic virus is of avian origin it may be lethal in eggs, as occurred during the preparation of an H5N1 vaccine candidate (Takada et al., 1999). An avian virus would likely also affect the poultry industry and the egg supply may dry up completely. In an effort to avoid these problems, vaccine manufacturers are now establishing tissue culture systems for the growth of influenza virus vaccines (Oxford et al., 2005; Romanova et al., 2004; Tree et al., 2001). The major disadvantage is that wild type human influenza virus strains often do not show optimal growth properties in this culture system, resulting in lower vaccine yields.

Thus, there is an urgent need for the development of new antiviral drugs and also for the improvement of tissue culture-based vaccine production, in preparation for future influenza epidemics or pandemics.

3. SUMMARY

The present invention relates to compounds that modulate the replication of negative-sense, single-stranded RNA viruses, methods for identifying such compounds, and the use of such compounds. Compounds that enhance the replication of a negative-sense, single-stranded RNA virus have utility in the propagation of the virus. In particular, compounds that enhance the replication of a negative-sense, single-stranded RNA virus (e.g., an attenuated negative-sense, single-stranded RNA virus) have utility in the manufacture of vaccines. Compounds that reduce the replication of a negative-sense, single-stranded RNA virus have utility as antivirals.

The present invention is based, in part, on Applicants' discovery that a sodium channel opener, an inhibitor of a sodium/potassium/ATPase pump ("$Na^+/K^+$/ATPase pump") and a PKC inhibitor each reduce the replication of influenza virus, a negative-sense, single-stranded RNA virus. The present invention is also based, in part, on Applicants' discovery that sodium channel inhibitors, calcium channel inhibitors and protein kinase C (PKC) activators enhance the replication of an influenza virus, a negative-sense, single-stranded RNA virus.

The present invention provides methods for inhibiting or reducing the replication of a negative-sense, single-stranded RNA virus, comprising contacting a cell infected with a negative-sense, single-stranded RNA virus with an inhibitor of virus replication in an amount sufficient to inhibit or reduce the replication of the virus. In one embodiment, a method for inhibiting or reducing the replication of a negative-sense, single-stranded RNA virus comprises: (a) infecting a cell with a negative-sense, single-stranded RNA virus; and (b) contacting the cell with an inhibitor of virus replication in an amount sufficient to inhibit or reduce replication of the virus. The present invention also provides methods for inhibiting or reducing negative-sense, single-stranded RNA virus replication, comprising: (a) contacting a cell with an inhibitor of virus replication in an amount sufficient to inhibit or reduce replication of a negative-sense, single-stranded RNA virus; and (b) infecting the cell with the negative-sense, single-stranded RNA virus. In certain embodiments, the inhibitor is a PKC inhibitor. In certain embodiments, the PKC inhibitor is rottlerin. In certain embodiments, the PKC inhibitor is not bisindolylmaleimide I, 1-(5-inoquinolinesulphonyl)-2-methylpiperazine dihydrochloride (H7), staurosporine, calphostin C or Gö6976. In certain embodiments, the inhibitor is a sodium channel opener. In certain embodiments, the sodium channel opener is SDZ-201106. In certain embodiments, the inhibitor is a $Na^+/K^+$/ATPase pump inhibitor. In certain embodiments, the $Na^+/K^+$/ATPase pump inhibitor is ouabain, lanatoside C, digoxin or strophanthidin. In yet other embodiments, the inhibitor is a calcium channel opener, such as K8644 (±) or FPL-64176. In yet other embodiments, the inhibitor is a compound of formula A3-G (see Section 5.1.1 below), including, but not limited to, 2-(5-(2,3-dimethyl-1H-indol-5-yl)-1,3,4-oxadiazol-2-ylthio)-1-(pyrrolidin-1-yl)ethanone ("A3"); 2-(5-(2,3-dimethyl-1H-indol-5-yl)-1,3,4-oxadiazol-2-ylthio)-N,N-diethylacetamide ("A3-2"); 2-(5-(2,3-dimethyl-1H-indol-5-yl)-1,3,4-oxadiazol-2-ylthio)-1-(indolin-1-yl)ethanone ("A3-3"); 2-(5-(2,3-dimethyl-1H-indol-5-yl)-1,3,4-oxadiazol-2-ylthio)-N,N-diisopropylacetamide ("A3-4"); 2-(5-(2,3-dimethyl-1H-indol-5-yl)-1,3,4-oxadiazol-2-ylthio)-1-morpholinoethanone ("A3-5"); or 1-(azepan-1-yl)-2-(5-(2,3-dimethyl-1H-indol-5-yl)-1,3,4-oxadiazol-2-ylthio)ethanone ("A3-6"). In certain specific embodiments, the inhibitor is a compound with the formula A3. In other embodiments, the inhibitor is a compound with the formula A3-2, A3-3, A3-4, A3-5 or A3-6. In other embodiments, the inhibitor is 4-(4-bromophenyl)-N-methyl-N-(tetrahydro-1,1-dioxido-3-thienyl)-2-thiazolamine ("A35"); N-methyl-4-(4-nitrophenyl)-N-(phenylmethyl)-2-thiazolamine ("A35-1"); 4-[[4-(4-chlorophenyl)-1,3-thiazol-2-yl](methyl)amino]phenol ("A35-4"); or 4-(4-chlorophenyl)-N,N-dimethylthiazol-2-amine ("A35-5"). In certain specific embodiments, the inhibitor is a compound with the formula A35. In yet other embodiments, the inhibitor is 9-(benzo[d][1,3]dioxol-5-yl)-4-hydroxy-6,7-dimethoxynaphtho[2,3-c]furan-1(3H)-one ("C2"). In certain embodiments, the negative-sense, single-stranded RNA virus is an influenza virus. In certain embodiments, the negative-sense, single-stranded RNA virus is Newcastle Disease Virus (NDV). In certain embodiments, the negative-sense, single-stranded RNA virus is vesicular stomatitis virus (VSV).

In one embodiment, the present invention provides a method of inhibiting replication of a negative-sense, single-stranded RNA virus, comprising contacting a first composition comprising a cell(s) and a PKC inhibitor with a second composition comprising a negative-sense, single-stranded RNA virus. In another embodiment, the invention provides a method of inhibiting replication of a negative-sense, single-stranded RNA virus, comprising contacting a first composition comprising a cell(s) infected with a negative-sense, single-stranded RNA virus with a second composition comprising a PKC inhibitor. In certain embodiments, the PKC inhibitor is rottlerin. In certain embodiments, the PKC inhibitor is not bisindolylmaleimide I, 1-(5-inoquinolinesulphonyl)-2-methylpiperazine dihydrochloride (H7), staurosporine, calphostin C or Gö6976.

In one embodiment, the present invention provides a method of inhibiting replication of a negative-sense, single-stranded RNA virus, comprising contacting a first composition comprising a cell(s) and a $Na^+/K^+$/ATPase pump inhibitor with a second composition comprising a negative-sense, single-stranded RNA virus. In another embodiment, the invention provides a method of inhibiting replication of a negative-sense, single-stranded RNA virus, comprising contacting a first composition comprising a cell(s) infected with a negative-sense, single-stranded RNA virus with a second composition comprising a $Na^+/K^+$/ATPase pump inhibitor. In certain embodiments, the $Na^+/K^+$/ATPase pump inhibitor is ouabain, lanatoside C, digoxin or strophanthidin.

In one embodiment, the present invention provides a method of inhibiting replication of a negative-sense, single-stranded RNA virus, comprising contacting a first composition comprising a cell(s) and a sodium channel opener with a second composition comprising a negative-sense, single-stranded RNA virus. In another embodiment, the invention provides a method of inhibiting replication of a negative-sense, single-stranded RNA virus, comprising contacting a first composition comprising a cell(s) infected with a negative-sense, single-stranded RNA virus with a second composition comprising a sodium channel opener. In certain embodiments, the sodium channel opener is SDZ-201106.

In one embodiment, the present invention provides a method of inhibiting replication of a negative-sense, single-stranded RNA virus, comprising contacting a first composition comprising a cell(s) and a calcium channel opener with a second composition comprising a negative-sense, single-stranded RNA virus. In another embodiment, the invention provides a method of inhibiting replication of a negative-sense, single-stranded RNA virus, comprising contacting a first composition comprising a cell(s) infected with a negative-sense, single-stranded RNA virus with a second composition comprising a calcium channel opener. In certain embodiments, the calcium channel opener is K8644 (±) or FPL-64176.

In one embodiment, the present invention provides a method of inhibiting replication of a negative-sense, single-stranded RNA virus, comprising contacting a first composition comprising a cell(s) and one of the following compounds: a compound of the formula A3-G, including a compound with the formula A3, A3-2, A3-3, A3-4, A3-5 or A3-6; a compound with the formula A35, A35-1, A35-4, or A35-5; or a compound with the formula C2 with a second composition comprising a negative-sense, single-stranded RNA virus. In another embodiment, the invention provides a method of inhibiting replication of a negative-sense, single-stranded RNA virus, comprising contacting a first composition comprising a cell(s) infected with a negative-sense, single-stranded RNA virus with a second composition comprising one of the following compounds: a compound with the formula A3-G, including a compound with the formula A3, A3-2, A3-3, A3-4, A3-5 or A3-6; a compound with the formula A35, A35-1, A35-4, A35-5; or a compound with the formula C2. In certain embodiments, the inhibitor is not a compound with the formula C2. In certain embodiments, the negative-sense, single-stranded RNA virus is an influenza virus.

In one embodiment, the invention provides a method of inhibiting replication of a negative-sense, single-stranded RNA virus in a subject, comprising administering to a subject in need thereof an effective amount of a PKC inhibitor. In certain embodiments, the PKC inhibitor is not bisindolylmaleimide I, 1-(5-inoquinolinesulphonyl)-2-methylpiperazine dihydrochloride (H7), staurosporine, calphostin C or Gö6976. In another embodiment, the invention provides a method of inhibiting replication of a negative-sense, single-stranded RNA virus in a subject, comprising administering to a subject in need thereof an effective amount of a sodium channel opener. In another embodiment, the invention provides a method of inhibiting replication of a negative-sense, single-stranded RNA virus in a subject, comprising administering to a subject in need thereof an effective amount of a Na+/K+/ATPase pump inhibitor. In another embodiment, the invention provides a method of inhibiting replication of a negative-sense, single-stranded RNA virus in a subject, comprising administering to a subject in need thereof an effective amount of a calcium channel opener. In some embodiments, the subject is a human. In some embodiments, the negative-sense, single-stranded RNA virus is influenza virus. In specific embodiments, the negative-sense, single-stranded RNA virus is vesicular stomatitis virus (VSV) or Newcastle disease virus (NDV).

In some embodiments, the invention provides methods of inhibiting replication of a negative-sense, single-stranded RNA virus in a subject, comprising administering to a subject in need thereof an effective amount of rottlerin, ouabain, lanatoside C, digoxin, strophanthidin or SDZ-201106. In other embodiments, the invention provides methods of inhibiting replication of a negative-sense, single-stranded RNA virus in a subject, comprising administering to a subject in need thereof an effective amount of K8644 (±) or FPL-64176. In specific embodiments, the subject is a human.

In certain embodiments, the invention provides methods of inhibiting replication of a negative-sense, single-stranded RNA virus in a subject, comprising administering to a subject in need thereof an effective amount of rottlerin, ouabain, lanatoside C, digoxin, strophanthidin or SDZ-201106. In other embodiments, the invention provides methods of inhibiting replication of a negative-sense, single-stranded RNA virus in a subject, comprising administering to a subject in need thereof an effective amount of K8644 (±) or FPL-64176. In other embodiments, the invention provides methods of inhibiting replication of a negative-sense, single-stranded RNA virus in a subject, comprising administering to a subject in need thereof an effective amount of one of the following compounds: a compound with the formula A3-G, such as a compound with the formula A3, A3-2, A3-3, A3-4, A3-5, or A3-6; a compound with the formula A35, A35-1, A35-4, A35-5; or a compound with the formula C2. In certain embodiments, the inhibitor is not a compound with the formula C2. In certain embodiments, the negative-sense, single-stranded RNA virus is an influenza virus. In specific embodiments, the subject is a human.

The present invention provides methods for preventing, treating and/or managing a negative-sense, single-stranded RNA virus infection in a subject, comprising administering to a subject in need thereof an effective amount of an inhibitor of virus replication. The present invention also provides methods for preventing, treating and/or managing a negative-sense, single-stranded RNA virus infection in a subject, comprising administering to a subject in need thereof an effective amount of an inhibitor of virus replication and one or more other therapies. In certain embodiments, the inhibitor is a sodium channel opener, such as SDZ-201106. In other embodiments, the inhibitor is a sodium/potassium/ATPase pump inhibitor, such as ouabain, lanatoside C, and digoxin. In other embodiments, the inhibitor is a calcium channel opener, such as K8644 (±) or FPL-64176. In other embodiments, the inhibitor is one of the following compounds: a compound with the formula A3-G, such as a compound with the formula A3, A3-2, A3-3, A3-4, A3-5, or A3-6. In certain specific embodiments, the inhibitor is a compound with the formula A3. In other embodiments, the inhibitor is a compound with the formula A3-2, A3-3, A3-4, A3-5, or A3-6. In other embodiments, the inhibitor is a compound with the formula A35, A35-1, A35-4, or A35-5. In specific embodiments, the inhibitor is a compound with the formula A35. In other embodiments, the inhibitor is a compound with the formula C2. In certain other embodiments, the inhibitor is not a compound with the formula C2.

In certain embodiments, the invention provides a method of preventing, treating and/or managing a negative-sense, single-stranded RNA virus infection in a subject, comprising administering to a subject in need thereof an effective amount of a protein kinase C (PKC) inhibitor. In certain embodiments, the PKC inhibitor is not bisindolylmaleimide I, 1-(5-inoquinolinesulphonyl)-2-methylpiperazine dihydrochloride (H7), staurosporine, calphostin C or Gö6976. In certain embodiments, the invention provides a method of preventing, treating and/or managing a negative-sense, single-stranded RNA virus infection in a subject, comprising administering to a subject in need thereof an effective amount of a sodium channel opener. In certain embodiments, the invention provides a method of preventing, treating and/or managing a negative-sense, single-stranded RNA virus infection in a subject, comprising administering to a subject in need thereof an effective amount of a calcium channel opener. In certain embodiments, the invention provides a method of preventing, treating and/or managing a negative-sense, single-stranded RNA virus infection in a subject, comprising administering to a subject in need thereof an effective amount of a Na+/K+/ATPase pump inhibitor. In certain embodiments, the subject is a human. In certain embodiments, the negative-sense, single-stranded RNA virus is influenza virus. In certain embodiments, the negative-sense, single-stranded RNA virus is VSV or NDV.

In certain embodiments, the invention provides a method of preventing, treating and/or managing a negative-sense, single-stranded RNA virus infection in a subject, comprising administering to a subject in need thereof an effective amount of a compound with the formula A3-G, including, but not limited to, 2-(5-(2,3-dimethyl-1H-indol-5-yl)-1,3,4-oxadiazol-2-ylthio)-1-(pyrrolidin-1-yl)ethanone ("A3"); 2-(5-(2,3-dimethyl-1H-indol-5-yl)-1,3,4-oxadiazol-2-ylthio)-N,N-diethylacetamide ("A3-2"); 2-(5-(2,3-dimethyl-1H-indol-5-yl)-1,3,4-oxadiazol-2-ylthio)-1-(indolin-1-yl)ethanone ("A3-3"); 2-(5-(2,3-dimethyl-1H-indol-5-yl)-1,3,4-oxadiazol-2-ylthio)-N,N-diisopropylacetamide ("A3-4"); 2-(5-(2,3-dimethyl-1H-indol-5-yl)-1,3,4-oxadiazol-2-ylthio)-1-morpholinoethanone ("A3-5"); or 1-(azepan-1-yl)-2-(5-(2,3-dimethyl-1H-indol-5-yl)-1,3,4-oxadiazol-2-ylthio)ethanone ("A3-6"). In certain embodiments, the inhibitor is a compound with the formula A3. In other embodiments, the inhibitor is a compound with the formula A3-2, A3-3, A3-4, A3-5, or A3-6.

In certain embodiments, the invention provides a method of preventing, treating and/or managing a negative-sense, single-stranded RNA virus infection in a subject, comprising administering to a subject in need thereof an effective amount of 4-(4-bromophenyl)-N-methyl-N-(tetrahydro-1,1-dioxido-3-thienyl)-2-thiazolamine ("A35"); N-methyl-4-(4-nitrophenyl)-N-(phenylmethyl)-2-thiazolamine ("A35-1"); 4-[[4-(4-chlorophenyl)-1,3-thiazol-2-yl](methyl)amino]phenol ("A35-4"); or 4-(4-chlorophenyl)-N,N-dimethylthiazol-2- amine ("A35-5"). In certain specific embodiments, the inhibitor is a compound with the formula A35.

In certain embodiments, the invention provides a method of preventing, treating and/or managing a negative-sense, single-stranded RNA virus infection in a subject, comprising administering to a subject in need thereof an effective amount of 9-(benzo[d][1,3]dioxol-5-yl)-4-hydroxy-6,7-dimethoxynaphtho[2,3-c]furan-1(3H)-one ("C2"). In certain embodiments, the inhibitor of the invention is not a compound with the formula C2.

In certain of the above embodiments, the negative-sense, single-stranded RNA virus is influenza virus. In certain embodiments, the negative-sense, single-stranded RNA virus is VSV or NDV. In certain embodiments, the negative-sense, single-stranded RNA virus is not VSV.

In certain embodiments, the invention provides a method of preventing, treating and/or managing a negative-sense, single-stranded RNA virus infection in a subject, comprising administering to a subject in need thereof an effective amount of rottlerin, ouabain, lanatoside C, digoxin, strophanthidin or SDZ-201106. In other embodiments, the invention provides methods of preventing, treating and/or managing a negative-sense, single-stranded RNA virus in a subject, comprising administering to a subject in need thereof an effective amount of K8644 (±) or FPL-64176. In certain embodiments, the subject is a human. In certain embodiments, the negative-sense, single-stranded RNA virus is influenza virus.

The present invention provides methods for enhancing the replication of a negative-sense, single-stranded RNA virus in a substrate for propagating virus, comprising contacting a substrate infected with a negative-sense, single-stranded RNA virus with an enhancer of virus replication. In one embodiment, the invention provides a method for enhancing replication of a negative-sense, single-stranded RNA virus in a substrate, comprising contacting a PKC activator with a substrate infected with a negative-sense, single-stranded RNA virus, wherein the substrate permits replication of the negative-sense, single-stranded RNA virus. In certain embodiments, the PKC activator is phorbol 12-myristate 13-acetate (PMA) or mezerein. In one embodiment, the invention provides a method for enhancing replication of a negative-sense, single-stranded RNA virus in a substrate, comprising contacting a sodium channel inhibitor with a substrate infected with a negative-sense, single-stranded RNA virus, wherein the substrate permits replication of the negative-sense, single-stranded RNA virus. In certain embodiments, the sodium channel inhibitor is phenamil, 2',4'-dichlorobenzamil or 3',4'-dichlorobenzamil. In one embodiment, the invention provides a method for enhancing replication of a negative-sense, single-stranded RNA virus in a substrate, comprising contacting a calcium channel inhibitor with a substrate infected with a negative-sense, single-stranded RNA virus, wherein the substrate permits replication of the negative-sense, single-stranded RNA virus. In certain embodiments, the calcium channel inhibitor is Amiloride-.HCl or 2',4'-Dichlorobenzamil.HCl. In certain embodiments, the substrate is a cell or cell line, such as, for example, an avian cell, chicken cell, Vero cell, MDCK cell, human respiratory epithelial cell (e.g., A549 cells), calf kidney cell or mink lung cell. In certain embodiments, the substrate is an embryonated egg. In certain embodiments, the negative-sense, single-stranded RNA virus is influenza virus. In other embodiments, the negative-sense, single-stranded RNA virus is VSV or NDV.

The present invention also provides methods for enhancing the replication of a negative-sense, single-stranded RNA virus in a substrate for propagating virus, comprising: (i) contacting a substrate that permits replication of the negative-sense, single-stranded RNA virus with an enhancer of virus replication; and (ii) infecting the substrate with the negative-sense, single-stranded RNA virus. In one embodiment, the invention provides a method for enhancing replication of a negative-sense, single-stranded RNA virus in a substrate, comprising: (i) contacting a substrate that permits replication of the negative-sense, single-stranded RNA virus with a PKC activator; and (ii) infecting the substrate with the negative-sense, single-stranded RNA virus. In certain embodiments, the PKC activator is phorbol 12-myristate 13-acetate (PMA) or mezerein. In one embodiment, the invention provides a method for enhancing replication of a negative-sense, single-stranded RNA virus in a substrate, comprising: (i) contacting a substrate that permits replication of the negative-sense, single-stranded RNA virus with a sodium channel inhibitor; and (ii) infecting the substrate with the negative-sense, single-stranded RNA virus. In certain embodiments, the sodium channel inhibitor is phenamil, 2',4'-dichlorobenzamil or 3',4'-dichlorobenzamil. In one embodiment, the invention provides a method for enhancing replication of a negative-sense, single-stranded RNA virus in a substrate, comprising: (i) contacting a substrate that permits replication of the negative-sense, single-stranded RNA virus with a calcium channel inhibitor; and (ii) infecting the substrate with the negative-sense, single-stranded RNA virus. In certain embodiments, the calcium channel inhibitor is Amiloride.HCl or 2',4'-Dichlorobenzamil.HCl. In certain embodiments, the substrate is a cell or cell line, such as, for example, an avian cell, chicken cell, Vero cell, MDCK cell, human respiratory epithelial cell (e.g., A549 cells), calf kidney cell or mink lung cell. In certain embodiments, the substrate is an embryonated egg. In certain embodiments, the negative-sense, single-stranded RNA virus is influenza virus. In other embodiments, the negative-sense, single-stranded RNA virus is VSV or NDV.

The present invention provides methods for enhancing the production of a negative-sense, single-stranded RNA virus for use in a vaccine formulation comprising contacting a substrate infected with a negative-sense, single-stranded RNA virus with an enhancer of virus replication. The present invention also provides a method for enhancing the production of a negative-sense, single-stranded RNA virus for use in a vaccine formulation, comprising contacting a substrate that permits replication of a negative-sense, single-stranded RNA virus with an enhancer of virus replication, and infecting the substrate with the negative-sense, single-stranded RNA virus. In a specific embodiment, the invention provides a method for enhancing the production of an influenza virus for use in a vaccine formulation, comprising contacting an enhancer of virus replication with a substrate infected with the virus. In another embodiment, the invention provides a method for enhancing the production of an influenza virus for use in a vaccine formulation, comprising contacting an enhancer of virus replication with a substrate that permits replication of the virus, and infecting the substrate with the virus.

The present invention provides methods for the manufacture of a negative-sense, single-stranded RNA virus vaccine, comprising contacting an enhancer of viral replication with a substrate infected with the virus under conditions that permit the replication of the virus, and purifying the virus. The present invention also provides methods for the manufacture of a negative-sense, single-stranded RNA virus vaccine, comprising contacting an enhancer of virus replication with a substrate that permits the replication of the virus, infecting the substrate with the virus, and purifying the virus.

In one embodiment, the invention provides a method for manufacture of a negative-sense, single-stranded RNA virus vaccine, comprising: (i) contacting a PKC activator with a substrate infected with a negative-sense, single-stranded RNA virus under conditions that permit the negative-sense, single-stranded RNA virus to replicate; and (ii) purifying the negative-sense, single-stranded RNA virus. In another embodiment, the invention provides a method for manufacture of a negative-sense, single-stranded RNA virus vaccine, comprising: (i) contacting a sodium channel inhibitor with a substrate infected with a negative-sense, single-stranded RNA virus under conditions that permit the negative-sense, single-stranded RNA virus to replicate; and (ii) purifying the negative-sense, single-stranded RNA virus. In another embodiment, the invention provides a method for manufacture of a negative-sense, single-stranded RNA virus vaccine, comprising: (i) contacting a calcium channel inhibitor with a substrate infected with a negative-sense, single-stranded RNA virus under conditions that permit the negative-sense, single-stranded RNA virus to replicate; and (ii) purifying the negative-sense, single-stranded RNA virus. In certain embodiments, the negative-sense, single-stranded RNA virus is influenza, NDV or VSV.

In another embodiment, the invention provides a method for manufacture of a negative-sense, single-stranded RNA virus vaccine, comprising: (i) contacting a PKC activator with a substrate that permits replication of the negative-sense, single-stranded RNA virus; (ii) infecting the substrate with the negative-sense, single-stranded RNA virus; and (iii) purifying the negative-sense, single-stranded RNA virus. In another embodiment, the invention provides a method for manufacture of a negative-sense, single-stranded RNA virus vaccine, comprising: (i) contacting a sodium channel inhibitor with a substrate that permits replication of the negative-sense, single-stranded RNA virus; (ii) infecting the substrate with the negative-sense, single-stranded RNA virus; and (iii) purifying the negative-sense, single-stranded RNA virus. In another embodiment, the invention provides a method for manufacture of a negative-sense, single-stranded RNA virus vaccine, comprising: (i) contacting a calcium channel inhibitor with a substrate that permits replication of the negative-sense, single-stranded RNA virus; (ii) infecting the substrate with the negative-sense, single-stranded RNA virus; and (iii) purifying the negative-sense, single-stranded RNA virus. In certain embodiments of the invention, the negative-sense, single-stranded RNA virus is influenza virus, VSV or NDV. In another embodiment, the invention provides a method for manufacture of an influenza virus vaccine, comprising: (i) contacting PMA, mezerein, phenamil, 2',4'-dichlorobenzamil or 3',4'-dichlorobenzamil with a substrate infected with an influenza virus under conditions that permit the influenza virus to replicate; and (ii) purifying the influenza virus. In another embodiment, the invention provides a method for manufacture of an influenza virus vaccine, comprising: (i) contacting PMA, mezerein, phenamil, 2',4'-dichlorobenzamil or 3',4'-dichlorobenzamil with a substrate that permits replication of influenza virus; (ii) infecting the substrate with the influenza virus; and (iii) purifying the influenza virus. In certain embodiments, the methods of manufacture contemplated for use in the invention further comprise inactivating the virus. In certain embodiments, the virus for use in the invention is attenuated.

In another embodiment, the invention provides a method for the manufacture of a negative-sense, single-stranded RNA virus vaccine, comprising: (a) contacting an enhancer of virus replication with a substrate infected with an attenuated negative-sense, single-stranded RNA virus; and (b) purifying the virus from the substrate. In another embodiment, the invention provides a method for the manufacture of an inactivated negative-sense, single-stranded RNA virus, comprising: (a) contacting an enhancer of virus replication with a substrate infected with a negative-sense, single-stranded RNA virus; (b) purifying the virus from the substrate; and (c) inactivating the virus. In certain embodiments, the enhancer is a sodium channel inhibitor, such as phenamil or 2',4'-dichlorobenzamil. In other embodiments, the enhancer is a PKC activator, such as PMA or mezerein. In other embodiments, the enhancer is a calcium channel inhibitor. In certain embodiments, the calcium channel inhibitor is Amiloride.HCl or 2',4'-Dichlorobenzamil.HCl.

Any type, subtype, and strain of a negative-sense, single-stranded RNA virus may be used in accordance with the invention. In certain embodiments, the negative-sense, single-stranded RNA virus is a non-segmented virus. In other embodiments, the negative-sense, single-stranded RNA virus is a segmented virus. In a specific embodiment, the negative-sense, single-stranded RNA virus is an enveloped virus. In another specific embodiment, the negative-sense, single-stranded RNA virus is influenza virus (e.g., an influenza A virus, influenza B virus or influenza C virus). In another embodiment, the negative-sense, single-stranded RNA virus is a parainfluenza virus, a measles virus, a mumps virus or a respiratory syncytial virus (RSV). In certain embodiments, the negative-sense, single-stranded RNA virus is not a Sendai virus. In some embodiments, the negative-sense, single-stranded RNA virus is attenuated.

The present invention also provides high throughput screening assays for the identification of compounds that modulate the replication of negative-sense, single-stranded RNA viruses. In one embodiment, the invention provides a method for identifying a compound that modulates the replication of a negative-sense, single-stranded RNA virus comprising: (i) contacting a compound or a member of a library of compounds with a cell transfected with a mini-genome reporter construct, wherein the mini-genome reporter construct comprises a reporter gene flanked by the 3' and 5' signals which are required for proper transcription by RNA polymerase I and recognition and transcription by the negative-sense, single-stranded RNA virus polymerase; (ii) infecting the cell with the negative-sense, single-stranded RNA virus in the presence of the compound; and (iii) measuring the expression or activity of a gene product encoded by the reporter gene, wherein a compound that modulates replication of the negative-sense, single-stranded RNA virus is identified if the expression or activity of the reporter gene product is altered in the presence of the compound or member of a library of compounds compared to expression or activity of the reporter gene product in the absence of the compound or member of a library of compounds or a negative control. In another embodiment, the invention provides a method for identifying a compound that modulates the replication of a negative-sense, single-stranded RNA virus comprising: (i) infecting a cell with a negative-sense, single-stranded RNA virus in the presence of a compound or a member of a library of compounds, wherein the cell is transfected with a mini-genome reporter construct, wherein the mini-genome reporter construct comprises a reporter gene flanked by the 3' and 5' signals which are required for proper transcription by RNA polymerase I and recognition and transcription by the negative-sense, single-stranded RNA virus polymerase; and (ii) measuring the expression or activity of a gene product encoded by the reporter gene, wherein a compound that modulates replication of the negative-sense, single-stranded RNA virus is identified if the expression or activity of the reporter gene product is altered in the presence of the compound or member of a library of compounds compared to expression or activity of the reporter gene product in the absence of the compound or member of a library of compounds or a negative control.

3.1 Terms

As used herein, the term "about" or "approximately" when used in conjunction with a number refers to any number within 1, 5 or 10% of the referenced number.

As used herein, the term "compound," unless otherwise specified or apparent from the context, refers to any agent that is being tested for its ability to modulate viral replication or has been identified as modulating viral replication, including the particular structures provided herein or incorporated by reference herein, and solvates, hydrates, prodrugs, stereoisomers and pharmaceutically acceptable salts thereof. Compounds include, but are not limited to, proteinaceous molecules, including, but not limited to, peptides (including dimers and multimers of such peptides), polypeptides, proteins, including post-translationally modified proteins, conjugates, antibodies, antibody fragments etc.; small molecules, including inorganic or organic compounds; nucleic acid molecules including, but not limited to, double-stranded or single-stranded DNA, or double-stranded or single-stranded RNA, antisense RNA, RNA interference (RNAi) molecules (e.g., small interfering RNA (siRNA), micro-RNA (miRNA), short hairpin RNA (shRNA), etc.), intron sequences, triple helix nucleic acid molecules and aptamers; carbohydrates; and lipids. In one embodiment, a compound is one of the compounds identified in Section 5.1. In one embodiment, a compound is purified.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of a viral infection or a symptom associated therewith; (ii) reduce the duration of a viral infection or a symptom associated therewith; (iii) prevent the progression of a viral infection or a symptom associated therewith; (iv) cause regression of a viral infection or a symptom associated therewith; (v) prevent the development or onset of a viral infection or a symptom associated therewith; (vi) prevent the recurrence of a viral infection or a symptom associated therewith; (vii) reduce or prevent the spread of a virus from one cell to another cell, one tissue to another tissue, or one organ to another organ; (ix) prevent or reduce the spread of a virus from one subject to another subject; (x) reduce organ failure associated with a viral infection; (xi) reduce hospitalization of a subject; (xii) reduce hospitalization length; (xiii) increase the survival of a subject with a viral infection; (xiv) eliminate a virus infection; (xv) inhibit or reduce virus replication; (xvi) inhibit or reduce the entry of a virus into a host cell(s); (xviii) inhibit or reduce replication of the viral genome; (xix) inhibit or reduce synthesis of viral proteins; (xx) inhibit or reduce assembly of viral particles; (xxi) inhibit or reduce release of viral particles from a host cell(s); (xxii) reduce viral titer; and/or (xxiii) enhance or improve the prophylactic or therapeutic effect(s) of another therapy.

As used herein, the term "effective amount" in the context of a compound for use in propagating viruses refers to an amount of a compound which is sufficient to increase virus replication in a substrate for virus propagation (e.g., tissue culture). In a specific embodiment, the effective amount is an amount of a compound which is sufficient to increase viral titer. In certain embodiments, an "effective amount" in the context of a compound for use in propagating viruses refers to the amount of a compound that increases virus titer by at least 5 fold, at least 10 fold, at least 12 fold, at least 15 fold, at least 20 fold or at least 25 fold. In some embodiments, an "effective amount" in the context of a compound for use in propagating viruses refers to the amount of a compound that increases virus titer by at least 1.5 logs, at least 2 logs, at least 3 logs, at least 4 logs or at least 5 logs.

As used herein, the term "enhancer" refers to a compound that increases viral replication as measured in any of the assays as taught herein or known to one of skill in the art. In some embodiments, an enhancer increases viral genome replication and/or viral protein synthesis. In some embodiments, an enhancer increases the kinetics of viral replication. In some embodiments, the enhancer increases viral yield. In some embodiments, an enhancer increases infectivity of the virus. In some embodiments, an enhancer increases growth of the virus.

In certain embodiments, an enhancer increases the virus replication by at least 1.5 fold, 2 fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In a specific embodiment, an enhancer of viral replication is identified if a compound increases the virus replication by at least 2 fold, 5 fold or 10 fold relative to virus replication in the absence of compound or the presence of a negative control. In certain embodiments, an enhancer of viral replication increases the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, an enhancer of viral replication increase the virus replication by approximately 2 logs or more, approximately 3 logs or more, approximately 4 logs or more, approximately 5 logs or more, or 2 to 10 logs or 2 to 5 logs relative to virus replication in the absence of compound or the presence of a negative control.

In one embodiment, an increase in viral replication is measured using a high throughput assay described in Section 5.2, infra. In one embodiment, an increase in viral replication is measured by: (a) contacting a compound or a member of a library of compounds with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection; and (b) measuring virus replication. The cells used in the assay should be susceptible to infection by the chosen virus and can be infected at different MOIs. The effect of a compound on virus replication can be assessed by measuring virus replication at different times post-infection. For example, virus replication may be measured 6 hours, 12 hours, 16 hours, 24 hours, 48 hours or 72 hours post-infection, using any method known to one of skill in the art can be used measure virus replication. In one embodiment, an increase in viral replication is assessed by measuring viral titer (as determined, e.g., by plaque formation). In another embodiment, an increase in viral replication is assessed by measuring the production of viral proteins (as determined, e.g., by Western blot analysis, ELISA or flow cytometry). In another embodiment, an increase in viral replication is assessed by measuring the production of viral nucleic acids (as determined, e.g., by RT-PCR or Northern blot analysis) using techniques known to one of skill in the art. See Sections 5.3.1.1-5.3.1.6 below for more details of techniques for measuring viral replication.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject with a viral infection. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a viral infection.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In one embodiment, an infection refers to the pathological state resulting from the presence of the virus in a cell or a subject, or by the invasion of a cell or subject by the virus.

As used herein, the term "inhibitor" refers to a compound that decreases viral replication as measured in any of the assays as taught herein or known to one of skill in the art. In some embodiments, an inhibitor completely inhibits viral replication. In some embodiments, an inhibitor decreases viral genome replication and/or viral protein synthesis. In some embodiments, an inhibitor decreases the kinetics of viral replication. In some embodiments, an inhibitor decreases viral yield. In some embodiments, an inhibitor decreases infectivity of the virus. In some embodiments, an inhibitor decreases growth of the virus.

In certain embodiments, an inhibitor reduces the virus replication by at least 1.5 fold, 2, fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In a specific embodiment, an inhibitor reduces the virus replication by at least 2 log relative to virus replication in the absence of compound or the presence of a negative control. In certain embodiments, an inhibitor of viral replication reduces the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, an inhibitor of viral replication reduces the virus replication by approximately 2 logs or more, approximately 3 logs or more, approximately 4 logs or more, approximately 5 logs or more, or 2 to 10 logs or 2 to 5 logs relative to virus replication in the absence of compound or the presence of a negative control.

In one embodiment, a decrease in viral replication is measured using a high throughput assay described in Section 5.2, infra. In one embodiment, a decrease in viral replication is measured by: (a) contacting a compound or a member of a library of compounds with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection; and (b) measuring virus replication. The cells used in the assay should be susceptible to infection by the chosen virus and can be infected at different MOIs. The effect of a compound on virus replication can be assessed by measuring virus replication at different times post-infection. For example, virus replication may be measured 6 hours, 12 hours, 16 hours, 24 hours, 48 hours or 72 hours post-infection, using any method known to one of skill in the art can be used measure virus replication. In one embodiment, a decrease in viral replication is assessed by measuring viral titer (as determined, e.g., by plaque formation). In another embodiment, a decrease in viral replication is assessed by measuring the production of viral proteins (as determined, e.g., by Western blot analysis, ELISA or flow cytometry). In another embodiment, a decrease in viral replication is assessed by measuring the production of viral nucleic acids (as determined, e.g., by RT-PCR or Northern blot analysis) using techniques known to one of skill in the art. See Sections 5.3.1.1-5.3.1.6 below for more details of techniques for measuring viral replication.

As used herein, the term "library" in the context of compounds refers to a plurality of compounds. A library can be a combinatorial library, e.g., a collection of compounds synthesized using combinatorial chemistry techniques, or a collection of unique chemicals with a low molecular weight (less than 1000 Daltons).

As used herein, the numeric term "log" refers to $\log_{10}$.

As used herein, the terms "manage," "managing," and "management," in the context of the administration of a therapy to a subject, refer to the beneficial effects that a subject derives from a therapy, which does not result in a cure of a viral infection. In certain embodiments, a subject is administered one or more therapies to "manage" a disease so as to prevent the progression or worsening of the viral infection.

As used herein, the phrase "multiplicity of infection" or "MOI" is the average number of virus per infected cell. The MOI is determined by dividing the number of virus added (ml added×PFU) by the number of cells added (ml added×cells/ml).

As used herein, the terms "prevent," "preventing" and "prevention" in the context of the administration of a therapy(ies) to a subject to prevent a viral infection refer to one or more of the following effects resulting from the administration of a therapy or a combination of therapies: (i) the inhibition of the development or onset of a viral infection and/or a symptom associated therewith; and (ii) the inhibition of the recurrence of a viral infection and/or a symptom associated therewith.

As used herein, the terms "prophylactic agent" and "prophylactic agents" refer to any agent(s) (e.g., a compound) which can be used in the prevention of a viral infection or a symptom associated therewith. In a specific embodiment, a prophylactic agent is an agent which is known to be useful to or has been or is currently being used to prevent or impede the onset and/or development of a viral infection or a symptom associated therewith.

As used herein, the term "prophylactically effective amount" refers to the amount of a therapy (e.g., prophylactic agent) which is sufficient to prevent a viral infection or a symptom thereof in a subject. In certain embodiments of the invention, a "prophylactically effective amount" is the amount of a compound that reduces the incidence of a viral infection in a subject. In a specific embodiment, the incidence of a viral infection in a subject is reduced by at least 2.5%, at least 5%, at least 10%, at least 15%, at least 25%, at least 35%, at least 45%, at least 50%, at least 75%, at least 85%, by at least 90%, at least 95%, or at least 99% in a subject administered a compound relative to a subject or group of subjects (e.g., two, three, five, ten or more subjects) not administered a compound.

As used herein, the term "purified," in the context of a compound that is chemically synthesized, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds.

As used herein, the terms "purified" and "isolated" when used in the context of a compound (including proteinaceous agents such as peptides) that is obtained from a natural source, e.g., cells, refers to a compound which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound that has been separated from the material (e.g., cellular components of the cells) from which it is isolated. Thus, a compound that is isolated includes preparations of a compound having less than about 30%, 20%, 10%, 5%, 2%, or 1% (by dry weight) of cellular materials and/or contaminating materials.

A "purified" or "isolated" nucleic acid sequence or nucleotide sequence, such as an RNAi molecule (e.g., siRNA, miRNA, shRNA, etc.) or a vector construct for producing an RNAi molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

As used herein, the term "purified" in the context of viruses refers to a virus which is substantially free of cellular material and culture media from the cell or tissue source from which the virus is derived. The language "substantially free of cellular material" includes preparations of virus in which the virus is separated from cellular components of the cells from which it is isolated or recombinantly produced. Thus, virus that is substantially free of cellular material includes preparations of protein having less than about 30%, 20%, 10%, or 5% (by dry weight) of cellular protein (also referred to herein as a "contaminating protein"). The virus is also substantially free of culture medium, i.e., culture medium represents less than about 20%, 10%, or 5% of the volume of the virus preparation. A virus can be purified using routine methods known to one of skill in the art including, but not limited to, chromatography and centrifugation.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the term "small molecules" and "small molecular weight compounds" and analogous terms include, but are not limited to, peptides, peptidomimetics, amino acids, amino acid analogs, polynucleotides, polynucleotide analogs, nucleotides, nucleotide analogs, other organic and inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed. In one embodiment, the small molecule is an organic compound other than a peptide, peptidomimetic, amino acid, amino acid analog, polynucleotide, polynucleotide analog, nucleotide or nucleotide analog.

As used herein, the terms "subject" or "patient" are used interchangeably. As used herein, the terms "subject" and "subjects" refer to an animal (e.g., birds, reptiles, and mammals), preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the term "premature human infant" refers to a human infant born at less than 37 weeks of gestational age.

As used herein, the term "human infant" refers to a newborn to 1 year old year human.

As used herein, the term "human child" refers to a human that is 1 year to 18 years old.

As used herein, the term "human adult" refers to a human that is 18 years or older.

As used herein, the term "elderly human" refers to a human 65 years or older.

As used herein, the term "synergistic," in the context of the effect of therapies, refers to a combination of therapies which is more effective than the additive effects of any two or more single therapies. In a specific embodiment, a synergistic effect of a combination of therapies permits the use of lower dosages of one or more of therapies and/or less frequent administration of said therapies to a subject with a viral infection. In certain embodiments, the ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a viral infection. In some embodiments, a synergistic effect results in improved efficacy of therapies (e.g., prophylactic or therapeutic agents) in the prevention, management and/or treatment of a viral infection. In some embodiments, a synergistic effect of a combination of therapies (e.g., prophylactic or therapeutic agents) avoids or reduces adverse or unwanted side effects associated with the use of any single therapy.

As used herein, the terms "therapies" and "therapy" can refer to any protocol(s), method(s), compound(s), composition(s), formulation(s), and/or agent(s) that can be used in the prevention, treatment, management, or amelioration of a viral infection or a symptom associated therewith. In certain embodiments, the terms "therapies" and "therapy" refer to biological therapy, supportive therapy, and/or other therapies useful in treatment, management, prevention, or amelioration of a viral infection or a symptom associated therewith known to one of skill in the art.

As used herein, the term "therapeutically effective amount" refers to the amount of a therapy, which is sufficient to treat and/or manage a viral infection. In certain embodiments of the invention, a "therapeutically effective amount" is the amount of a compound that reduces the severity, the duration and/or the symptoms associated with a viral infection in a subject. In certain other embodiments of the invention, a "therapeutically effective amount" is the amount of a compound that results in a reduction in viral titer by at least 1.5 logs, at least 2 logs, at least 3 logs, at least 4 logs, or at least 5 logs in a subject administered a compound relative to the viral titer in a subject or group of subjects (e.g., two, three, five, ten or more subjects) not administered a compound. In certain other embodiments of the invention, a "therapeutically effective amount" is the amount of a compound that results in a reduction in viral titer by 1.5 to 10 logs, 1.5 to 5 logs, 2 to 10 logs, 2 to 5 logs, or 2 to 4 logs in a subject administered a compound relative to the viral titer in a subject or group of subjects (e.g., two, three, five, ten or more subjects) not administered a compound.

As used herein, the terms "therapeutic agent" and "therapeutic agents" refer to any agent(s) (e.g., a compound) which can be used in the prevention, treatment and/or management of a viral infection or a symptom associated therewith. In a specific embodiment, a therapeutic agent is an agent which is known to be useful for, or has been or is currently being used for the prevention, treatment, and/or management of a viral infection or a symptom associated therewith.

As used herein, the terms "treat," "treatment," and "treating" refer in the context of administration of a therapy(ies) to a subject to treat a viral infection to a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of a viral infection and/or a symptom associated therewith; (ii) the reduction in the duration of a viral infection and/or a symptom associated therewith; (iii) the regression of a viral infection and/or a symptom associated therewith; (iv) the reduction of the titer of a virus; (v) the reduction in organ failure associated with a viral infection; (vi) the reduction in hospitalization of a subject; (vii) the reduction in hospitalization length; (viii) the increase in the survival of a subject; (ix) the elimination of a virus infection; (x) the inhibition of the progression of a viral infection and/or a symptom associated therewith; (xi) the prevention of the spread of a virus from a cell, tissue, organ or subject to another cell, tissue, organ or subject; (xii) the inhibition or reduction in the entry of a virus into a host cell(s); (xiii) the inhibition or reduction in the replication of the viral genome; (xiv) the inhibition or reduction in the synthesis of viral proteins; (xv) the inhibition or reduction in the release of viral particles from a host cell(s); and/or (xvi) the enhancement or improvement the therapeutic effect of another therapy. In some embodiments, the terms "treat," "treatment," and "treating" refer to the administration of the compounds to cells or another virus substrate.

Definitions of the more commonly recited chemical groups are set forth below. Certain variables in classes of compounds disclosed herein recite other chemical groups. Chemical groups recited herein, but not specifically defined, have their ordinary meaning as would be known by a chemist skilled in the art.

An "alkyl" group as used herein is a saturated straight chain or branched non-cyclic hydrocarbon having from 1 to 20 carbon atoms. Representative alkyl groups include, but are not limited to, -methyl, -ethyl, -n-propyl, -n-butyl, -n-pentyl, -n-hexyl, -n-heptyl and -n-octyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. An alkyl group can be substituted or unsubstituted. For example, an alkyl group can be substituted with hydroxy, halogen, carboxy, naphthyl, pyridine, or phenyl, each further optionally substituted with alkyl, hydroxy, trifluoromethyl, alkoxy, nitro or halogen, where appropriate.

An "amino" group as used herein is a —$NH_2$, —NHR or —$NR_2$ group, wherein each R is independently alkyl, alkoxy, amino, cycloalkyl, phenyl, or the R groups taken together with the nitrogen to which they are attached can form a heterocycle, each further optionally substituted with alkyl, hydroxy, trifluoromethyl, alkoxy, nitro or halogen, where appropriate.

A "guanidino" group as used herein is a —N=C(NHR)$_2$ group, wherein R is any appropriate substituent including, but not limited to, H, benzyl, or substituted or unsubstituted alkyl.

The term "halogen" means fluorine, chlorine, bromine and iodine.

A "heterocyclic ring" is a non aromatic cycloalkyl in which one or more of the ring carbon atoms are independently replaced with a heteroatom from the group consisting of O, S, and N. Representative examples of a heterocyclic ring include, but are not limited to, aziridine, pyrrolidine, piperidine, morpholine, or thiomorpholine. In certain embodiments the heterocyclic ring may encompass a heterocyclic ring that is fused to a 6 membered aromatic ring system, such as a phenyl ring. In one embodiment the heterocyclic ring system is indoline or isoindoline.

In one embodiment, when groups described herein are said to be "substituted," they may be substituted with any suitable substituent or substituents. Illustrative examples of substituents include those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, See for example, Remington's Pharmaceutical Sciences, 18th eds., Mack Publishing, Easton Pa. (1990) or Remington: The Science and Practice of Pharmacy, 19th eds., Mack Publishing, Easton Pa. (1995).

As used herein and unless otherwise indicated, the term "hydrate" means a compound, or a salt thereof, that further includes a stoichiometric or non-stoichiometric amount of water bound by non-covalent intermolecular forces.

As used herein and unless otherwise indicated, the term "solvate" means a compound, or a salt thereof, that further includes a stoichiometric or non-stoichiometric amount of a solvent bound by non-covalent intermolecular forces.

As used herein and unless otherwise indicated, the term "prodrug" means a compound derivative that can hydrolyze, oxidize, or otherwise react under biological conditions (in vitro or in vivo) to provide compound. Examples of prodrugs include, but are not limited to, derivatives and metabolites of a compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

As used herein and unless otherwise indicated, the term "stereoisomer" or "stereomerically pure" means one stereoisomer of a compound, in the context of an organic or inorganic molecule, that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The compounds can have chiral centers and can occur as racemates, individual enantiomers or diastereomers, and mixtures thereof. All such isomeric forms are included within the embodiments disclosed herein, including mixtures thereof.

Various compounds contain one or more chiral centers, and can exist as racemic mixtures of enantiomers, mixtures of diastereomers or enantiomerically or optically pure compounds. The use of stereomerically pure forms of such compounds, as well as the use of mixtures of those forms are encompassed by the embodiments disclosed herein. For example, mixtures comprising equal or unequal amounts of the enantiomers of a particular compound may be used in methods and compositions disclosed herein. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon compounds (McGraw-Hill, N.Y., 1962); and Wilen, S. H., Tables of Resolving Agents and Optical Resolutions p. 268 (E. L. Eliel, Ed., Univ. of Notre Dame Press, Notre Dame, Ind., 1972).

It should also be noted that compounds, in the context of organic and inorganic molecules, can include E and Z isomers, or a mixture thereof, and cis and trans isomers or a mixture thereof. In certain embodiments, compounds are isolated as either the E or Z isomer. In other embodiments, compounds are a mixture of the E and Z isomers.

4. DESCRIPTION OF THE FIGURES

FIG. 1. Influenza virus mini-genome reporter construct and high-throughput screening (HTS) results. (A) Schematic of the influenza virus luciferase reporter construct. The firefly luciferase open reading frame was inserted in the reverse orientation and complementary sense between the influenza virus non-coding regions which serve as the viral promoter. This cassette is flanked by a human RNA polymerase I (Pol I) promoter and a hepatitis delta virus (HDV) ribozyme. The transcribed RNA (vRNA) has exact ends and mimics an influenza virus genome segment. Upon infection, the influenza virus polymerase recognizes the promoter and the reporter gene is transcribed and expressed. (B) Results of the HTS of known bioactive compounds. Three libraries (NINDS, Prestwick and BIOMOL) were screened containing 2640 known bioactive compounds. Strong inhibition was defined as a 90-100% reduction in luminescence, medium inhibition as a 70-89% reduction and an increase in luminescence of at least 2 fold was classified as an enhancement.

Figure 2:
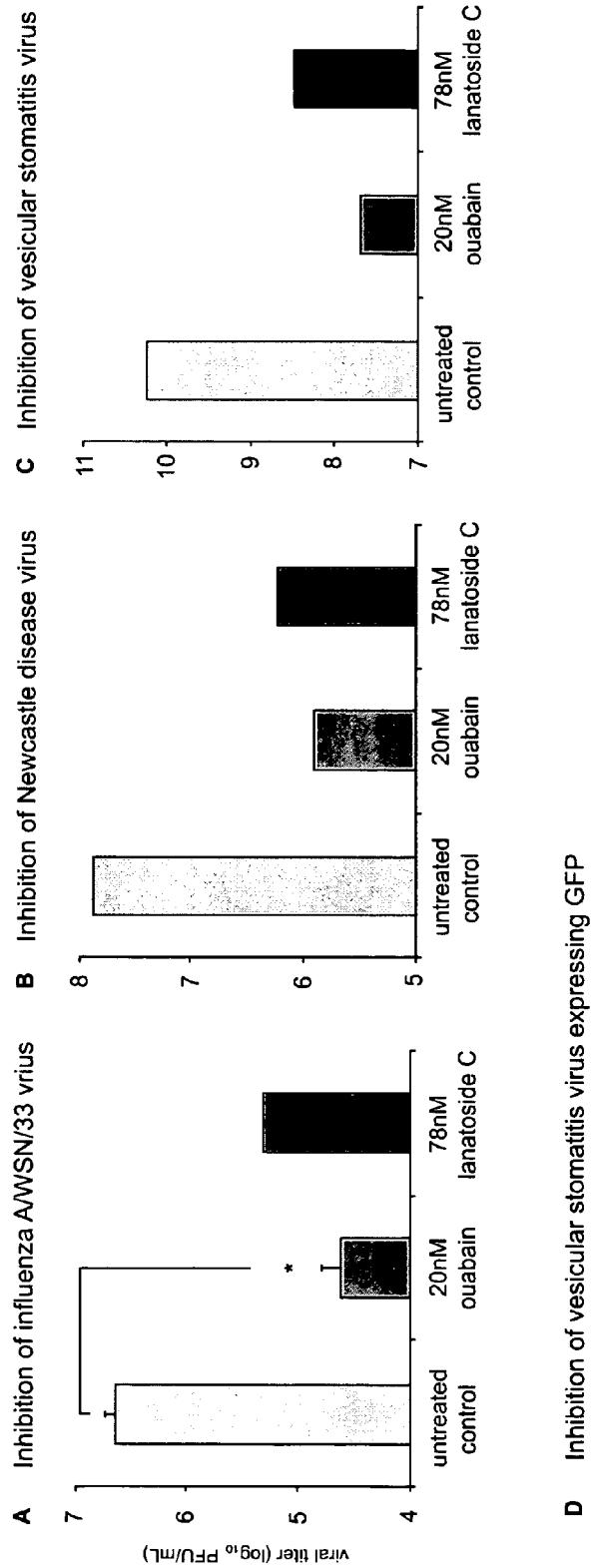
Figure 2:
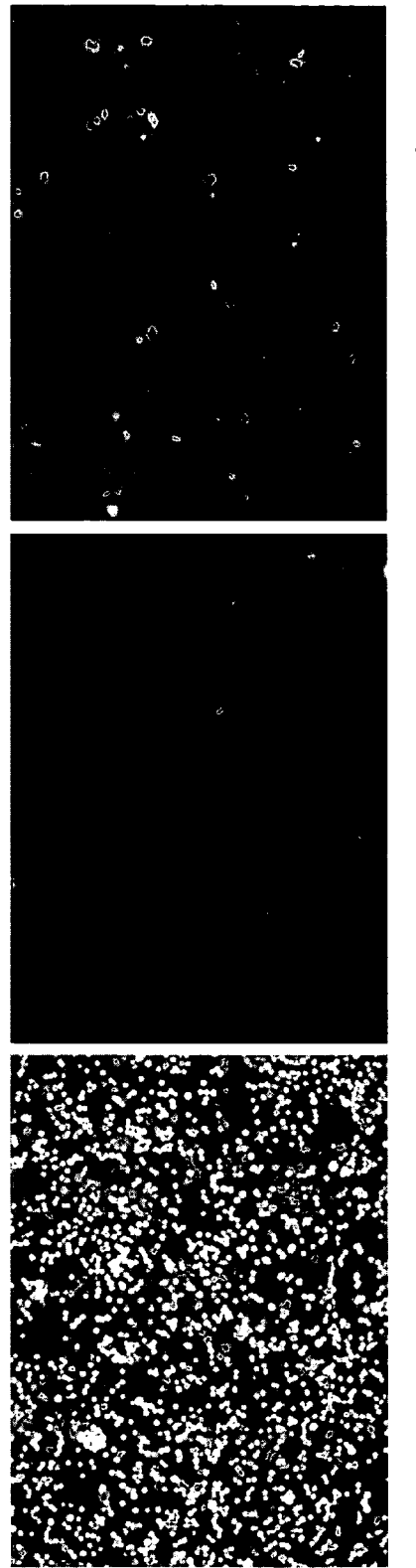

FIG. 2. Inhibition of negative sense RNA viruses by $Na^+$/$K^+$/ATPase pump inhibitors. A549 cells were infected with (A) A/WSN/33 (MOI=1), (B) NDV/B1 (MOI=1) or (C and D) VSV-GFP (MOI=1) in the presence of 20 nM ouabain or 78 nM lanatoside C. Viral titers were determined 24 hours post infection by plaque assays (A, B, C) and the growth of VSV-GFP was in addition visualized by fluorescence microscopy (D). The assay was performed in triplicate for (A) testing ouabain and is presented as the mean±standard deviation. Student's t test: *, P≤0.05.

Figure 3:
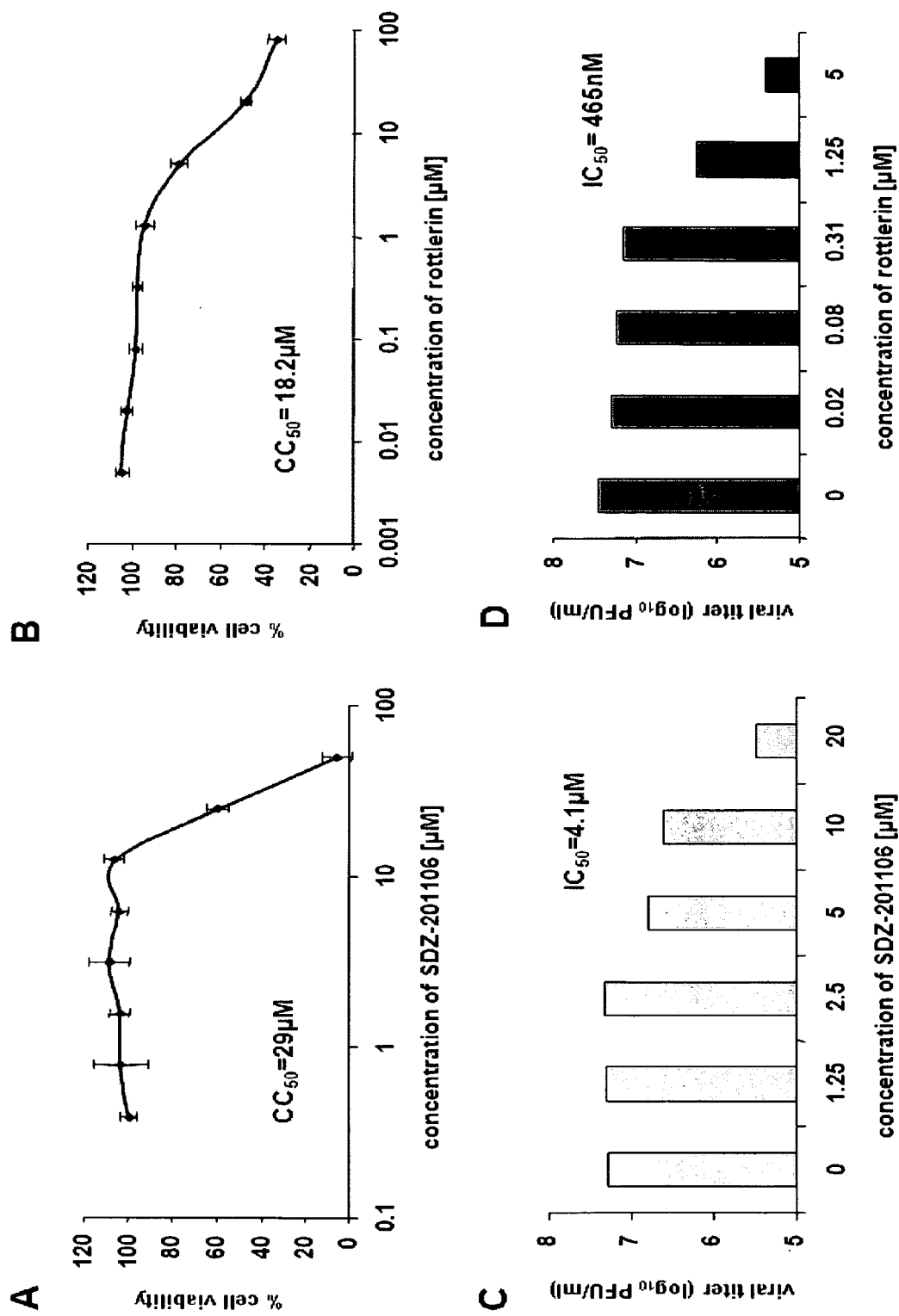

FIG. 3. Cytotoxicity of inhibitory compounds in A549 cells and their impact on the replication of influenza A virus. (A) Cytotoxicity profiles of SDZ-201106 and rottlerin. A549 were seeded into 96-well plates and treated for 24 h with the indicated concentrations of SDZ-201106 (Na$^+$-channel opener) or rottlerin (PKC inhibitor). Absorbance of formazan was measured 2 hours after adding the MTS substrate at a wavelength of 450 nm. The data represent the averages of 5 wells±standard deviation of the mean. (B) Inhibition of influenza replication by SDZ-201106 and rottlerin. A549 cells were infected with influenza A/WSN/33 virus (MOI=1) in the presence of the indicated concentrations of SDZ-201106 or rottlerin. (C, D) Viral titers were determined 24 hours post infection by plaque assay in MDCK cells.

Figure 4:
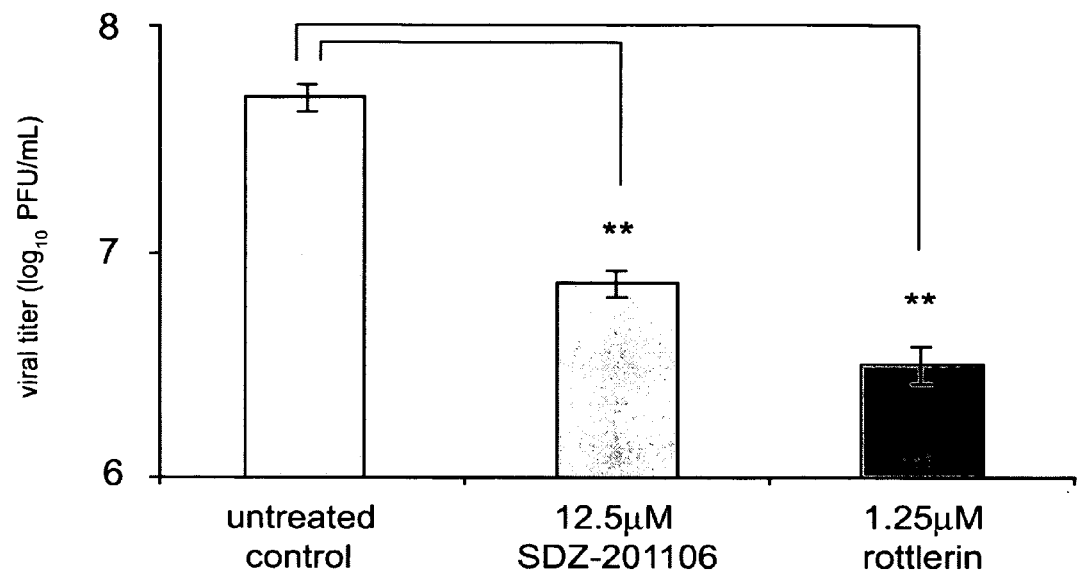
Figure 4:
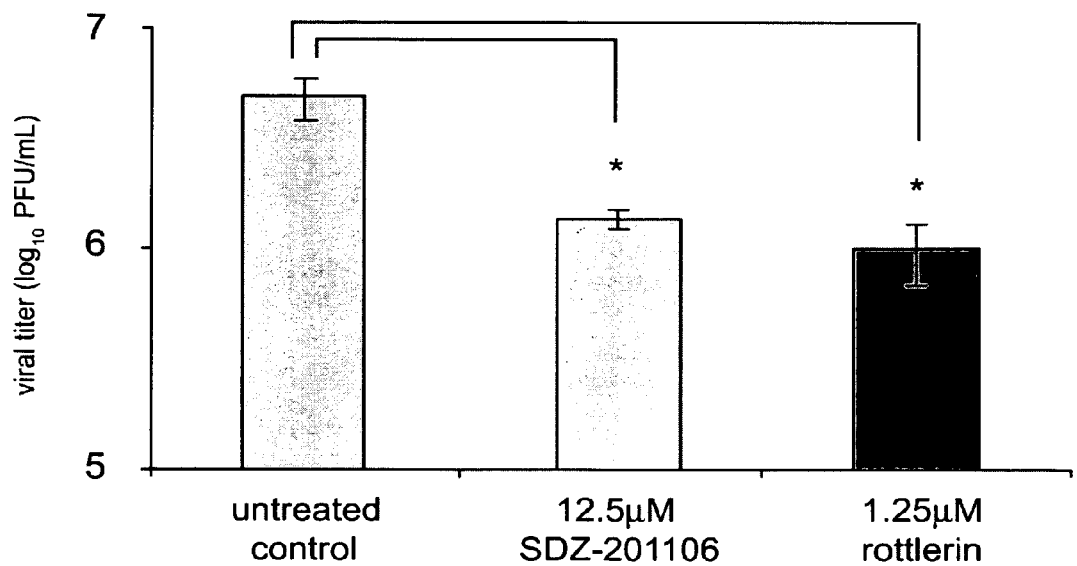

FIG. 4. Inhibition of influenza A and B viruses by a Na$^+$-channel opener and a PKC inhibitor. A549 cells were infected with either (A) A/WSN/33 (MOI=1) or (B) B/Yamagata/88 (MOI=5) in the presence of 12.5 μM SDZ-201106 (Na$^+$-channel opener) or 1.25 μM rottlerin (PKC inhibitor). Viral titers were determined 24 hours post infection by plaque assays in MDCK cells. The assay was performed in triplicate and is presented as the mean±standard deviation. Student's t test: *, P≤0.05; **, P≤0.01.

FIG. 5. Enhancement of influenza A virus replication by Na$^+$-channel inhibitors and PKC activators. A549 cells were infected with influenza A/WSN/33 virus (MOI=0.001) in the presence of (A) Na$^+$-channel inhibitors (400 nM 2',4'-dichlorobenzamil and 10 μM phenamil) and (B) PKC activators (250 nM mezerein and 250 nM PMA). Viral titers were measured at 24, 36, 48 and 60 hours post infection by plaque assay in MDCK cells. The assay was performed in triplicate and is presented as the mean±standard deviation. Student's t test: *, #, P≤0.05; **, ##, P≤0.01 (* refers to data points for 2',4'-dichlorobenzamil (A) and for mezerein (B), refers to data points for phenamil (A) and PMA (B)).

Figure 6:
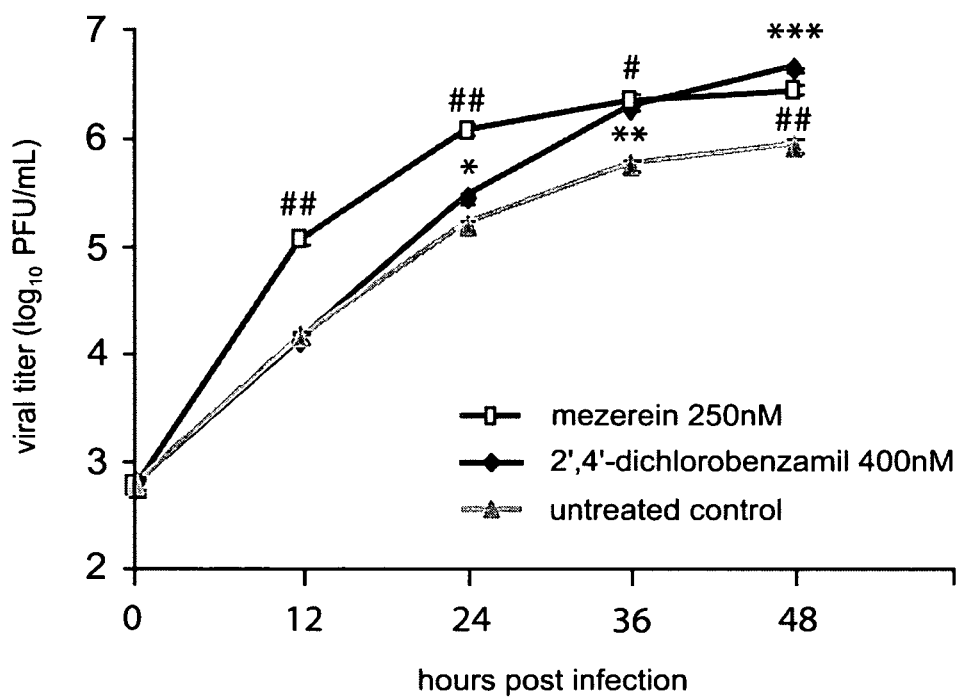

FIG. 6. Enhancement of influenza B virus replication by a Na$^+$-channel inhibitor and a PKC activator. A549 cells were infected with influenza B/Yamagata/88 virus (MOI=0.1) in the presence of 400 nM 2',4'-dichlorobenzamil (Na$^+$-channel inhibitor) and 250 nM mezerein (PKC activator). Viral titers were measured at 0, 12, 24, 36 and 48 hours post infection by plaque assay in MDCK cells. The assay was performed in triplicate and is presented as the mean±standard deviation. Student's t test: *,#, P≤0.05; ,##, P≤0.01; *, P≤0.001 (* refers to data points for 2',4'-dichlorobenzamil and # refers to data points for mezerein).

FIG. 7. Enhanced growth of human isolates of influenza viruses and a reassortant H5N1 influenza vaccine strain. A549 cells were infected with (A) A/Wyoming/03/2003 (MOI=0.01), (B) A/Moscow/10/99 (MOI=0.01) and (C) 6:2 reassortant H5N1/PR8 (MOI=0.001) in the presence of (A, B, C) 400 nM 2',4'-dichlorobenzamil or (A, B) 250 nM mezerein. Viral titers were measured at indicated time points post infection by plaque assay in MDCK cells. (C) The assay was performed in triplicate and is presented as the mean±standard deviation. Student's t test: *, P≤0.05; **, P≤0.01.

FIG. 8. Influenza A virus growth in response to 2',4'-dichlorobenzamil versus 3',4'-dichlorobenzamil. A549 cells were infected with influenza A/WSN/33 virus (MOI=0.001) in the presence 400 nM of 2',4'- or 3',4'-dichlorobenzamil. Viral titers were determined at 48 hours post infection by plaque assay in MDCK cells. The assay was performed in triplicate and is presented as the mean±standard deviation. Student's t test: **, P≤0.01.

FIG. 9. A549 cells were infected with influenza virus in the absence or presence of SDZ-201106 (used at 12.5 μM) (A) or rottlerin (used at 1.25 μM) (B). After 24 hours, the virus was collected. After 15 passages in the absence or presence of SDZ-201106 (A) or after 17 passages in the absence or presence of rottlerin (B), the susceptibility of the viruses to the compounds was determined. Growth of the passaged viruses in the presence of compound was compared to that of unpassaged virus (titers were determined by plaque assay in MDCK cells). (A) Student's t test: *, P≤0.01; (B) Student's t test: *, P≤0.05.

FIG. 10. A549 cells were infected with influenza virus WSN (MOI=1) in the presence of A3 (added at the indicated times post infection). Virus growth was measured using a plaque assay at 24 hours post infection. The assay was performed in triplicate and is presented as the mean±standard deviation. hpi=hours post infection.

FIG. 11. A549 cells were infected with influenza virus WSN (MOM) in the presence of A35 (added at the indicated times post infection). Virus growth was measured using a plaque assay at 24 hours post infection.

FIG. 12. A549 cells were infected with influenza virus WSN (MOI=1) in the presence of C2 (added at the indicated times post infection). Virus growth was measured by plaque assay at 24 hours post infection. The assay was performed in triplicate and is presented as the mean±standard deviation. hpi=hours post infection.

FIG. 13. A549 cells were infected with influenza B/Yamagata/88 virus (MOI=1) in the presence of A3, A35 and C2. Virus growth was measured 24 hours post infection. C2 was tested at a different time and therefore has its own untreated control. The assay was performed in triplicate and is presented as the mean±standard deviation. Student's t test: **, P<0.01; *, P<0.05.

FIG. 14. A549 cells were infected with NDV/B1 (A) and VSV (B) (MOI=1) in the presence of A3, A35 and C2. Virus growth was measured by plaque assay 24 hours post infection. C2 was tested at a different time and therefore has its own untreated control. The assay was performed in triplicate and is presented as the mean standard deviation.

FIG. 15. Mini-genome studies of Compounds A3, A35 and C2. Monolayers of A549 cells were transfected with expression plasmids for influenza virus NP, the 3 polymerase subunits (PB1, PB2, PA), a mini-genome comprising a luciferase reporter gene and an expression plasmid for renilla luciferase for normalization. Cells were pretreated for 4 hours prior to transfection and compounds were present after the transfection for an additional 20 hours. 3P/NP=control cells transfected with virus expression plasmids without inhibitor. Ribavirin, an inhibitor of RNA virus replication, is included as a control. The assay was performed in triplicate and is presented as the mean±standard deviation.

FIG. 16. Influenza virus polymerase activity in response to increasing concentrations of A3. A549 cells were transfected with expression plasmids for influenza virus A/WSN/33 NP and the 3 polymerase subunits (PB1, PB2, PA) and a mini-genome comprising a luciferase reporter gene in the presence of different concentrations of A3 and polymerase activity was measured.

5. DETAILED DESCRIPTION

5.1 Modulators of Virus Replication

Without being limited by theory, embodiments provided herein are based on the discovery that modulating one or more of protein kinase C ("PKC"), sodium channels, calcium channels or Na$^+$/K$^+$/ATPase pumps modulates viral replication. In particular, it has been found that PKC inhibitors, sodium channel openers, and Na$^+$/K$^+$/ATPase pump inhibitors reduce viral replication, and that PKC activators, sodium channel inhibitors and calcium channel inhibitors enhance viral replication.

Illustrative examples of PKC isoforms or isotypes that compounds set forth herein are useful for inhibiting or activating include, but are not limited to, PKCα, PKCβ, PKCβI, PKCβII, PKCδ, PKCε, PKCγ, PKCiota-Par6, PKCζ, nPKC, aPKC, and PKCη. PKC isoforms and isotypes can be Ca$^{2+}$ sensitive or insensitive.

Illustrative examples of sodium channels that compounds set forth herein are useful for inhibiting or activating include, but are not limited to, tetrodotoxin (TTX)-sensitive sodium channels, voltage-gated sodium channels, voltage-dependent sodium channels, amiloride-sensitive sodium channels, and cardiac sodium channels. Representative compounds that modulate tetrodotoxin (TTX)-sensitive sodium channels include, but are not limited to, Aconitine and Lappaconitine-.HBr. Representative compounds that modulate voltage-gated sodium channels include, but are not limited to, Anemone Toxin II, ATX II (recombinant), Batrachotoxin, BIA 2-093, Lamotrigine, Lidocaine, QX-314, and α- and (β-Pompilidotoxin. Representative compounds that modulate voltage-dependent sodium channels include, but are not limited to, μ-Conotoxin GIIIB, Grayanotoxin III, Kavain (+/−), Riluzole, Tetrodotoxin, and Tocainide.HCl. A representative compound that modulates amiloride-sensitive sodium channels is Phenamil methanesulfonate salt. A representative compound that modulates cardiac sodium channels is QX-314.

5.1.1 Inhibitors of Viral Replication

In one embodiment, provided herein are compounds with activity as inhibitors of PKC. Without being limited by theory, it is thought that compounds with activity as inhibitors of PKC are useful for the inhibition or reduction of the replication of negative-sense, single-stranded RNA viruses and, accordingly, are useful as antiviral agents. Accordingly, provided herein are methods for using inhibitors of PKC for the inhibition or reduction of the replication of negative-sense, single-stranded RNA viruses.

In a particular embodiment, compounds which have activity as inhibitors of PKC include, but are not limited to, rottlerin (PKCδ), Aurothioglucose hydrate (PKCiota-Par6), Bisindolylmaleimide II, IV, VI, VII, VIII, X and XI, Gö6983 (PKCα, PKCβ, PKCδ, PKCγ, PKCζ, in one embodiment PKCδ, PKCγ, PKCζ), Gö6976 (PKCα, PKCβI), Myristoylated PKCζ, HBDDE (PKCα, PKCγ), Ro 32-0432 (PKCα), CGP-53353 (PKCβII), Calphostin C (UCN-1028C), Chelerythrine Chloride, GF 109203X (PKCα, PKCβI, PKCβII, PKCγ), 1-O-Hexadecyl-2-O-acetyl-sn-glycerol, (±)1-O-Hexadecyl-2-O-methylglycerol, HA-100, Hypericin, Ilmofosine semisolid, Myristoylated PKC (20-28), Myristoylated EGFR Fragment (651-658), K-252b solution, KRIBB3, NPC-15437 dihydrochloride hydrate, Ro 31-8220, Phloretin, Protein Kinase C (19-31), Protein Kinase C Pseudosubstrate (19-36), Sphingosine, D-erythro, Staurosporine, Tamoxifen, UCN-01, and 12(S),20-diHETE. Particular PKC isoforms or isotypes that certain compounds are useful for inhibiting are set forth in parentheses following the compound name.

In one embodiment, the PKC inhibitor is rottlerin (Sigma-Aldrich, St. Louis, Mo., USA). In some embodiments, the PKC inhibitor is not bisindolylmaleimide I, such as bisindolylmaleimide I.HCl. In some embodiments, the PKC inhibitor is not 1-(5-inoquinolinesulphonyl)-2-methylpiperazine dihydrochloride (H7). In some embodiments, the PKC inhibitor is not staurosporine. In some embodiments, the PKC inhibitor is not calphostin C. In some embodiments, the PKC inhibitor is not GF 109203X. In some embodiments, the PKC inhibitor is not Gö6976. In some embodiments, the PKC inhibitor is not a peptide corresponding to the pseudo substrate domain of PKCα and PKCβ. In some embodiments, the PKC isoform is not PKCα. In some embodiments, the PKC isoform is not PKCβ. In some embodiments, a PKC inhibitor of the invention does not inhibit the PKC isoform PKCβII.

In one embodiment, provided herein are compounds with activity as a sodium channel opener. In a particular embodiment, provided herein are compounds with activity as an epithelial sodium channel opener. Without being limited by theory, it is thought that compounds with activity as a sodium channel opener are useful for the inhibition or reduction of the replication of negative-sense, single-stranded RNA viruses and, accordingly, are useful as antiviral agents. Accordingly, provided herein are methods for using sodium channel openers for the inhibition or reduction of the replication of negative-sense, single-stranded RNA viruses.

In a particular embodiment, compounds which have activity as a sodium channel opener include, but are not limited to, SDZ-201106 (±) (DPI-201106), SDZ-201106 (−), SDZ-201106 (+), Aconitine, Anemone Toxin II, Batrachotoxin, Brevetoxin 2 and 9, Grayanotoxin III, Monensin, Veratridine, and α- and β-Pompilidotoxin. In a particular embodiment, the sodium channel opener is SDZ-201106 (Enzo Life Sciences, Inc., Plymouth Meeting, Pa., USA).

In one embodiment, provided herein are compounds with activity as a calcium channel opener. Without being limited by theory, it is thought that compounds with activity as a calcium channel opener are useful for the inhibition or reduction of the replication of negative-sense, single-stranded RNA viruses and, accordingly, are useful as antiviral agents. Accordingly, provided herein are methods for using calcium channel openers for the inhibition or reduction of the replication of negative-sense, single-stranded RNA viruses.

In a particular embodiment, compounds which have activity as a calcium channel opener include, but are not limited to, BAY K8644 (±) and FPL-64176 (Sigma-Aldrich, St. Louis, Mo., USA).

In one embodiment, provided herein are compounds with activity as Na$^+$/K$^+$/ATPase pump inhibitors. Without being limited by theory, it is thought that compounds with activity as Na$^+$/K$^+$/ATPase pump inhibitors are useful for the inhibition or reduction of the replication of negative-sense, single-stranded RNA viruses and, accordingly, are useful as antiviral agents. Accordingly, provided herein are methods for using Na$^+$/K$^+$/ATPase pump inhibitors for the inhibition or reduction of the replication of negative-sense, single-stranded RNA viruses.

In a particular embodiment, compounds which have activity as Na$^+$/K$^+$/ATPase pump inhibitors include, but are not limited to, cardioactive glycosides. Illustrative examples of cardioactive glycosides include, but are not limited to, ouabain, digoxin, lanatoside C, and strophanthidin (Sigma-Aldrich, St. Louis, Mo., USA).

In a particular embodiment, compounds which inhibit or reduce the replication of negative-sense, single-stranded RNA viruses include, but are not limited to rottlerin, Aurothioglucose hydrate, Bisindolylmaleimide II, IV, VI, VII, VIII, X and XI, Gö6983, Gö6976, Myristoylated PKCζ, Peptide Inhibitor, HBDDE, Ro 32-0432, CGP-53353, Calphostin C (UCN-1028C), Chelerythrine Chloride, GF 109203X, 1-O-Hexadecyl-2-O-acetyl-sn-glycerol, (±)1-O-Hexadecyl-2-O-methylglycerol, HA-100, Hypericin, Ilmofosine semisolid, Myristoylated PKC (20-28), Myristoylated EGFR Fragment (651-658), K-252b solution, KRIBB3, NPC-15437 dihydrochloride hydrate, Ro 31-8220, Phloretin, Protein Kinase C (19-31), Protein Kinase C Pseudosubstrate (19-36), Sphingosine, D-erythro, Staurosporine, Tamoxifen, UCN-01, SDZ-201106 (±) (DPI-201106), SDZ-201106 (−), SDZ-201106 (+), digoxin, Aconitine, Anemone Toxin II, Batrachotoxin, Brevetoxin 2 and 9, Grayanotoxin III, Monensin, Veratridine, α- and β-Pompilidotoxin, and 12(S),20-diHETE, Antimycin A, Niclosamide, Quinacrine Hydrochloride, Digitoxigenin, Anisomycin, Cephaeline, Mitoxanthrone Hydrochloride, Mycophenolic Acid, Emitine Hydrochloride, Ellipticine, Papaverine Hydrochloride, Daunorubicin hydrochloride, Dequalinium Hydrochloride, Monensin Sodium Salt, Lasalocid Sodium, Strophanthidin, Cycloheximide, 5-Azacytidine, Gossypol, Ethaverine Hydrochloride, Digoxigenin, Proscillaridin A, Pyrvinium pamoate, Doxorubicin, Tyrphostin 9,5-iodotubercidin, Diphenyleneiodonium, Valinomycin, Mycophenolic acid, Z-Leu3-VS, Oligomycin A, PD 98059, LY-83583, Aklavain Hydroclioride, Acriflavinium Hydroclioride, Acrisorcin, Homidium Bromide, Pyrvinium Pamoate, Anisomycin, Lasalocid Sodium, Mycophenolic Acid, Actinomycin D, Teniposide, Cycloheximide, Pyrromycin, Mercaptopurine, Lapachol, Clotrimazole, Azathioprine, Camptothecin, Chlorhexidine hydrochloride, Phenformin hydrochloride, Atovaquone, Methotrexate, Berberine Chloride, Thioguanosine, Conessine, Methylbenzthonium Chloride, Benzethonium Chloride, Atenolol, Esculetin (6,7-Dihydroxycoumarin), Tracazolate, Naftifine hydrochloride, Halofantrine hydrochloride, 2,5-ditertbutylhydroquinone, FCCP, KT-5720, PCA 4248, Mitomycin C, Roscovitine, Nimesulide, U-0126, SU-4312, SB-431542, Cytochalasin D, EHNA, Etoposide, Chloroxine, Hycanthone, Magnocurarine Iodide, 2,4-Dinitrophenol, Mechlorethamine, Topotecan Hydrochloride, and Rosolic Acid.

In a specific embodiment, compounds which inhibit or reduce the replication of negative-sense, single-stranded RNA viruses include, but are not limited to ouabain and lanatoside C. In a particular embodiment, ouabain and lanatoside C are useful for inhibiting or reducing the replication of negative-sense, single-stranded segmented RNA viruses. In one embodiment, the virus is influenza A or B, parainfluenza or respiratory syncytial virus ("RSV"). In one embodiment, the virus is not Sendai virus.

In a specific embodiment, a compounds which inhibits or reduces the replication of negative-sense, single-stranded RNA viruses is strophanthidin. In a particular embodiment, strophanthidin is useful for inhibiting or reducing the replication of negative-sense, single-stranded segmented RNA viruses. In one embodiment, the virus is influenza A or B, parainfluenza or respiratory syncytial virus ("RSV"). In one embodiment, the virus is not Sendai virus.

In a specific embodiment, compounds which inhibit or reduce the replication of negative-sense, single-stranded RNA viruses include, but are not limited to ouabain, lanatoside C, digoxigenin, rottlerin, strophanthidin, Esculetin (6,7-Dihydroxycoumarin), SB-431542, EHNA, SDZ-201106 (±) (DPI-201106).

In some embodiments, compounds which inhibit or reduce the replication of negative-sense, single-stranded RNA viruses include, but are not limited to, a compound of formula C2 or pharmaceutically acceptable salts, hydrates, solvates, and prodrugs thereof. The compound of formula C2 (9-(benzo[d][1,3]dioxol-5-yl)-4-hydroxy-6,7-dimethoxynaphtho[2,3-c]furan-1(3H)-one) can be obtained commercially from AKos Consulting and Solutions GmbH, Steinen, Germany (Order Number AKG-4466-1901) or ZereneX Molecular Limited, Greater Manchester, United Kingdom (Order Number ZBioX-0173).

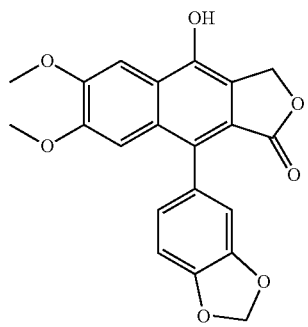

C2

In some embodiments, compounds which inhibit or reduce the replication of negative-sense, single-stranded RNA viruses include, but are not limited to, compounds of formula A3, A3-2, A3-3, A3-4, A3-5 or A3-6 or pharmaceutically acceptable salts, hydrates, solvates, and prodrugs thereof. The compound of formula A3 (2-(5-(2,3-dimethyl-1H-indol-5-yl)-1,3,4-oxadiazol-2-ylthio)-1-(pyrrolidin-1-yl)ethanone), A3-2 (2-(5-(2,3-dimethyl-1H-indol-5-yl)-1,3,4-oxadiazol-2-ylthio)-N,N-diethylacetamide), A3-3 (2-(5-(2,3-dimethyl-1H-indol-5-yl)-1,3,4-oxadiazol-2-ylthio)-1-(indolin-1-yl)ethanone), A3-4 (2-(5-(2,3-dimethyl-1H-indol-5-yl)-1,3,4-oxadiazol-2-ylthio)-N,N-diisopropylacetamide), A3-5 (2-(5-(2,3-dimethyl-1H-indol-5-yl)-1,3,4-oxadiazol-2-ylthio)-1-morpholinoethanone) and A3-6 (1-(azepan-1-yl)-2-(5-(2,3-dimethyl-1H-indol-5-yl)-1,3,4-oxadiazol-2-ylthio)ethanone) can be obtained commercially from Aurora Fine Chemicals LLC, San Diego, USA (Order Numbers kasi-277398, kasi-277402, kasi-277404, kasi-277407, kasi-277419, and kasi-277425) or Ryan Scientific Inc., Mt. Pleasant, USA (Order Numbers ASN04454782, ASN04454791, ASN04454796, ASN04454800, ASN04454819, ASN04454828).

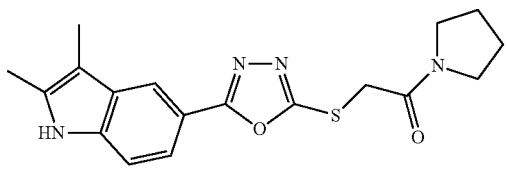

A3

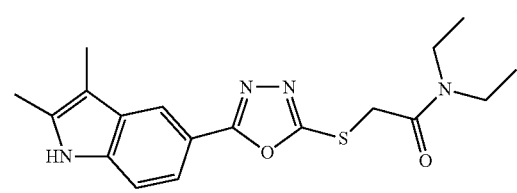

A3-2

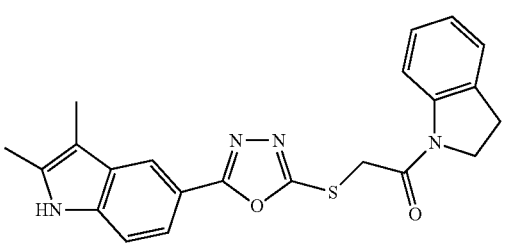

A3-3

-continued

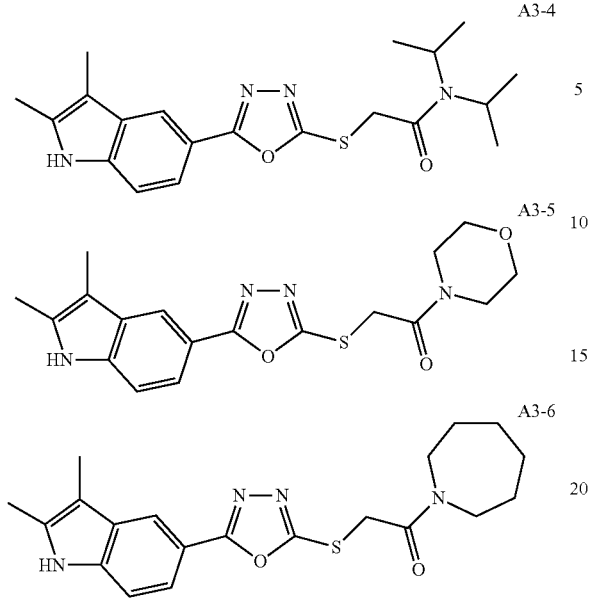

In some embodiments, compounds which inhibit or reduce the replication of negative-sense, single-stranded RNA viruses include, but are not limited to, compounds of formula A3-G

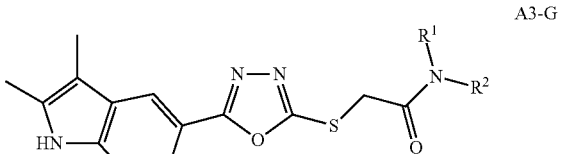

or pharmaceutically acceptable salts, hydrates, solvates, prodrugs and stereoisomers thereof, wherein:

$R^1$ and $R^2$ are at each occurrence independently a $C_1$-$C_8$ alkyl group; or $R^1$ and $R^2$, together with the nitrogen atom $R^1$ and $R^2$ are bound to, form a 3 to 8 membered saturated heterocyclic ring.

Compounds of formula A3-G may be obtained by the chemical synthesis described below or any other method known to the skilled artisan.

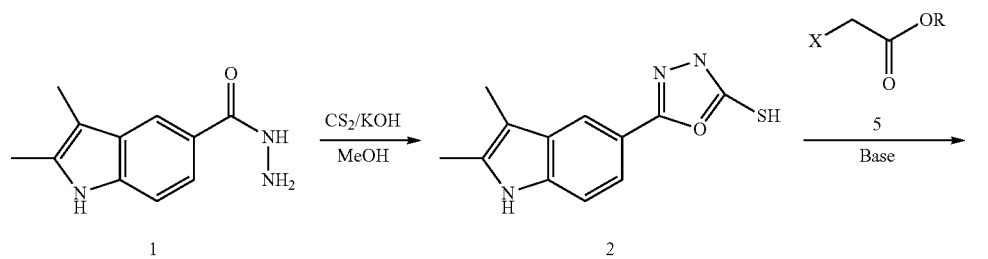

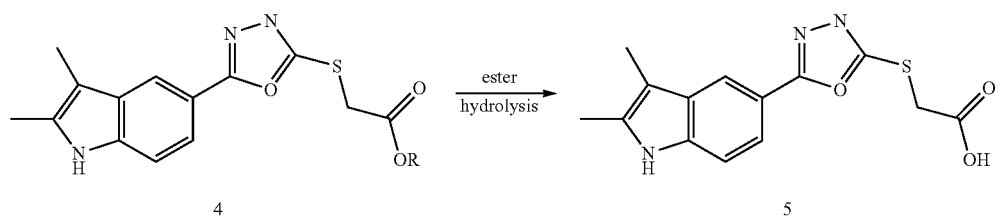

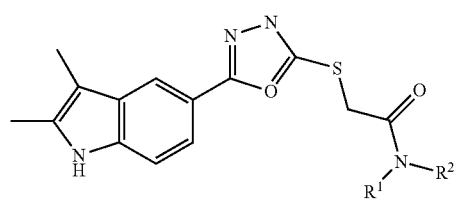

2,3-dimethyl-1H-indole-5-carbohydrazide (1) (ChemCollect GmbH, Remscheid, Germany; Order Number HY008960) may be reacted with carbon disulfide and a suitable base, such as potassium hydroxide, in a suitable solvent, such as methanol, at elevated temperature, such as 65° C. for an appropriate time, such as 7-24 hrs to give 5-(2,3-dimethyl-1H-indol-5-yl)-1,3,4-oxadiazole-2-thiol (2). See Boschelli et al., J. Med. Chem., 1993, 36(13), 1802. Alternatively, the oxadiazole (2) may be obtained reacting indole (1) with carbon disulfide, $Al_2O_3$ and potassium hydroxide under microwave irradiation. See Khan et al., Letters in Organic Chemistry, 2006, 3, 286. See also Padhy, Indian J. Chem., 2003, 40B, 910; Young et al., J. Am. Chem. Soc., 1955, 77, 118; El-Emam et al., J. Chem. Soc. Pak., 1987, 9, 87. Ester (4) may be obtained by alkylating oxadiazole (2) with a suitable alkylating agent (5), wherein X is a leaving group, such as a Cl, Br, I, or —SO$_2$Me or any of the leaving groups described in March, Advanced Organic Chemistry, 4$^{th}$ Edition, John Wiley & Sons New York (1992), pp. 352-357 and R is a suitable alkyl group, such as methyl or ethyl, using a suitable base, such as potassium carbonate, in a suitable solvent, such as acetonitrile, at a suitable temperature, such as room temperature to 82° C. In one embodiment thiol (2) may be reacted with bromo methylacetate (Sigma-Aldrich, Milwaukee, USA, Order Number 303208) in acetonitrile using potassium carbonate to give ester (4), wherein R is methyl. Amide (6) may be obtained by reacting NHR$^1$R$^2$, commercially available or synthesized as described in March, Advanced Organic Chemistry, 4$^{th}$ Edition, John Wiley & Sons New York (1992), with ester (4). See Zabicky, The Chemistry of Amides, Wiley, New York (1970), pp. 96-105. For a list of reagents with references, see Larock, Comprehensive Organic Transformations, VCH New York (1989), pp. 987-988. Strong basic catalysis may be employed, as well as catalysis by cyanide ions or high pressure. See Matsumoto et al., Chem. Ber., 1989, 122, 1357; Högberg et al., J. Org. Chem., 1987, 52, 2033. Alternatively, ester (4) may be hydrolyzed using a suitable base, such as lithium hydroxide, in a suitable solvent or solvent mixture, such as dioxane and water, at a suitable temperature, such as room temperature or 50° C. to give acid (5). Other exemplary methods to hydrolyze esters that may be employed in the synthesis of acid (5) are well-known in the literature and described in March, Advanced Organic Chemistry, 4$^{th}$ Edition, John Wiley & Sons New York (1992), pp. 378-383. Amide (6) may be obtained by reacting acid (5) with a suitable activating agent, such as a mixture of 1-hydroxybenzotriazole and N,N'-dicyclohexylcarbodiimide, in presence of a suitable base, such as diisopropylethylamine, and HNR$^1$R$^2$ in a suitable solvent, such as N,N-dimethylformamide. Other methods that may be employed to form amide (6) by reacting HNR$^1$R$^2$ with acid (5) are well-known in the art and described in March, Advanced Organic Chemistry, 4$^{th}$ Edition, John Wiley & Sons New York (1992), pp. 419-421.

In some embodiments, compounds which inhibit or reduce the replication of negative-sense, single-stranded RNA viruses include, but are not limited to, compounds of formula A35, A35-1, A35-4, or A35-5 or pharmaceutically acceptable salts, hydrates, solvates, and prodrugs thereof. The compound of formula A35 (4-(4-bromophenyl)-N-methyl-N-(tetrahydro-1,1-dioxido-3-thienyl)-2-thiazolamine) can be obtained commercially from Aurora Fine Chemicals LLC, San Diego, USA (Order Number kcheb-095109) or Ryan Scientific Inc., Mt. Pleasant, USA (Order Number BAS13027502). The compound of formula A35-1 (N-methyl-4-(4-nitrophenyl)-N-(phenylmethyl)-2-thiazolamine) can be obtained commercially from Aurora Fine Chemicals LLC, San Diego, USA (Order Number kcheb-066010) or Ryan Scientific Inc., Mt. Pleasant, USA (Order Number LT01281147). The compound of formula A35-4 (4-[[4-(4-chlorophenyl)-1,3-thiazol-2-yl](methyl)amino]phenol) can be obtained commercially from ChemBridge Corporation, San Diego, USA (Order Number 7875580). The compound of formula A35-5 (4-(4-chlorophenyl)-N,N-dimethylthiazol-2-amine) can be obtained commercially from Ryan Scientific Inc., Mt. Pleasant, USA (Order Number AB-601/30966011).

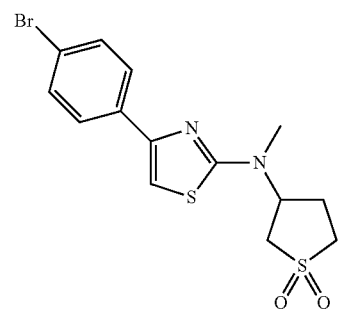

A35

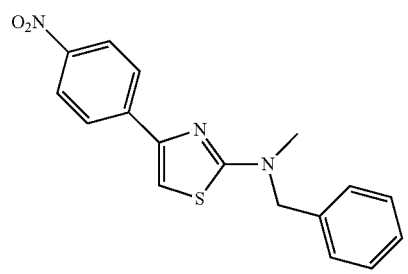

A35-1

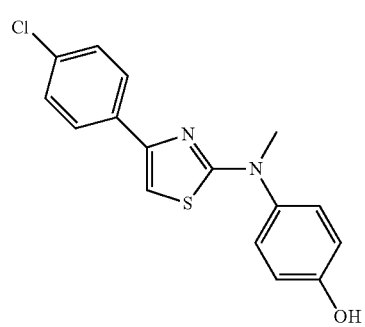

A35-4

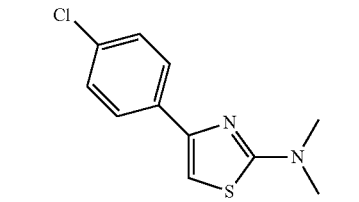

A35-5

In one embodiment, the virus is influenza virus, NDV, or VSV. In particular embodiments, the influenza virus is influenza A virus. In other embodiments, the influenza virus is influenza B virus. In some embodiments, the compound inhibits replication of influenza A virus but not influenza B virus. In some embodiments, the compound inhibits influenza A virus, but not influenza B virus, NDV or VSV. In some embodiments, the compound is a selective inhibitor of influenza A virus. In a particular embodiment, the negative-sense, single-stranded RNA virus is a segmented negative-sense, single-stranded RNA virus. In a specific embodiment, the virus is influenza A or B virus, parainfluenza virus or RSV. In one embodiment, the virus is not a rhabdovirus. In some embodiments, the negative-sense, single-stranded RNA virus is a non-segmented negative-sense, single-stranded RNA virus. In one embodiment, the virus is NDV or VSV.

In particular embodiments, compounds which inhibit or reduce the replication of negative-sense, single-stranded RNA viruses inhibit one or more of the following steps of the viral life cycle: viral entry, RNA replication, or RNA transcription. In a particular embodiment, the compound inhibits viral entry by endocytosis. In particular embodiments, the compounds inhibits entry of viruses that enter cells by endocytosis but not entry of viruses that enter cells by direct fusion with the plasma membrane. The effect of a compound on the different steps of the viral life cycle may be assayed using techniques known to one of skill in the art. RNA replication and transcription may be measured by measuring the replication and transcription of reporter gene product from an influenza virus mini-genome reporter construct, using, e.g., the assays disclosed herein. Such assays permit the identification of inhibitors of the viral polymerase or inhibitors of cellular proteins that are involved in viral RNA replication, translation or RNA trafficking. In some embodiments, the compound does not have an inhibitory effect on the overall host cell replication machinery, or has only a slight inhibitory effect compared to the effect on viral replication, as monitored by assays such as, e.g., the expression of a renilla luciferase reporter from a control plasmid (e.g., pGL3 described in Section 6 below).

In other embodiments, the inhibitors of the invention alter the kinetics of the viral cycle, e.g., the rate of viral replication or particle production is decreased. In some embodiments, the kinetic effect of a compound is measured by adding the compound to a cell at different times (e.g., before, concurrently with, or after) infection with a virus.

Accordingly, in certain embodiments, provided herein are methods for using one or more PKC inhibitors, sodium channel openers, calcium channel openers or $Na^+/K^+/ATPase$ pump inhibitors, including those set forth herein, for the inhibition or reduction of the replication of negative-sense, single-stranded segmented RNA viruses, including, but not limited to, influenza A or B virus, parainfluenza virus or RSV. In other embodiments, provided herein are methods for using one or more PKC inhibitors, sodium channel openers, calcium channel openers or $Na^+/K^+/ATPase$ pump inhibitors, including those set forth herein, for the inhibition or reduction of the replication of negative-sense, single-stranded segmented RNA viruses such as NDV or VSV. In other embodiments, provided herein are methods for using one or more of a compound with the formula A3-G, including, but not limited to, 2-(5-(2,3-dimethyl-1H-indol-5-yl)-1,3,4-oxadiazol-2-ylthio)-1-(pyrrolidin-1-yl)ethanone ("A3"); 2-(5-(2,3-dimethyl-1H-indol-5-yl)-1,3,4-oxadiazol-2-ylthio)-N,N-diethylacetamide ("A3-2"); 2-(5-(2,3-dimethyl-1H-indol-5-yl)-1,3,4-oxadiazol-2-ylthio)-1-(indolin-1-yl)ethanone ("A3-3"); 2-(5-(2,3-dimethyl-1H-indol-5-yl)-1,3,4-oxadiazol-2-ylthio)-N,N-diisopropylacetamide ("A3-4"); 2-(5-(2,3-dimethyl-1H-indol-5-yl)-1,3,4-oxadiazol-2-ylthio)-1-morpholinoethanone ("A3-5"); or 1-(azepan-1-yl)-2-(5-(2,3-dimethyl-1H-indol-5-yl)-1,3,4-oxadiazol-2-ylthio)ethanone ("A3-6") for the inhibition or reduction of the replication of negative-sense, single-stranded segmented RNA viruses, including, but not limited to, influenza A or B virus, parainfluenza virus, RSV, VSV or NDV. In other embodiments, provided herein are methods for using one or more of a compound with the formula A3 for the inhibition or reduction of the replication of negative-sense, single-stranded segmented RNA viruses, including, but not limited to, influenza A or B virus, parainfluenza virus, RSV, VSV or NDV. In other embodiments, provided herein are methods for using one or more of a compound with the formula A3-2, A3-3, A3-4, A3-5, or A3-6 for the inhibition or reduction of the replication of negative-sense, single-stranded segmented RNA viruses, including, but not limited to, influenza A or B virus, parainfluenza virus, RSV, VSV or NDV.

In other embodiments, provided herein are methods for using one or more of a compound with the formula 4-(4-bromophenyl)-N-methyl-N-(tetrahydro-1,1-dioxido-3-thienyl)-2-thiazolamine ("A35"); N-methyl-4-(4-nitrophenyl)-N-(phenylmethyl)-2-thiazolamine ("A35-1"); 4-[[4-(4-chlorophenyl)-1,3-thiazol-2-yl](methyl)amino]phenol ("A35-4"); or 4-(4-chlorophenyl)-N,N-dimethylthiazol-2-amine ("A35-5") for the inhibition or reduction of the replication of negative-sense, single-stranded segmented RNA viruses, including, but not limited to, influenza A or B virus, parainfluenza virus, RSV, VSV or NDV. In certain specific embodiments, provided herein are methods for using one or more of a compound with the formula A35 for the inhibition or reduction of the replication of negative-sense, single-stranded segmented RNA viruses, including, but not limited to, influenza A or B virus, parainfluenza virus, RSV, VSV or NDV.

In other embodiments, provided herein are methods for using one or more of a compound with the formula 9-(benzo[d][1,3]dioxol-5-yl)-4-hydroxy-6,7-dimethoxynaphtho[2,3-c]furan-1(3H)-one ("C2") for the inhibition or reduction of the replication of negative-sense, single-stranded segmented RNA viruses, including, but not limited to, influenza A or B virus, parainfluenza virus, RSV, VSV or NDV.

In certain of the above embodiments, the inhibitor is not a compound of the formula C2. In certain embodiments, the negative-sense, single-stranded RNA virus is an influenza virus. In certain embodiments, the negative-sense, single-stranded RNA virus is not VSV.

5.1.2 Enhancers of Viral Replication

In one embodiment, provided herein are compounds with activity as activators of PKC. Without being limited by theory, it is thought that compounds with activity as activators of PKC are useful for the enhancement of the replication of negative-sense, single-stranded RNA viruses and, accordingly, are useful for increasing replication of viral vaccine candidates in substrates for the propagation of viruses (e.g., tissue culture). Accordingly, provided herein are methods for using activators of PKC for the enhancement of the replication of negative-sense, single-stranded RNA viruses.

In a particular embodiment, compounds which have activity as activators of PKC include, but are not limited to, phorbol-12-myristate-13-acetate ("PMA"), mezerein, 12-Deoxyphorbol 13-acetate (Prostratin), 12-Deoxyphorbol 13-phenylacetate 20-acetate (dPPA, DOPPA) (PKCβ), Phorbol 12,13-dibutyrate, Phorbol 12,13-didecanoate, L-α-Phosphatidylinositol-3,4-bisphosphate.$5NH_3$ (PtdIns-3,4-$P_2$) (PKCδ, PKCε, PKCη), L-α-Phosphatidylinositol-3,4,5-trisphosphate.7Na (PtdIns-3,4,5-$P_3$) (PKCδ, PKCε, PKCη), DCP-LA (PKCε), (±)1,2-Didecanoylglycerol (10:0), (±)1,2-Dioleoylglycerol (18:1), Lipoxin $A_4$, 1-O-Hexadecyl-2-O-arachidonoyl-sn-glycerol, 1-Oleoyl-2-acetyl-sn-glycerol (OAG), N-(6-Phenylhexyl)-5-chloro-1-naphthalenesulfonamide, R 59022, R 59949, RHC-80267 (U-57908), 1-Stearoyl-2-arachidonoyl-sn-glycerol, 1-Stearoyl-2-linoleoyl-sn-glycerol, Bryostatin 1, Farnesyl Thiotriazole, Ingenol 3,20-dibenzoate, (−)-7-Octylindolactam V, SC-10, Thymeleatoxin (PKCα, PKCβI, PKCγ), and 1,2-dioctanoyl-sn-glycerol. Particular PKC isoforms or isotypes that certain compounds are useful for activating are set forth in parentheses following the compound name. In particular embodiments, the PKC activator is phorbol 12-myristate 13-acetate (PMA) or mezerein (Sigma-Aldrich, St. Louis, Mo., USA).

In one embodiment, provided herein are compounds with activity as sodium channel inhibitors or inhibitors of epithelial sodium channels. Without being limited by theory, it is thought that compounds with activity as sodium channel inhibitors or inhibitors of epithelial sodium channels are useful for the enhancement of the replication of negative-sense, single-stranded RNA viruses and, accordingly, are useful for increasing replication of viral vaccine candidates in substrates for the propagation of viruses (e.g., tissue culture). Accordingly, provided herein are methods for using sodium channel inhibitors or inhibitors of epithelial sodium channels for the enhancement of the replication of negative-sense, single-stranded RNA viruses.

In a particular embodiment, compounds which have activity as sodium channel inhibitors or inhibitors of epithelial sodium channels include, but are not limited to, amiloride derivatives. In a specific embodiment, compounds which have activity as sodium channel inhibitors or inhibitors of epithelial sodium channels include, but are not limited to, phenamil, 2',4'-dichlorobenzamil, 3',4'-dichlorobenzamil, 5-(N,N-Dimethyl)amiloride.HCl, 5-(N,N-Hexamethylene)amiloride, 5-(N-Ethyl-N-isopropyl)amiloride, 5-(N-Methyl-N-isobutyl)amiloride, Amiloride.HCl, ATX II (recombinant), BIA 2-093, Benzamil.HCl, Bupivacaine, Carbamazepine, μ-Conotoxin GIIIB, Disopyramide, Flecainide acetate salt, Kavain (+/−), KR-32568, Lamotrigine, Lappaconitine.HBr, Lidocaine, Metolazone, Mexiletine.HCl, PD-85639, Phenamil methanesulfonate salt, Procainamide, Procaine, QX-314, R(−)-Me5.HCl, Riluzole, Tetrodotoxin, and Tocainide.HCl. In particular embodiments, the sodium channel inhibitor is phenamil or 3',4'-dichlorobenzamil (Sigma-Aldrich, St. Louis, Mo., USA) or 2',4'-dichlorobenzamil (BIOMOL International, L.P., Plymouth Meeting, Pa., USA).

It should be noted that in contrast to the present findings, amiloride derivatives have been reported to inhibit the replication of several RNA viruses such as human immunodeficiency virus (HIV-1) (Ewart, G. D., Mills, K., Cox, G. B. and Gage, P. W. (2002) Amiloride derivatives block ion channel activity and enhancement of virus-like particle budding caused by HIV-1 protein Vpu. *Eur. Biophys. J.* 31(1): 26-35), human rhinovirus (Gazina, E. V., Harrison, D. N., Jefferies, M., Tan, H., Williams, D., Anderson, D. A. and Petrou, S. (2005) Ion transport blockers inhibit human rhinovirus 2 release. *Antiviral Res.* 67(2): 98-106), coxsackievirus (Harrison, D. N., Gazina, E. V., Purcell, D. F., Anderson, D. A. and Petrou, S. (2008) Amiloride derivatives inhibit coxsackievirus B3 RNA replication. *J. Virol.* 82(3): 1465-73) and coronaviruses (Wilson L., Gage P. and Ewart G. (2006) Hexamethlene amiloride blocks E protein ion channels and inhibits coronavirus replication. Virology 353(2):294-306).

In one embodiment, provided herein are compounds with activity as calcium channel inhibitors. Without being limited by theory, it is thought that compounds with activity as calcium channel inhibitors are useful for the enhancement of the replication of negative-sense, single-stranded RNA viruses and, accordingly, are useful for increasing replication of viral vaccine candidates in substrates for the propagation of viruses (e.g., tissue culture). Accordingly, provided herein are methods for using calcium channel inhibitors for the enhancement of the replication of negative-sense, single-stranded RNA viruses.

In a particular embodiment, compounds which have activity as calcium channel inhibitors include, but are not limited to, ω-Agatoxin TK, Amiloride.HCl, Amlodipine, 2-APB, Calciseptine, Cilnidipine, ω-Conotoxin GVIA, ω-Conotoxin MVIIC, 2',4'-Dichlorobenzamil.HCl, Diltiazem.HCl, L-cis-Diltiazem.HCl, Felodipine, Flunarizine.2HCl, Gabapentin, Isradipine, Kurtoxin (e.g., recombinant Kurtoxin), Nifedipine, Niguldipine.HCl, Nimodipine, Nitrendipine, SDZ-202 791 R(−), SK&F 96365, SNX-482, Tetrandrine, and Verapamil HCl. In certain embodiments, the calcium channel inhibitor is Amiloride.HCl (Sigma-Aldrich, St. Louis, Mo., USA) or 2',4'-Dichlorobenzamil.HCl (BIOMOL, Plymouth Meeting, Pa., USA).

In a particular embodiment, compounds which enhance the replication of negative-sense, single-stranded RNA viruses include, but are not limited to amiloride derivatives, PMA, mezerein, 12-Deoxyphorbol 13-acetate (Prostratin), 12-Deoxyphorbol 13-phenylacetate 20-acetate (dPPA, DOPPA), Phorbol 12,13-dibutyrate, Phorbol 12,13-didecanoate, L-α-Phosphatidylinositol-3,4-bisphosphate.5NH$_3$ (PtdIns-3,4-P$_2$), L-α-Phosphatidylinositol-3,4,5-trisphosphate.7Na (PtdIns-3,4,5-P$_3$), DCP-LA, (±)1,2-Didecanoylglycerol (10:0), (±)1,2-Dioleoylglycerol (18:1), Lipoxin A$_4$, 1-O-Hexadecyl-2-O-arachidonoyl-sn-glycerol, 1-Oleoyl-2-acetyl-sn-glycerol (OAG), N-(6-Phenylhexyl)-5-chloro-1-naphthalenesulfonamide, R 59022, R 59949, RHC-80267 (U-57908), 1-Stearoyl-2-arachidonoyl-sn-glycerol, 1-Stearoyl-2-linoleoyl-sn-glycerol, Bryostatin 1, Farnesyl Thiotriazole, Ingenol 3,20-dibenzoate, (−)-7-Octylindolactam V, SC-10, Thymeleatoxin, phenamil, 2',4'-dichlorobenzamil, 3',4'-dichlorobenzamil, 5-(N,N-Dimethyl)amiloride.HCl, 5-(N,N-Hexamethylene)amiloride, 5-(N-Ethyl-N-isopropyl)amiloride, 5-(N-Methyl-N-isobutyl)amiloride, Amiloride.HCl, ATX II (recombinant), BIA 2-093, Benzamil.HCl, Bupivacaine, Carbamazepine, μ-Conotoxin GIIIB, Disopyramide, Flecainide acetate salt, Kavain (+/−), KR-32568, Lamotrigine, Lappaconitine.HBr, Lidocaine, Metolazone, Mexiletine.HCl, PD-85639, Phenamil methanesulfonate salt, Procainamide, Procaine, QX-314, R(−)-Me5.HCl, Riluzole, Tetrodotoxin, Tocainide.HCl, HNMPA-(AM)$_3$, AG-1296, and Paclitaxel.

In a specific embodiment, compounds which enhance the replication of negative-sense, single-stranded RNA viruses include, but are not limited to EHNA, HNMPA-(AM)3, AG-1296, phenamil, Amiloride.HCl, 2',4'-dichlorobenzamil, 3',4'-dichlorobenzamil, and Phenamil methanesulfonate salt.

In a particular embodiment, the negative-sense, single-stranded RNA virus is a segmented negative-sense, single-stranded RNA virus. In another embodiment, the negative-sense, single-stranded RNA virus is a non-segmented negative-sense, single-stranded RNA virus. In a specific embodiment, the negative-sense, single-stranded RNA virus is influenza virus A or B, parainfluenza virus, measles virus, mumps virus or RSV.

Accordingly, in certain embodiments, provided herein are methods for using one or more PKC activators, sodium channel inhibitors or calcium channel inhibitors, including those set forth herein, for the enhancement of the replication of negative-sense, single-stranded segmented RNA viruses, including, but not limited to, influenza A or B virus, parainfluenza virus, measles virus, mumps virus or RSV. In other embodiments, provided herein are methods for using one or more PKC activators, sodium channel inhibitors or calcium channel inhibitors, including those set forth herein, for the enhancement of the replication of negative-sense, single-stranded segmented RNA viruses, including, NDV or VSV.

Illustrative amiloride derivatives include, but are not limited to, compounds of the formula:

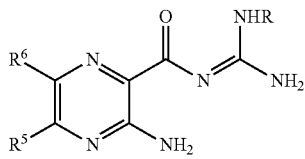

and pharmaceutically acceptable salts, hydrates, solvates, prodrugs and stereoisomers thereof, wherein:
R is H, phenyl, or a substituted or unsubstituted alkyl group;
$R^5$ is H or a substituted or unsubstituted amino group; and
$R^6$ is H or halogen.
Further illustrative amiloride derivatives include, but are not limited to, compounds of the formula:

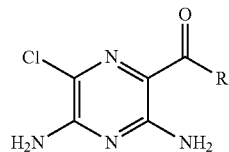

and pharmaceutically acceptable salts, hydrates, solvates, prodrugs and stereoisomers thereof, wherein:
R is hydroxy, a substituted or unsubstituted guanidino group, or a thiourea group.

Compounds of the formulas set forth above can be made by one skilled in the art using commercially available reagents.

In a particular embodiment, an amiloride analog is a compound disclosed in Kleyman and Cragoe, 1988, "Amiloride and Its Analogs as Tools in the Study of Ion Transport," *J. Membrane Biol.* 105:1-21, which is incorporated by reference herein in its entirety.

Illustrative examples of calcium channels that compounds set forth herein are useful for inhibiting or activating include, but are not limited to, N-type, L-type, P-type, Q-type, R-type and T-type. A representative compound that modulates N-type calcium channels is ω-Conotoxin GVIA. Representative compounds that modulate L-type calcium channels include, but are not limited to FPL-64176, Amlodipine, Calciseptine, Diltiazem.HCl, Felodipine, FPL-64176, Gabapentin, Isradipine, Nifedipine, Niguldipine.HCl, SDZ-202 791 R(−), and Verapamil HCl. A representative compound that modulates P-type calcium channels is ω-Agatoxin TK. A representative compound that modulates R-type calcium channels is SNX-482. Representative compounds that modulate T-type calcium channels include, but are not limited to Amiloride.HCl, Flunarizine.2HCl, and Kurtoxin (e.g., recombinant Kurtoxin). A dual L-type and N-type calcium channel inhibitor is Cilnidipine. A dual N-type and Q-type calcium channel inhibitor is ω-Conotoxin MVIIC. A dual L-type and T-type calcium channel inhibitor is Tetrandrine.

5.2 Screening Assays for Compounds that Modulate Virus Replication

The present invention provides high throughput screening assays for the identification of compounds that modulate the replication of negative-sense, single-stranded RNA viruses. In some embodiments, the high throughput screening assays involve the use of mini-genome reporter constructs comprising a reporter gene flanked by the 3' and 5' incorporation signals which are required for proper replication, transcription, and packaging of the negative-sense, single-stranded RNA virus RNA to identify compounds that modulate viral replication, in particular the replication of the viral genome and/or the production of viral proteins. The mini-genome reporter construct is transfected into cells, the cells are infected with a negative-sense, single-stranded RNA virus, and the expression or activity of a reporter gene product is measured as a means of determining viral replication. Alternatively, the cells are infected with a negative-sense, single-stranded RNA virus, transfected with the mini-genome reporter construct, and expression or activity of a reporter gene product is measured. In a specific embodiment, the mini-genome reporter construct comprises a reporter gene flanked by the 3' and 5' signals which are required for proper transcription by RNA polymerase I and recognition and transcription by the negative-sense, single-stranded RNA virus polymerase. The cells can be infected with different MOIs (e.g., 0.001, 0.005, 0.01, 0.05, 0.1, 0.5, 1, 2.5, or 5) and the effect of compounds can be assessed in the screening assays. The effect of different concentrations of the compounds can also be assessed using in the screening assays. The expression or activity of a reporter gene product can be measured at different times post-infection. For example, the expression or activity of a reporter gene product may be measured 6 hours, 12 hours, 16 hours, 24 hours, 48 hours or 72 hours post-infection. A compound that increases viral replication will increase the expression or activity of the reporter gene product relative to a negative control. In contrast, a compound that decreases viral replication will decrease the expression or activity of the reporter gene product relative to a negative control.

In a specific embodiment, the high throughput screening assay to identify a compound that modulates the replication of a negative-sense, single-stranded RNA virus comprises: (a) contacting a compound or a member of a library of compounds with a cell transfected with a mini-genome reporter construct, wherein the mini-genome reporter construct comprises a reporter gene flanked by the 3' and 5' signals which are required for proper transcription by RNA polymerase I and recognition and transcription by the negative-sense, single-stranded RNA virus polymerase; (b) infecting the cell with a negative-sense, single-stranded RNA virus in the presence of the compound; and (c) measuring the expression or activity of a reporter gene product. In certain embodiments, the cell is infected with the negative-sense, single-stranded RNA virus 5 seconds, 15 seconds, 1 minute, 5 minutes, 15 minutes, 30 minutes, 1 hour, 2 hours, 6 hours, 12 hours, 16 hours or 24 hours after the cell is contacted with the compound or library of compounds. In another embodiment, the high throughput screening assays comprise: (a) infecting the cell with a negative-sense, single-stranded RNA virus in the presence of a compound or a member of a library of compounds, wherein the cell is transfected with a mini-genome reporter construct, and the mini-genome reporter construct comprises a reporter gene flanked by the 3' and 5' signals which are required for proper transcription by RNA polymerase I and recognition and transcription by the negative-sense, single-stranded RNA virus polymerase; and (b) measuring the expression or activity of a reporter gene product. In certain embodiments, the cell is infected with the negative-sense, single-stranded RNA virus 5 seconds, 15 seconds, 1 minute, 5 minutes, 15 minutes, 30 minutes, 1 hour, 2 hours, 6 hours, 12 hours, 16 hours or 24 hours after transfection of the mini-genome reporter construct. In certain embodiments, the cell is infected with the virus 5 seconds, 15 seconds, 1 minute, 5 minutes, 15 minutes, 30 minutes, 1 hour, 2 hours, 6 hours, 12 hours, 16 hours or 24 hours after the cell is contacted with the compound or library of compounds. In certain embodiments, the cell is contacted with the compound or library of compound 5 seconds, 15 seconds, 1 minute, 5 minutes, 15 minutes, 30 minutes, 1 hour, 2 hours, 6 hours, 12 hours, 16 hours or 24 hours after the cell is infected with the negative-sense, single-stranded RNA virus. In another embodiment, the high throughput screening assays comprise: (a) infecting a cell transfected with a mini-genome reporter construct with a negative-sense single-stranded RNA virus, wherein the mini-genome reporter construct comprises a reporter gene flanked by the 3' and 5' signals which are required for proper transcription by RNA polymerase I and recognition and transcription by the negative-sense, single-stranded RNA virus polymerase; (b) contacting the cell with the compound or library of compounds; and (c) measuring the expression or activity of a reporter gene product. In certain embodiments, the cell is contacted with the compound or library of compound 5 seconds, 15 seconds, 1 minute, 5 minutes, 15 minutes, 30 minutes, 1 hour, 2 hours, 6 hours, 12 hours, 16 hours or 24 hours after infection with the negative-sense, single-stranded RNA virus.

In another embodiment, the high throughput screening assay to identify a compound that modulates the replication of a negative-sense, single-stranded RNA virus comprises: (a) contacting a compound with a cell infected with a negative-sense, single-stranded RNA virus that is engineered to express a reporter gene; and (b) measuring the expression or activity of a reporter gene product.

In some embodiments, the high throughput screening assays involve: (a) contacting a compound or a member of a library of compounds with a cell before (e.g., 15 minutes, 30 minutes, 1 hour, 2 hours, 4 hours, 6 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection with a negative-sense, single-stranded RNA virus, wherein the genome of the negative-sense, single-stranded RNA virus is engineered to express a reporter gene; and (b) measuring the expression or activity of a reporter gene product. The cells can be infected with different MOIs (e.g., 0.001, 0.005, 0.01, 0.05, 0.1, 0.5, 1, 2.5, or 5) and the effect of compounds can be assessed in the screening assays. The effect of different concentrations of the compounds can also be assessed using in the screening assays. The expression or activity of a reporter gene product can be measured at different times post-infection. For example, the expression or activity of a reporter gene product may be measured 6 hours, 12 hours, 16 hours, 24 hours, 48 hours or 72 hours post-infection. A compound that increases the replication of a negative-sense, single-stranded RNA virus is identified if the expression or activity of the reporter gene product is increased in the cell contacted with the compound relative to the expression or activity of the reporter gene product in a cell contacted with a negative control. In contrast, a compound that decreases the replication of a negative-sense, single-stranded RNA virus is identified if the expression or activity of the reporter gene product is decreased in the cell contacted with the compound relative to the expression or activity of the reporter gene product in a cell contacted with a negative control.

In one embodiment, the high throughput assay for screening for compounds that modulate the replication of a negative-sense, single-stranded RNA virus comprises: (a) contacting a cell with a negative-sense, single-stranded RNA virus and a compound or a member of a library of compounds, wherein the genome of the negative-sense, single-stranded RNA virus is engineered to express a reporter gene; and (b) measuring expression or activity of a reporter gene product, wherein a compound that modulates the replication of the virus is identified if the expression or activity of the reporter gene product is altered in the cell contacted with the compound relative to the expression or activity of the reporter gene product in a cell contacted with a negative control. In another embodiment, the high throughput assay for screening for compounds that modulate the replication of a negative-sense, single-stranded RNA virus comprises: (a) contacting a compound or a member of a library of compounds with a cell infected with a negative-sense, single-stranded RNA virus, wherein the genome of the negative-sense, single-stranded RNA virus is engineered to express a reporter gene; and (b) measuring expression or activity of a reporter gene product, wherein a compound that modulates the replication of the virus is identified if the expression or activity of the reporter gene product is altered in the cell contacted with the compound relative to the expression or activity of the reporter gene product in a cell contacted with a negative control. In accordance with these embodiments, a compound that increases virus replication is identified if the expression or activity of the reporter gene product is increased in the cell contacted with the compound relative to the expression or activity of the reporter gene product in a cell contacted with a negative control. In contrast, and in accordance with these embodiments, a compound that decreases virus replication is identified if the expression or activity of the reporter gene product is decreased in the cell contacted with the compound relative to the expression or activity of the reporter gene product in a cell contacted with a negative control.

In another embodiment, the high throughput assay for screening for compounds that modulate the replication of a negative-sense, single-stranded RNA virus comprises: (a) contacting a compound or a member of a library of compounds with a cell; (b) infecting the cell with a negative-sense, single-stranded RNA virus in the presence of the compound, wherein the genome of the negative-sense, single-stranded RNA virus is engineered to express a reporter gene; and (c) measuring expression or activity of a reporter gene product, wherein a compound that modulates the replication of the virus is identified if the expression or activity of the reporter gene product is altered in the cell contacted with the compound relative to the expression or activity of the reporter gene product in a cell contacted with a negative control. In yet another embodiment, the high throughput assay for screening for compounds that modulate the replication of a negative-sense, single-stranded RNA virus comprises: (a) infecting a cell with a negative-sense, single-stranded RNA virus engineered to contain a reporter gene; (b) contacting the infected cell with a compound or a member of a library of compounds; and (c) measuring expression or activity of a reporter gene product, wherein a compound that modulates the replication of the virus is identified if the expression or activity of the reporter gene product is altered in the cell contacted with the compound relative to the expression or activity of the reporter gene product in a cell contacted with a negative control. In accordance with these embodiments, a compound that increases virus replication is identified if the expression or activity of the reporter gene product is increased in the cell contacted with the compound relative to the expression or activity of the reporter gene product in a cell contacted with a negative control. In contrast, and in accordance with these embodiments, a compound that decreases virus replication is identified if the expression or activity of the reporter gene product is decreased in the cell contacted with the compound relative to the expression or activity of the reporter gene product in a cell contacted with a negative control.

In some embodiments of the invention, an embryonated egg or any other substrate that permits the replication of negative-sense, single-stranded RNA viruses may be used in place of the cells used in the high throughput screening assays described herein.

In a specific embodiment, the cell(s) used in the high throughput assay for screening for compounds that modulate replication of a negative-sense, single-stranded RNA virus is a cell(s) that permits infection with and replication of the negative-sense, single-stranded RNA virus. In some embodiments, the high throughput assay for screening for compounds that modulate replication of a negative-sense, single-stranded RNA virus uses any substrate that allows the virus to grow to titers that permit the use of such substrate/virus combinations in the screening assays. By way of non-limiting example, substrates useful in the high throughput screening assays of the invention include cells (e.g. avian cells, chicken cells (e.g., primary chick embryo cells or chick kidney cells), Vero cells, MDCK cells, human respiratory epithelial cells (e.g., A549 cells), calf kidney cells, mink lung cells, etc.) that are susceptible to infection by the viruses or embryonated eggs or animals (e.g., birds). In one embodiment, the cells used in the high throughput screening assay are biologically relevant to the type of infection.

In a specific embodiment, the reporter gene product measured in the high throughput screening assays described above is an RNA product. In another embodiment, the reporter gene product measured in the high throughput screening assays described above is a protein product. In another embodiment, the activity of a reporter gene product is measured in the high throughput screening assays described above and the reporter gene product is protein.

Any method known to one of skill in the art can be used measure the expression or activity of a reporter gene product. In one embodiment, the reporter gene product is RNA and a technique known to one of skill in the art, such as RT-PCR or Northern blot analysis, is used to measure the expression of the RNA product. In another embodiment, the reporter gene product is protein and a technique known to one of skill in the art, such as western blot analysis or an ELISA, is used to measure the expression of the protein product. In another embodiment, the reporter gene product is protein and the activity of the protein is measured using a technique known to one of skill in the art.

Any screening assay described herein can be performed individually, e.g., just with the test compound, or with appropriate controls. For example, a parallel assay without the test compound, or other parallel assays without other reaction components (e.g., virus) can be performed. In one embodiment, a parallel screening assay as described above is performed except that a negative control and/or a positive control are used in place of a test compound. In another embodiment, to eliminate cytotoxic compounds that appear as false positives, a counter screen is performed in which uninfected cells are transfected with a nucleic acid construct (e.g., a plasmid) comprising a reporter gene and the expression or activity of a reporter gene product is measured. Alternatively, it is possible to compare assay results to a reference, e.g., a reference value, e.g., obtained from the literature, a prior assay, and so forth. Appropriate correlations and art known statistical methods can be used to evaluate an assay result.

In some embodiments, the average expression or activity of the reporter gene product when a negative control (e.g., PBS) is contacted with cell is determined and the percent expression or activity of the reporter gene product for each compound is determined in relation to this internal control. In one embodiment, the average percent expression or activity of the reporter gene product is calculated and the compounds are classified as strong or medium inhibitors of virus replication based on a 90% to 100% or 70% to 89% reduction in the expression or activity of the reporter gene product, respectively. In another embodiment, the compounds are classified as enhancers of viral replication if at least a 2 fold increase in the expression or activity of a reporter gene product above the negative control is obtained.

In some embodiments, the average percent expression or activity of the reporter gene product when a negative control (e.g., PBS) is contacted with cells transfected with a nucleic acid construct (e.g., a plasmid) comprising a reporter gene is calculated and those compounds that have a 20% to 30% reduction in the expression or activity of the reporter gene product are considered cytotoxic to the cells. In other embodiments, the average percent expression or activity of the reporter gene product when a negative control (e.g., PBS) is contacted with cells transfected with a nucleic acid construct comprising a reporter gene is calculated and those compounds that have a 50% or greater reduction in the expression or activity of the reporter gene product are considered cytotoxic to the cells.

In certain embodiments, to eliminate false positives, such as cytotoxic compounds that appear as inhibitors, a counter screen is performed in which uninfected cells are transfected with a nucleic acid construct (e.g., a plasmid) comprising a reporter gene and the expression or activity of a reporter gene product is measured. In certain embodiments, the reporter gene product is renilla luciferase expressed from, e.g., a plasmid such as pGL3 (described in Section 6 below). In certain embodiments, compounds initially classified as enhancers of virus replication that also enhance expression or activity of a reporter gene product in the counter screen are eliminated as false positives. In other embodiments, compounds initially classified as inhibitors of virus replication that cause a reduction in reporter gene product expression or activity of greater than 20-30% in the counter screen are defined as a false positives and eliminated from further analysis. In certain embodiments, this threshold is decreased to 50% in cases where a compound causes a >95% reduction of reporter gene expression or activity in the screening assay.

5.2.1 Construction of Mini-Genome Reporter Construct and Viruses with a Genome Comprising a Reporter Gene With respect to segmented, negative-sense, single-stranded RNA viruses, a recombinant segment comprising a reporter gene and the 3' and 5' incorporation signals which are required for proper replication, transcription and packaging of the viral RNAs can be generated. In a specific embodiment, the recombinant segment is a chimeric segment comprising a reporter gene, the coding sequence of a viral gene or a fragment thereof, and the 3' and 5' incorporation signals which are required for proper replication, transcription, and packaging of the viral RNA. Techniques for producing chimeric segments are described in, e.g., International Publication No. WO 2007/064802, published Jun. 7, 2007, which is incorporated herein by reference in its entirety. In another embodiment, the recombinant segment comprises the coding region of a reporter gene, an IRES, the coding region of a viral gene, and the 3' and 5' incorporation signals which are required for proper replication, transcription, and packaging of the viral RNA. Examples of such bicistronic segments are described in, e.g., International Publication No. WO 2007/064802. In one embodiment, the recombinant segment may be used as a mini-genome reporter construct in the screening assays described above. In another embodiment, the recombinant segment can be used to generate a segmented, negative-sense, single-stranded RNA virus containing such a segment and the virus can be used in the screening assays described above.

With respect to non-segmented, negative-sense, single-stranded RNA viruses, in one embodiment, a mini-genome reporter construct comprising a reporter gene and the 3' and 5' incorporation signals which are required for proper replication, transcription, and packaging of the viral RNA can be generated. In another embodiment, a recombinant genome comprising the nucleic acid sequence of a reporter gene can be engineered into the viral genome to generate a reporter virus, and such a virus can be used in the screening assays described above.

In some embodiments, the mini-genome reporter construct comprises a reporter gene, wherein the reporter gene is flanked by the 3' and 5' signals which are required for proper transcription by RNA polymerase I and recognition and transcription by the negative-sense, single-stranded RNA virus polymerase. In one embodiment, the mini-genome reporter construct comprises a cassette containing the coding region of a reporter gene inserted in the reverse orientation and complementary sense between the virus non-coding regions which serve as the viral promoter. In a specific embodiment, the cassette is flanked by a human RNA polymerase I (Pol I) promoter and a hepatitis delta virus (HDV) ribozyme. The transcribed RNA (vRNA) has exact ends and mimics a non-segmented, negative sense virus genome segment. Upon infection, the viral polymerase recognizes the promoter and the reporter gene is transcribed and expressed. In one embodiment, the mini-genome reporter construct mimics a segment of a segmented, negative-sense, single-stranded RNA virus. In another embodiment, the mini-genome reporter construct comprises the reporter gene, the flanking elements (Pol I promoter and HDV ribozyme), and all the viral genes required for virus replication in a single plasmid.

The reporter gene can be any nucleotide sequence encoding a protein that is readily detectable either by its presence or activity. Reporter genes may be obtained and the nucleotide sequence of the reporter gene determined by any method well-known to one of skill in the art. Examples of reporter genes include, but are not limited to, luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase beta-glucoronidase, beta-lactamase, chloramphenicol acetyltransferase ("CAT"), and alkaline phosphatase ("AP"). The characteristics and methods for using the aforementioned reporter genes are described in U.S. Patent Application Publication No.: US 2007/0111203 A1, the disclosure of which is incorporated by reference in its entirety. In a specific embodiment, a reporter gene utilized is easily assayed and has an activity which is not normally found in the cell or organism of interest. In another specific embodiment, the reporter is luciferase.

Negative-sense, single-stranded RNA viruses with a genome comprising a reporter gene can be engineered using any technique known to one of skill in the art. Techniques such as reverse genetics and helper-free plasmid rescue can be used to generate negative-sense, single-stranded RNA viruses with a genome comprising a reporter gene. The reverse genetics technique involves the preparation of synthetic recombinant viral RNAs that contain the non-coding regions of the negative-strand, viral RNA which is essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a negative-sense, single-stranded RNA with a genome comprising a reporter gene. Briefly, with respect to influenza virus, full length cDNAs of viral segments are amplified using PCR with primers that include unique restriction sites, which allow the insertion of the PCR product into the a plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment or minimal viral segments as well as expression vectors comprising necessary viral proteins required for replication of the virus are transfected into cells leading to production of recombinant viral particles. In one embodiment, a mini-genome reporter construct is also, or in place of one of the viral segments not required for replication of the virus, transfected into the cells, wherein the mini-genome reporter construct comprises a reporter gene flanked by the 3' and 5' incorporation signals which are required for proper replication, transcription, and packaging of the viral RNA, such as a Pol I promoter and HDV ribozyme. This mini-genome reporter construct may be transfected into cells leading to production of recombinant viral particles. For a detailed description of helper-free plasmid technology see, e.g., International Publication No. WO 01/04333; U.S. Pat. No. 6,649,372; Fodor et al., 1999, J. Virol. 73:9679-9682; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties. Similarly, with respect to the single segment genome, a complete cDNA of a virus strain can be constructed, inserted into a plasmid vector and engineered to containing a unique restriction site. The reporter gene may then be inserted into the viral genome at the unique restriction site. The single segment may be positioned between a T7 promoter and the hepatitis delta virus ribozyme to produce an exact negative transcript from the T7 polymerase. The plasmid vector and expression vectors comprising the necessary viral proteins are transfected into cells leading to production of recombinant viral particles (see Swayne et al., 2003, Avian Dis. 47:1047-1050 and Swayne et al., 2001, J. Virol. 11868-11873, each of which is incorporated by reference in its entirety).

Negative-sense, single-stranded RNA viruses with a genome comprising a reporter gene can be propagated in any substrate that allows the virus to grow to titers that permit the uses of such viruses in the screening assays. For example, the viruses may be grown in cells (e.g. avian cells, chicken cells (e.g., primary chick embryo cells or chick kidney cells), Vero cells, MDCK cells, human respiratory epithelial cells (e.g., A549 cells), calf kidney cells, mink lung cells, etc.) that are susceptible to infection by the viruses, embryonated eggs or animals (e.g., birds). The virus may be removed from cell culture and separated from cellular components, typically by well known clarification procedures, e.g., such as gradient centrifugation and column chromatography, and may be further purified as desired using procedures well known to those skilled in the art, e.g., plaque assays.

5.2.2 Compounds

Compounds to be tested for replication modulation activity can be obtained from any source. Any compound can be screened, either individually, in groups, or in high throughput format, in connection with the assays described herein. Such compounds include, but are not limited to, proteins, polypeptides, peptides, nucleic acids, including dominant negative mutants, antisense, ribozyme or triple helix molecules, antibodies, small organic molecules, inorganic molecules. In a specific embodiment, small molecular weight compounds are used.

In accordance with the present invention, the compounds to be assayed may be provided to the assay system as an isolated compound or, in another embodiment, the compound may be provided to the assay system as part of a composition.

Combinatorial chemical libraries or ligand libraries may be screened in one or more assays, as described in Section 5.2 herein, to identify those library members (particular chemical species or subclasses) that display a desired characteristic activity. The compounds thus identified can serve as conventional "lead compounds" or can themselves be used as potential or actual therapeutics or for enhancing the growth of viruses in substrates, e.g., cells.

Preparation and screening of combinatorial chemical libraries is well known to those of skill in the art. Such combinatorial chemical libraries include, but are not limited to, peptide libraries (See, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (See Ausubel, Berger and Sambrook, all supra), peptide nucleic acid libraries (See, e.g., U.S. Pat. No. 5,539,083), antibody libraries (See, e.g., Vaughn et al., Nature Biotechnology, 14(3):309-314 (1996) and PCT/US96/10287), carbohydrate libraries (See, e.g., Liang et al., Science, 274:1520-1522 (1996) and International Patent Application Publication NO. WO 1997/000271), small organic molecule libraries (See, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework). Examples of lead compounds which can be used as starting molecules for library generation include, e.g., those described in Section 5.1 above.

Devices for the preparation of combinatorial libraries are commercially available (See, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (See, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.). The test compounds can also be obtained from: biological libraries; peptoid libraries (libraries of molecules having the functionalities of peptides, but with a novel, non-peptide backbone which are resistant to enzymatic degradation but which nevertheless remain bioactive; See, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library). Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.). Enzymes can be screened for identifying compounds which can be selected from a combinatorial chemical library or any other suitable source (Hogan, Jr., Nat. Biotechnology 15:328, 1997).

In some embodiments, the compounds modulate PKC activity. In one embodiment, the compounds modulate one or more of the PKC isoforms identified in Section 5.1 above. In a specific embodiment, the compounds are PKC inhibitors. In an alternative embodiment, the compounds are PKC activators.

In other embodiments, the compounds modulate sodium channel activity. In one embodiment, the compounds modulate one or more of the sodium channels identified in Section 5.1 above. In a specific embodiment, the compounds are sodium channel openers. In an alternative embodiment, the compounds are sodium channel inhibitors.

In some other embodiments, the compounds modulate calcium channel activity. In one embodiment, the compounds modulate one or more of the calcium channels identified in Section 5.1 above. In a specific embodiment, the compounds are calcium channel openers. In an alternative embodiment, the compounds are calcium channel inhibitors. In other embodiments, the compounds modulate the activity of a Na+/K+/ATPase pump. In other embodiments, the compounds modulate sodium/calcium exchange.

5.3 Biological Assays

5.3.1 Cellular Assays for Assessing the Effect of a Compound on Viral Replication Compounds identified in the high throughput assay can be further assessed for their effects on viral replication or the effects of the compounds on viral replication can be confirmed by measuring viral replication. Alternatively, the effect of a compound can be assessed by measuring viral replication without running a high throughput assay described in Section 5.2, supra. Such assays involve: (a) contacting a compound or a member of a library of compounds with a cell before (e.g., 15 minutes, 30 minutes, 1 hour, 2 hours, 4 hours, 6 hours, 12 hours, 16 hours, 24 hours or more before), concurrently and/or subsequent to (e.g., 15 minutes, 30 minutes, 1 hour, 2 hours, 4 hours, 6 hours, 12 hours, 16 hours, 24 hours or more after) infection with a negative-sense, single-stranded RNA virus; and (b) measuring virus replication. The cells can be infected at different MOIs and the effect of a compound on virus replication can be assessed. For example, the MOIs may be 0.001, 0.005, 0.01, 0.05, 0.1, 0.5, 1, 2.5, or 5. The effect of different concentrations of a compound on virus replication can also be assessed. The cells or other substrate that contains cells (e.g., embryonated eggs) used in the assay should be susceptible to infection by the chosen negative-sense, single-stranded RNA virus. The cells may be primary cells or established cell lines. With respect to influenza virus, for example, the following cells may be used in the assay: chicken cells (e.g., primary chick embryo cells or chick kidney cells), Vero cells, MDCK cells, human respiratory epithelial cells (e.g., A549 cells), calf kidney cells, and mink lung cells. In one embodiment, the cells used to assess the effect of a compound on virus replication are selected from the following cells or cell lines: MEF, 293T, Huh 7.5, Detroit, and human tracheobronchial epithelial (HTBE; primary lung cells) cells. In one embodiment, the cell or cell line is biologically relevant to virus infection.

Virus replication can be measured at different times post-infection. For example, virus replication may be measured 6 hours, 12 hours, 16 hours, 24 hours, 48 hours or 72 hours post-infection. Any method known to one of skill in the art can be used measure virus replication. For example, viral replication may be assessed by measuring viral titer (as determined, e.g., by plaque formation), the production of viral proteins (as determined, e.g., by western blot analysis, ELISA or flow cytometry), or the production of viral nucleic acids (as determined, e.g., by RT-PCR or Northern blot analysis) using techniques known to one of skill in the art. See Sections 5.3.1.1-5.3.1.6 below for more details of techniques for measuring viral replication.

In the assays described above, a compound that increases the replication of a negative-sense, single-stranded RNA virus is identified if the replication of the virus is increased in the cell contacted with the compound relative to the replication of the virus in a cell contacted with a negative control (e.g., PBS or saline). In contrast, a compound that decreases the replication of a negative-sense, single-stranded RNA virus is identified if the replication of the virus is decreased in the cell contacted with the compound relative to the replication of the virus in a cell contacted with a negative control (e.g., PBS or saline).

In certain embodiments, an inhibitor of viral replication is identified if a compound reduces the virus replication by at least 1.5 fold, 2 fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In certain embodiments, an inhibitor of viral replication is identified if a compound reduces the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, an inhibitor of viral replication is identified if a compound reduces the virus replication by approximately 2 logs or more, approximately 3 logs or more, approximately 4 logs or more, approximately 5 logs or more, or 2 to 10 logs or 2 to 5 logs relative to virus replication in the absence of compound or the presence of a negative control.

In certain embodiments, an inhibitor of viral replication is identified if a compound reduces the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to replication of the viral genome in the absence of a compound or relative to a negative control in an assay described herein or others known to one of skill in the art. In certain embodiments, an inhibitor of viral replication is identified if a compound reduces the replication of a viral genome by about 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to replication of the viral genome in the absence of a compound or relative to a negative control in an assay described herein or others known to one of skill in the art. In certain embodiments, an inhibitor of viral replication is identified if a compound reduces the replication of a viral genome by at least 1 log, 1.5 logs, 2 logs, 2.5 logs, 3 logs, 3.5 logs, 4 logs, 4.5 logs, 5 logs or more relative to replication of the viral genome in the absence of a compound or relative to a negative control in an assay described herein or others known to one of skill in the art.

In certain embodiments, an inhibitor of viral replication is identified if a compound reduces the synthesis of viral proteins by at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to the synthesis of viral proteins in the absence of a compound or relative to a negative control in an assay described herein or others known to one of skill in the art in an assay described herein or others known to one of skill in the art. In certain embodiments, an inhibitor of viral replication is identified if a compound reduces the synthesis of viral proteins at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to the synthesis of viral proteins in the absence of a compound or relative to a negative control in an assay described herein or others known to one of skill in the art. In certain embodiments, an inhibitor of viral replication is identified if a compound reduces the synthesis of viral proteins approximately 1 log, 1.5 logs, 2 logs, 2.5 logs, 3 logs, 3.5 logs, 4 logs, 4.5 logs, 5 logs relative to the synthesis of viral proteins in the absence of a compound or relative to a negative control in an assay described herein or others known to one of skill in the art.

In some embodiments, an inhibitor of viral replication is identified if a compound results in 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more reduction of viral yield per round of viral replication. In certain embodiments, a compound results in about a 2 fold or more reduction of viral yield per round of viral replication. In a specific embodiment, a compound results in about a 10 fold or more reduction of viral yield per round of viral replication.

In certain embodiments, a compound is considered an inhibitor of viral replication if it reduces viral replication by at least 2 wells of hemagglutinin (HA) in a hemagglutination assay (see Section 5.3.1.7 below), which equals approximately a 75% reduction in viral titer.

In certain embodiments, a compound is considered an inhibitor of viral replication if it reduces viral titer by 50% or more, by 55% or more, by 60% or more, by 65% or more, by 70% or more, by 75% or more, by 80% or more, by 85% or more, by 90% or more, or by 95% or more.

In certain embodiments, an enhancer of viral replication is identified if a compound increases the virus replication by at least 1.5 fold, 2 fold, 3, fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 100 fold, 500 fold, or 1000 fold relative to virus replication in the absence of compound or the presence of a negative control. In certain embodiments, an enhancer of viral replication is identified if a compound increases the virus replication by 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold. In a specific embodiment, an enhancer of viral replication is identified if a compound increases the virus replication by at least 2 fold relative to virus replication in the absence of compound or the presence of a negative control. In another specific embodiment, an enhancer of viral replication is identified if a compound increases the virus replication by at least 5 fold relative to virus replication in the absence of compound or the presence of a negative control. In a specific embodiment, an enhancer of viral replication is identified if a compound increases the virus replication by at least 10 fold relative to virus replication in the absence of compound or the presence of a negative control.

In certain embodiments, an enhancer of viral replication is identified if a compound increases virus replication by at least 0.5 log, 1 log, 1.5 log, 2 log, 2.5 log, 3 log, 3.5 log, 4 log, 4.5 log, 5 log, 5.5 log, 6 log, 6.5 log, 7 log, 7.5 log, 8 log, 8.5 log, or 9 log relative to culturing the infected cells in the absence of compound. In a specific embodiment, an enhancer of viral replication is identified if a compound increases the virus replication by at least 1 log relative to virus replication in the absence of compound or the presence of a negative control.

In certain embodiments, an enhancer of viral replication is identified if a compound increases the replication of a viral genome by about at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to replication of the viral genome in the absence of a compound or relative to a negative control in an assay described herein or others known to one of skill in the art. In certain embodiments, an enhancer of viral replication is identified if a compound increases the replication of a viral genome by about 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to replication of the viral genome in the absence of a compound or relative to a negative control in an assay described herein or others known to one of skill in the art. In certain embodiments, an enhancer of viral replication is identified if a compound increases the replication of a viral genome by at least 1 log, 1.5 logs, 2 logs, 2.5 logs, 3 logs, 3.5 logs, 4 logs, 4.5 logs, 5 logs or more relative to replication of the viral genome in the absence of a compound or relative to a negative control in an assay described herein or others known to one of skill in the art.

In certain embodiments, an enhancer of viral replication is identified if a compound increases the synthesis of viral proteins by at least 1.5 fold, 2, fold, 3 fold, 4 fold, 5 fold, 6 fold, 7 fold, 8 fold, 9 fold, 10 fold, 15 fold, 20 fold, 25 fold, 30 fold, 35 fold, 40 fold, 45 fold, 50 fold, 75 fold, 100 fold, 500 fold, or 1000 fold relative to the synthesis of viral proteins in the absence of a compound or relative to a negative control in an assay described herein or others known to one of skill in the art in an assay described herein or others known to one of skill in the art. In certain embodiments, an enhancer of viral replication is identified if a compound increases the synthesis of viral proteins at least 1.5 to 3 fold, 2 to 4 fold, 3 to 5 fold, 4 to 8 fold, 6 to 9 fold, 8 to 10 fold, 2 to 10 fold, 5 to 20 fold, 10 to 40 fold, 10 to 50 fold, 25 to 50 fold, 50 to 100 fold, 75 to 100 fold, 100 to 500 fold, 500 to 1000 fold, or 10 to 1000 fold relative to the synthesis of viral proteins in the absence of a compound or relative to a negative control in an assay described herein or others known to one of skill in the art. In certain embodiments, an enhancer of viral replication is identified if a compound increases the synthesis of viral proteins approximately 1 log, 1.5 logs, 2 logs, 2.5 logs, 3 logs, 3.5 logs, 4 logs, 4.5 logs, 5 logs relative to the synthesis of viral proteins in the absence of a compound or relative to a negative control in an assay described herein or others known to one of skill in the art.

In some embodiments, an enhancer of viral replication is identified if a compound results in at least 1.5 fold or more, 2 fold or more, 3 fold or more, 4 fold or more, 5 fold or more, 6 fold or more, 7 fold or more, 8 fold or more, 9 fold or more, 10 fold or more, 15 fold or more, 20 fold or more, 25 fold or more, 30 fold or more, 35 fold or more, 40 fold or more, 45 fold or more, 50 fold or more, 60 fold or more, 70 fold or more, 80 fold or more, 90 fold or more, or 100 fold or more increase of viral yield per round of viral replication. In certain embodiments, a compound results in about a 2 fold or more increase of viral yield per round of viral replication. In a specific embodiment, a compound results in about a 10 fold or more increase of viral yield per round of viral replication.

In certain embodiments, a compound is considered an enhancer of viral replication if it increases viral titer by 50% or more, by 55% or more, by 60% or more, by 65% or more, by 70% or more, by 75% or more, by 80% or more, by 85% or more, by 90% or more, by 95% or more, by 100% or more, by 150% or more, by 200% or more or by 500% or more.

Standard assays for influenza virus replication have been described, See, e.g., Sidwell et al., Antiviral Research, 2000, 48:1-16. These assays can also be adapted for use with other negative-sense, single-stranded RNA viruses.

The effect of a compound on the replication of any negative-sense, single-stranded RNA virus may be determined. Further, the effect of a compound on the replication of any type, subtype or strain of a negative-sense, single-stranded RNA virus may be determined. The negative-sense, single-stranded RNA virus may be a non-segmented or a segmented virus. Non-limiting examples of non-segmented, negative-sense, single-stranded RNA viruses include: rhabdoviruses (e.g., VSV, rabies, and rabies-related viruses), paramyxoviruses (e.g., NDV, Sendai virus, measles virus, mumps virus, parainfluenza virus, and pneumoviruses such as respiratory syncytial virus (RSV) and metapneumovirus), filoviruses (e.g., Ebola virus and Marburg virus), hepatitis delta virus, and bornaviruses. Non-limiting examples of segmented, negative-sense, single-stranded RNA viruses include: orthomyxoviruses (e.g., influenza A virus, influenza B virus, influenza C virus, thogoto virus, and infectious salmon anemia virus), bunyaviruses (e.g., bunyamwera virus, Hantaan virus, Dugbe virus, Rift Valley fever virus, and tomato spotted wilt virus), and arenaviruses (e.g., Lassa virus, Junin virus, Machupo virus, and lymphocytic choriomeningitis virus). In a specific embodiment, the negative-sense, single-stranded RNA virus is an enveloped virus. In another specific embodiment, the negative-sense, single-stranded RNA virus is influenza virus (e.g., an influenza A virus, influenza B virus, or influenza C virus). In another embodiment, the negative-sense, single-stranded RNA virus is a parainfluenza virus or a respiratory syncytial virus (RSV). In another embodiment, the virus is NDV or VSV.

In some embodiments, the effect of a compound on the replication of an attenuated negative-sense, single-stranded RNA virus is determined. In some embodiments, the effect of a compound on the replication of a naturally occurring strain, variant or mutant of a negative-sense, single-stranded RNA virus, a mutagenized negative-sense, single-stranded RNA virus, a reassortant negative-sense, single-stranded RNA virus and/or a genetically engineered negative-sense, single-stranded RNA virus can be assessed. In a specific embodiment, the effect of a compound on the replication of a vaccine strain of a negative-sense, single-stranded RNA virus is determined.

5.3.1.1 Viral Titer Assay

In this non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of compounds (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

5.3.1.2 Flow Cytometry Assay

Flow cytometry can be utilized to detect expression of virus antigens in infected target cells cultured in the presence or absence of compounds (See, e.g., McSharry et al., Clinical Microbiology Rev., 1994, 7:576-604). Non-limiting examples of viral antigens that can be detected on cell surfaces by flow cytometry include, but are not limited to HA of influenza; and H and F of measles virus. In other embodiments, intracellular viral antigens or viral nucleic acid can be detected by flow cytometry with techniques known in the art.

5.3.1.3 Viral Cytopathic Effect (CPE) Assay

CPE is the morphological changes that cultured cells undergo upon being infected by most viruses. These morphological changes can be observed easily in unfixed, unstained cells by microscopy. Forms of CPE, which can vary depending on the virus, include, but are not limited to, rounding of the cells, appearance of inclusion bodies in the nucleus and/or cytoplasm of infected cells, and formation of syncytia, or polykaryocytes (large cytoplasmic masses that contain many nuclei).

The CPE assay can provide a measure of the effect of a compound on virus replication. In a non-limiting example of such an assay, compounds are serially diluted (e.g. 1000, 500, 100, 50, 10, 1 µg/ml) and added to 3 wells containing a cell monolayer (preferably mammalian cells at 80-100% confluent) of a 96-well plate. Within 5 minutes, viruses are added and the plate sealed, incubated at 37° C. for the standard time period required to induce near-maximal viral CPE (e.g., approximately 48 to 120 hours, depending on the virus and multiplicity of infection). When assaying a compound for its potential inhibitory activity, CPE is read microscopically after a known positive control drug (an antiviral) is evaluated in parallel with compounds in each test. A non-limiting example of a positive control is ribavirin for influenza, measles, respiratory syncytial, and parainfluenza. The data is expressed as 50% effective concentrations or approximated virus-inhibitory concentration, 50% endpoint (EC50) and cell-inhibitory concentration, 50% endpoint (IC50). General selectivity index ("SI") is calculated as the IC50 divided by the EC50. These values can be calculated using any method known in the art, e.g., the computer software program MacSynergy II by M. N. Prichard, K. R. Asaltine, and C. Shipman, Jr., University of Michigan, Ann Arbor, Mich.

In one embodiment, a compound has an SI of greater than 3, 4, 5, 6, 7, 8, 9, 10, 11, 12, 13, 14, 15, 20, 21, 22, 23, 24, 25, 30, 35, 39, 40, 45, 50, 60, 70, 80, 90, 100, 200, 300, 400, 500, 1,000, or 10,000. In some embodiments, a compound has an SI of greater than 10. In a specific embodiment, compounds with an SI of greater than 10 are further assessed in other in vitro and in vivo assays described herein or others known in the art to characterize safety and efficacy.

5.3.1.4 Neutral Red (NR) Dye Uptake Assay

The NR Dye Uptake assay can be used to validate the CPE inhibition assay (See Section 5.3.1.3). In a non-limiting example of such an assay, the same 96-well microplates used for the CPE inhibition assay can be used. Neutral red is added to the medium, and cells not damaged by virus take up a greater amount of dye. The percentage of uptake indicating viable cells is read on a microplate autoreader at dual wavelengths of 405 and 540 nm, with the difference taken to eliminate background. (See McManus et al., Appl. Environment. Microbiol. 31:35-38, 1976). An $EC_{50}$ is determined for samples with infected cells and contacted with compounds, and an $IC_{50}$ is determined for samples with uninfected cells contacted with compounds.

For compounds that enhance viral replication, the compound is tested for its ability to increase cell damage caused by virus, as compared to a control wherein the cell is treated with virus alone and a control wherein the cell is treated with the compound alone.

5.3.1.5 Virus Yield Assay

Lysed cells and supernatants from infected cultures such as those in the CPE inhibition assay (See Section 5.3.1.3) can be used to assay for virus yield (production of viral particles after the primary infection). In a non-limiting example, these supernatants are serially diluted and added onto monolayers of susceptible cells (e.g., Vero cells). Development of CPE in these cells is an indication of the presence of infectious viruses in the supernatant.

5.3.1.6 Plaque Assay

In a non-limiting example of a plaque assay, the virus is diluted into various concentrations and added to each well containing a monolayer of the target cells in triplicate. The plates are then incubated for a period of time to achieve effective infection of the control sample (e.g., 1 hour with shaking every fifteen minutes). After the incubation period, an equal amount of 1% agarose is added to an equal volume of each compound dilution prepared in 2× concentration. In certain embodiments, final compound concentrations between 0.03 μg/ml to 100 μg/ml can be tested with a final agarose overlay concentration of 0.5%. The drug agarose mixture is applied to each well in 2 ml volume and the plates are incubated for three days, after which the cells are stained with a 1.5% solution of neutral red. At the end of the 4-6 hour incubation period, the neutral red solution is aspirated, and plaques counted using a stereomicroscope. Alternatively, a final agarose concentration of 0.4% can be used. In other embodiments, the plates are incubated for more than three days with additional overlays being applied on day four and on day 8 when appropriate. In another embodiment, the overlay medium is liquid rather than semi-solid.

5.3.1.7 Hemagglutination Assays

In a non-limiting example of a hemagglutination assay, cells are contacted with a compound and are concurrently or subsequently infected with the virus (e.g., at an MOI of 1) and the virus is incubated under conditions to permit virus replication (e.g., 20-24 hours). The compounds are preferably present throughout the course of infection. Viral replication and release of viral particles is then determined by hemagglutination assays using 0.5% chicken red blood cells. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more.

5.3.2 Cytotoxicity Assays

In some embodiments, compounds differentially affect the viability of uninfected cells and cells infected with virus. The differential effect of a compound on the viability of virally infected and uninfected cells may be assessed using techniques known to one of skill in the art or described herein. In certain embodiments, compounds are more toxic to cells infected with a virus than uninfected cells. In specific embodiments, compounds preferentially affect the viability of cells infected with a virus.

Many assays well-known in the art can be used to assess viability of cells (infected or uninfected) or cell lines following exposure to a compound and, thus, determine the cytotoxicity of the compound. For example, cell proliferation can be assayed by measuring Bromodeoxyuridine (BrdU) incorporation (See, e.g., Hoshino et al., 1986, Int. J. Cancer 38, 369; Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270:18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic-40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocytic cells. In certain embodiments, cytotoxicity is assessed in one or more of the following cell lines: MDCK, MEF, Huh 7.5, Detroit, or human tracheobronchial epithelial (HTBE) cells.

Compounds can be tested for in vivo toxicity in animal models. For example, animal models, described herein and/or others known in the art, used to test the activities of compounds can also be used to determine the in vivo toxicity of these compounds. For example, animals are administered a range of concentrations of compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of a compound in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided in Section 5.5.4, infra.

5.3.3 Apoptosis Assay

Any technique known to one of skill in the art can be used to determine whether a compound has an apoptotic effect. For example, a fluorescence-based assay for caspase-3 activity can be used to detect whether a compound has a pro- or anti-apoptotic effect. In one example of such an assays, cells are seeded into 60 mm tissue culture treated dishes at $1.5 \times 10^6$ cells per dish and allowed to incubate for 24 hours. After incubation, the medium is aspirated and the cells are washed with PBS. Fresh DMEM post-infection medium was added, containing compounds at the same concentrations as has been used for the viral infections. As a positive control for the induction of apoptosis, cells are treated with any known inducer of apoptosis, for example, staurosporin at a concentration of 5 µM. Cells are incubated for 6 hours. Subsequently, they are harvested, washed twice with PBS, lysed and incubated with the colorimetric substrate for an additional hour, at which time fluorescence is measured. An increase in fluorescence relative to a negative control or cells not treated with the compound indicates that the compound is pro-apoptotic.

5.3.4 Animal Model Studies

Compounds and compositions are preferably assayed in vivo for the desired therapeutic or prophylactic activity prior to use in humans. For example, in vivo assays can be used to determine whether it is preferable to administer a compound and/or another therapeutic agent. For example, to assess the use of a compound to prevent a viral infection, the compound can be administered before the animal is infected with the virus. Alternatively, or in addition, a compound can be administered to the animal at the same time that the animal is infected with the virus. To assess the use of a compound to treat or manage a viral infection, in one embodiment, the compound is administered after a viral infection in the animal. In another embodiment, a compound is administered to the animal at the same time that the animal is infected with the virus to treat and/or manage the viral infection. In a specific embodiment, the compound is administered to the animal more than one time.

Compounds can be tested for antiviral activity against virus in animal models systems including, but not limited to, rats, mice, chicken, cows, monkeys, pigs, goats, sheep, dogs, rabbits, guinea pigs, etc. In a specific embodiment of the invention, compounds are tested in a mouse model system. Such model systems are widely used and well-known to the skilled artisan. Compounds can also be tested for replication enhancing activity toward virus replication in animal models systems including, but are not limited to, rats, mice, chicken, cows, monkeys, pigs, goats, sheep, dogs, rabbits, guinea pigs, etc. In a specific embodiment of the invention, compounds are tested in a mouse model system. Such model systems are widely used and well-known to the skilled artisan. Non-limiting examples of animal models for influenza virus are provided in Section 5.3.4.1 below.

Animals are infected with virus and concurrently or subsequently treated with a compound or placebo. Alternatively, animals are treated with a compound or placebo and subsequently infection with virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of a compound on the virulence of a virus can also be determined using in vivo assays in which the titer of the virus in an infected subject administered a compound, the length of survival of an infected subject administered a compound, the immune response in an infected subject administered a compound, the number, duration and/or severity of the symptoms in an infected subject administered a compound, and/or the time period before onset of one or more symptoms in an infected subject administered a compound is assessed. Techniques known to one of skill in the art can be used to measure such effects.

5.3.4.1 Influenza Virus Animal Models

Animal models, such as ferret, mouse, guinea pig, and chicken, developed for use to test antiviral agents against influenza virus have been described, See, e.g., Sidwell et al., Antiviral Res., 2000, 48:1-16; Lowen A. C. et al. PNAS., 2006, 103: 9988-92; and McCauley et al., Antiviral Res., 1995, 27:179-186. For mouse models of influenza, non-limiting examples of parameters that can be used to assay antiviral activity of compounds administered to the influenza-infected mice include pneumonia-associated death, serum α1-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+ (epithelial layer columnar and even in outline with only slightly increased proliferation; cilia still visible on many cells); 2+ (prominent changes in the epithelial layer ranging from attenuation to marked proliferation; cells disorganized and layer outline irregular at the luminal border); 3+ (epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

5.3.5 Assays in Humans

In one embodiment, candidate compounds that modulate replication of a negative-sense, single-stranded RNA virus are assessed human subjects suffering from such an infection with such a virus. In accordance with this embodiment, a candidate compound or a control compound is administered to the human subject, and the effect of a test compound on viral replication is determined by, e.g., analyzing the level of the virus or viral nucleic acids in a biological sample (e.g., serum or plasma). A candidate compound that alters the virus replication can be identified by comparing the level of virus replication in a subject or group of subjects treated with a control compound to that in a subject or group of subjects treated with a candidate compound. Alternatively, alterations in viral replication can be identified by comparing the level of the virus replication in a subject or group of subjects before and after the administration of a candidate compound. Techniques known to those of skill in the art can be used to obtain the biological sample and analyze the mRNA or protein expression.

In another embodiment, the effect of a candidate compound on the severity of one or more symptoms associated with a negative-sense, single-stranded RNA virus are assessed in a subject having such a virus infection. In accordance with this embodiment, a candidate compound or a control compound is administered to a human subject suffering from a negative-sense, single-stranded RNA virus infection and the effect of a candidate compound on one or more symptoms of the virus infection is determined. A candidate compound that reduces one or more symptoms can be identified by comparing the subjects treated with a control compound to the subjects treated with the test compound. Techniques known to physicians familiar with infectious diseases can be used to determine whether a candidate compound reduces one or more symptoms associated with the infectious disease.

5.4 Compositions

Any compound described herein may optionally be in the form of a composition comprising the compound and a carrier, excipient or diluent. In certain embodiments provided herein, compositions (including pharmaceutical compositions) comprise a compound and a pharmaceutically acceptable carrier, excipient, or diluent.

In other embodiments, provided herein are pharmaceutical compositions comprising an effective amount of a compound and a pharmaceutically acceptable carrier, excipient, or diluent. In a specific embodiment, the pharmaceutical compositions comprise an inhibitor of a negative-sense, single-stranded RNA virus. The pharmaceutical compositions are suitable for veterinary and/or human administration.

The pharmaceutical compositions provided herein can be in any form that allows for the composition to be administered to a subject, preferably a human.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose free compositions can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Specific lactose free dosage forms comprise a compound, microcrystalline cellulose, pre gelatinized starch, and magnesium stearate.

Further provided herein are anhydrous pharmaceutical compositions and dosage forms comprising one or more compounds, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions. Compositions and dosage forms that comprise lactose and at least one compound that comprises a primary or secondary amine are preferably anhydrous if substantial contact with moisture and/or humidity during manufacturing, packaging, and/or storage is expected.

An anhydrous composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided herein are compositions and dosage forms that comprise one or more agents that reduce the rate by which a compound will decompose. Such agents, which are referred to herein as "stabilizers," include, but are not limited to, antioxidants such as ascorbic acid, pH buffers, or salt buffers.

The compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a compound preferably in purified form, together with a suitable amount of carrier so as to provide the form for proper administration to the patient. The formulation should suit the mode of administration. In a specific embodiment, the compositions or single unit dosage forms are sterile and in suitable form for administration to a subject, preferably an animal subject, more preferably a mammalian subject, and most preferably a human subject.

Compositions provided herein are formulated to be compatible with the intended route of administration. Examples of routes of administration include, but are not limited to, parenteral, e.g., intravenous, intradermal, subcutaneous, oral (e.g., inhalation), intranasal, transdermal (topical), transmucosal, intra-synovial and rectal administration. In a specific embodiment, the composition is formulated in accordance with routine procedures as a composition adapted for intravenous, subcutaneous, intramuscular, oral, intranasal or topical administration to human beings. In a specific embodiment, a composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non aqueous liquid suspensions, oil in water emulsions, or a water in oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms provided herein are prepared by combining a compound in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions provided herein is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103 and Starch 1500 LM.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms provided herein include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A compound can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased patient compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or agents.

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl and benzyl benzoate.

Agents that increase the solubility of one or more of the compounds provided herein can also be incorporated into the parenteral dosage forms provided herein.

Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 &

1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms provided herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with a compound. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more compounds. Similarly, the polarity of a solvent carrier, its ionic strength, or tonicity can be adjusted to improve delivery. Agents such as stearates can also be added to pharmaceutical compositions or dosage forms to advantageously alter the hydrophilicity or lipophilicity of one or more compounds so as to improve delivery. In this regard, stearates can serve as a lipid vehicle for the formulation, as an emulsifying agent or surfactant, and as a delivery enhancing or penetration enhancing agent. Different salts, hydrates or solvates of the compounds can be used to further adjust the properties of the resulting composition.

In certain specific embodiments, the compositions are in oral, injectable, or transdermal dosage forms. In one specific embodiment, the compositions are in oral dosage forms. In another specific embodiment, the compositions are in the form of injectable dosage forms. In another specific embodiment, the compositions are in the form of transdermal dosage forms.

5.5 Prophylactic and Therapeutic Uses of Inhibitors of Virus Replication

The invention provides methods for inhibiting replication of a negative-sense, single-stranded RNA virus utilizing an inhibitor described herein. In a specific embodiment, a method for inhibiting replication of a negative-sense, single-stranded RNA virus comprises contacting an inhibitor with a composition comprising a cell infected with a negative-sense, single-stranded RNA virus. In another embodiment, a method for inhibiting replication of a negative-sense, single-stranded RNA virus comprises: (i) contacting a cell that permits replication of the negative-sense, single-stranded RNA virus with an inhibitor; and (ii) infecting the cell with the negative-sense, single-stranded RNA virus. In another embodiment, a method for inhibiting replication of a negative-sense, single-stranded RNA virus comprises: (i) infecting a cell with a negative-sense, single-stranded RNA virus, wherein the cell permits replication of a negative-sense, single-stranded RNA virus; and (ii) contacting the infected cell with an inhibitor. In certain embodiments, the cell is contacted with a negative-sense, single-stranded RNA virus concurrently or within, for example, 5 seconds, 15 seconds, 30 seconds, 1 minute, 5 minutes, 15 minutes, 30 minutes, 1 hour, 2 hours, 6 hours, 12 hours, 16 hours or 24 hours of each other. In certain embodiments, the inhibitor is a PKC inhibitor. In certain embodiments, the PKC inhibitor is not H7, staurosporine, bisindolylmaleimide I, calphostin C, or Gö6976. In certain embodiments, the inhibitor is a sodium channel opener. In certain embodiments, the inhibitor is a calcium channel opener. In certain embodiments, the inhibitor is a Na+/K+ ATPase inhibitor. In one embodiment, the inhibitor is ouabain, lanatoside C, digoxin, SDZ-201106, strophanthidin, or rottlerin. In another embodiment, the inhibitor is K8644 (±) or FPL-64176. In another embodiment, the inhibitor a compound with the formula A3-G, including, but not limited to, 2-(5-(2,3-dimethyl-1H-indol-5-yl)-1,3,4-oxadiazol-2-ylthio)-1-(pyrrolidin-1-yl)ethanone ("A3"); 2-(5-(2,3-dimethyl-1H-indol-5-yl)-1,3,4-oxadiazol-2-ylthio)-N,N-diethylacetamide ("A3-2"); 2-(5-(2,3-dimethyl-1H-indol-5-yl)-1,3,4-oxadiazol-2-ylthio)-1-(indolin-1-yl) ethanone ("A3-3"); 2-(5-(2,3-dimethyl-1H-indol-5-yl)-1,3,4-oxadiazol-2-ylthio)-N,N-diisopropylacetamide ("A3-4"); 2-(5-(2,3-dimethyl-1H-indol-5-yl)-1,3,4-oxadiazol-2-ylthio)-1-morpholinoethanone ("A3-5"); or 1-(azepan-1-yl)-2-(5-(2,3-dimethyl-1H-indol-5-yl)-1,3,4-oxadiazol-2-ylthio)ethanone ("A3-6"). In certain embodiments, the inhibitor is a compound with the formula A3. In other embodiments, the inhibitor is a compound with the formula A3-2, A3-3, A3-4, A3-5, or A3-6. In certain embodiments, the inhibitor is a compound with the formula 4-(4-bromophenyl)-N-methyl-N-(tetrahydro-1,1-dioxido-3-thienyl)-2-thiazolamine ("A35"); N-methyl-4-(4-nitrophenyl)-N-(phenylmethyl)-2-thiazolamine ("A35-1"); 4-[[4-(4-chlorophenyl)-1,3-thiazol-2-yl](methyl)amino]phenol ("A35-4"); or 4-(4-chlorophenyl)-N,N-dimethylthiazol-2-amine ("A35-5"). In certain specific embodiments, the inhibitor is a compound with the formula A35. In other embodiments, the inhibitor is a compound with the formula 9-(benzo[d][1,3]dioxol-5-yl)-4-hydroxy-6,7-dimethoxynaphtho[2,3-e]furan-1(3H)-one ("C2"). In particular embodiments, the inhibitor is a not a compound with the formula C2.

The invention provides methods for inhibiting replication of negative-sense, single-stranded RNA viruses in a subject comprising administering an inhibitor of viral replication to the subject. In a specific embodiment, the inhibitor is administered to a subject infected with the virus. In certain embodiments, the inhibitor is a PKC inhibitor. In certain embodiments, the PKC inhibitor is not H7, staurosporine, bisindolylmaleimide I, calphostin C, or Gö6976. In certain embodiments, the inhibitor is a sodium channel opener. In certain embodiments, the inhibitor is a calcium channel opener. In certain embodiments, the inhibitor is a Na+/K+ ATPase inhibitor. In one embodiment, the inhibitor is ouabain, lanatoside C, digoxin, SDZ-201106, strophanthidin, or rottlerin. In one embodiment, the inhibitor is K8644 (±) or FPL-64176. In another embodiment, the inhibitor is K8644 (±) or FPL-64176. In another embodiment, the inhibitor is a compound with the formula A3-G, such as a compound with the formula A3, A3-2, A3-3, A3-4, A3-5 or A3-6; a compound with the formula A35, A35-1, A35-4, A35-5; or a compound with the formula C2. In certain embodiments, the inhibitor is not a compound with the formula C2.

The invention provides methods of preventing, treating and/or managing a negative-sense, single-stranded RNA virus infection, said methods comprising administering to a subject in need thereof one or more inhibitors. In a specific embodiment, the invention provides a method of preventing, treating and/or managing a negative-sense, single-stranded RNA virus infection, said method comprising administering to a subject in need thereof a dose of a prophylactically or therapeutically effective amount of one or more inhibitors or a composition comprising an inhibitor. A compound or a composition comprising an inhibitor may be used as any line of therapy (e.g., a first, second, third, fourth or fifth line therapy) for a negative-sense, single-stranded RNA virus infection.

Non-limiting examples of non-segmented, negative-sense, single-stranded RNA viruses whose replication may be inhibited or reduced or whose infection may be prevented, treated and/or managed by the administration of one or more inhibitors or a composition comprising one or more inhibitors include: rhabdoviruses (e.g., vesicular stomatitis virus (VSV), rabies, and rabies-related viruses), paramyxoviruses (e.g., Newcastle Disease Virus (NDV), measles virus, mumps virus, parainfluenza viruses such as Sendai virus, and pneumoviruses such as respiratory syncytial virus (RSV) and metapneumovirus), filoviruses (e.g., Ebola virus and Marburg virus), hepatitis delta virus, and bornaviruses. Non-limiting examples of segmented, negative-sense, single-stranded RNA viruses whose replication may be inhibited or reduced or whose infection may be prevented, treated and/or managed by the administration of one or more inhibitors or a composition comprising one or more inhibitors include: orthomyxoviruses (e.g., influenza A virus, influenza B virus, influenza C virus, thogoto virus, and infectious salmon anemia virus), bunyaviruses (e.g., bunyamwera virus, Hantaan virus, Dugbe virus, Rift Valley fever virus, and tomato spotted wilt virus), and arenaviruses (e.g., Lassa virus, Junin virus, Machupo virus, and lymphocytic choriomeningitis virus). In a specific embodiment, the negative-sense, single-stranded RNA virus is an enveloped virus. In another specific embodiment, the negative-sense, single-stranded RNA virus is influenza virus (e.g., an influenza A virus, influenza B virus, or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus, a measles virus, a mumps virus, or a respiratory syncytial virus (RSV). In one embodiment, the parainfluenza virus is Sendai virus. In one embodiment, the parainfluenza virus is a human parainfluenza virus (HPIV). In specific embodiments the HPIV is HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the virus is NDV. In another specific embodiment, the virus is VSV. In certain embodiments, the virus is not a rhabdovirus. In certain other embodiments, the negative-sense, single-stranded RNA virus is not VSV. In certain embodiments, the negative-sense, single-stranded RNA virus is not a Sendai virus.

In a specific embodiment, the negative-sense, single-stranded RNA virus infects humans. In some embodiments, the negative-sense, single-stranded RNA virus is a naturally occurring strain, variant or mutant of a negative-sense, single-stranded RNA virus, a mutagenized negative-sense, single-stranded RNA virus, a reassortant negative-sense, single-stranded RNA virus and/or a genetically engineered negative-sense, single-stranded RNA virus.

In specific embodiments, an inhibitor is the only active ingredient administered to prevent, treat and/or manage a negative-sense, single-stranded RNA virus infection. In a certain embodiment, an inhibitor is the only active ingredient in a composition that is administered to prevent, treat and/or manage a negative-sense, single-stranded RNA virus. In other embodiments, more than one inhibitor is administered in order to achieve a synergistic effect.

In different embodiments of the invention, the inhibitor may interfere with one or more stages of the viral life cycle. The steps of a viral life cycle include, but are not limited to, virus attachment to the host cell surface, penetration or entry of the host cell (e.g., through receptor mediated endocytosis or membrane fusion), uncoating (the process whereby the viral capsid is removed is degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In a specific embodiment, the inhibitor interferes with entry into the host cell. In certain specific embodiments, the inhibitor interferes with entry of viruses that enter cells by endocytosis. In certain embodiments, the inhibitor interferes with entry of viruses that enter cells by endocytosis but not entry of viruses that enter cells by fusion with the plasma membrane. In a specific embodiment, the inhibitor interferes with viral genome replication. In another embodiment, the inhibitor interferes with synthesis of viral mRNA and/or viral protein synthesis. In another embodiment, the inhibitor interferes with viral RNA packaging. In another embodiment, the inhibitor interferes with viral RNA trafficking.

In particular embodiments, compounds which inhibit or reduce the replication of negative-sense, single-stranded RNA viruses inhibit one or more of the following steps of the viral life cycle: viral entry, RNA replication, or RNA transcription. These steps of the viral cycle may be assayed using techniques known to one of skill in the art. RNA replication and transcription may be measured by measuring the replication and transcription of reporter gene product from an influenza virus mini-genome reporter construct, using, e.g., the assays disclosed herein. Such assays permit the identification of inhibitors of the viral polymerase or inhibitors of cellular proteins that are involved in viral RNA replication, translation or RNA trafficking. In some embodiments, the inhibitor affects steps in the viral life cycle up to and including translation of viral RNAs, but not later stages in the viral life cycle such as, e.g., viral assembly, budding and release. In some embodiments, the compound does not have an inhibitory effect on the overall host cell replication machinery, or has only a slight inhibitory effect compared to the effect on viral replication, as monitored by assays such as, e.g., the expression of a renilla luciferase reporter from a control plasmid (e.g., pGL3 described in Section 6 below).

In some embodiments, an inhibitor specifically interferes with the replication of a negative-sense, single-stranded RNA virus. In other embodiments, an inhibitor interferes with the replication of multiple negative-sense, single-stranded RNA viruses. The inhibitor may interfere with the replication of one or more of the following non-segmented negative-sense, single-stranded RNA viruses: a rhabdovirus (e.g., vesicular stomatitis virus (VSV) or a rabies or rabies-related virus), a paramyxovirus (e.g., Newcastle Disease Virus (NDV), measles virus, mumps virus, a parainfluenza virus such as Sendai virus, or a pneumovirus such as respiratory syncytial virus (RSV) or metapneumovirus), filovirus (e.g., Ebola virus or Marburg virus), hepatitis delta virus, or bornavirus. The inhibitor may interfere with the replication of one or more of the following segmented, negative-sense, single-stranded RNA viruses: an orthomyxovirus (e.g., influenza A virus, influenza B virus, influenza C virus, thogoto virus, or infectious salmon anemia virus), a bunyavirus (e.g., a bunyamwera virus, Hantaan virus, Dugbe virus, Rift Valley fever virus, or tomato spotted wilt virus), or an arenavirus (e.g., Lassa virus, Junin virus, Machupo virus, or lymphocytic choriomeningitis virus). In a specific embodiment, the negative-sense, single-stranded RNA virus is an enveloped virus. In another specific embodiment, the negative-sense, single-stranded RNA virus is a influenza virus (e.g., an influenza A virus, influenza B virus or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus, a measles virus, a mumps virus or a respiratory syncytial virus (RSV). In one embodiment, the parainfluenza virus is Sendai virus. In one embodiment, the parainfluenza virus is a human parainfluenza virus (HPIV). In specific embodiments the HPIV is HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the negative-sense, single-stranded RNA virus is NDV. In a specific embodiment, the negative-sense, single-stranded RNA virus is VSV. In certain embodiments, the negative-sense, single-stranded RNA virus is not a rhabdovirus. In certain embodiments, the negative-sense, single-stranded RNA virus is not VSV.

In some embodiments, an inhibitor reduces the viral replication of one type, subtype or strain of a negative-sense, single-stranded A virus more than another. For example, an inhibitor may reduce the replication of an influenza A virus more than it reduces the replication of an influenza B virus, and vice versa.

The choice of inhibitors to be used depends on a number of factors, including but not limited to the type of viral infection, health and age of the patient, and toxicity or side effects.

The present invention encompasses methods for preventing, treating, and/or managing a negative-sense, single-stranded RNA virus infection for which no antiviral therapy is available. The present invention also encompasses methods for preventing, treating, and/or managing a negative-sense, single-stranded RNA virus infection as an alternative to other conventional therapies.

The present invention also provides methods of preventing, treating and/or managing a negative-sense, single-stranded RNA virus infection, said methods comprising administering to a subject in need thereof one or more of the inhibitors and one or more other therapies (e.g., prophylactic or therapeutic agents). In a specific embodiment, the other therapies are currently being used, have been used or are known to be useful in the prevention, treatment and/or management of a viral infection. Non-limiting examples of such therapies are provided in Section 5.5.3.1, infra. In a specific embodiment, one or more inhibitors are administered to a subject in combination with one or more of the therapies described in Section 5.5.3.1, infra. In another embodiment, one or more inhibitors are administered to a subject in combination with a supportive therapy, a pain relief therapy, or another therapy that does not have antiviral activity.

The combination therapies of the invention can be administered sequentially or concurrently. In one embodiment, the combination therapies of the invention comprise an inhibitor and at least one other therapy which has the same mechanism of action. In another embodiment, the combination therapies of the invention comprise an inhibitor and at least one other therapy which has a different mechanism of action than the inhibitor.

In a specific embodiment, the combination therapies of the present invention improve the prophylactic and/or therapeutic effect of an inhibitor by functioning together with the inhibitor to have an additive or synergistic effect. In another embodiment, the combination therapies of the present invention reduce the side effects associated with each therapy taken alone.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

5.5.1 Patient Population

In some embodiments, an inhibitor, a composition comprising an inhibitor, or a combination therapy is administered to a subject suffering from a negative-sense, single-stranded RNA virus infection. In other embodiments, an inhibitor, a composition comprising an inhibitor, or a combination therapy is administered to a subject predisposed or susceptible to a negative-sense, single-stranded RNA virus infection. In some embodiments, an inhibitor, a composition comprising an inhibitor, or a combination therapy is administered to a subject that lives in a region where there has been or might be an outbreak with a negative-sense, single-stranded RNA virus infection. In some embodiments, the negative-sense, single-stranded RNA virus infection is a latent viral infection. In other embodiments, the negative-sense, single-stranded RNA virus infection is an active infection. In yet other embodiments, the negative-sense, single-stranded RNA virus infection is a chronic viral infection.

In certain embodiments, an inhibitor, a composition comprising an inhibitor or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an inhibitor, a composition comprising an inhibitor or a combination therapy is administered to a human at risk for a virus infection. In certain embodiments, an inhibitor, a composition comprising an inhibitor or a combination therapy is administered to a human with a virus infection. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an inhibitor, a composition comprising an inhibitor or a combination therapy is administered to a human infant. In other embodiments, an inhibitor, a composition comprising an inhibitor or a combination therapy is administered to a human child. In other embodiments, an inhibitor, a composition comprising an inhibitor or a combination therapy is administered to a human adult. In yet other embodiments, an inhibitor, a composition comprising an inhibitor or a combination therapy is administered to an elderly human.

In certain embodiments, an inhibitor, a composition comprising an inhibitor or a combination therapy is administered to a pet, e.g., a dog or cat. In certain embodiments, an inhibitor, a composition comprising an inhibitor or a combination therapy is administered to a farm animal or livestock, e.g., pig, cows, horses, chickens, etc. In certain embodiments, an inhibitor, a composition comprising an inhibitor or a combination therapy is administered to a bird, e.g., ducks or chicken.

In certain embodiments, an inhibitor, a composition comprising an inhibitor or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an inhibitor, a composition comprising an inhibitor or a combination therapy is administered to a subject receiving or recovering from immunosuppressive therapy. In certain embodiments, an inhibitor, a composition comprising an inhibitor or a combination therapy is administered to a subject that has or is at risk of getting cancer, AIDS, another viral infection, or a bacterial infection. In certain embodiments, an inhibitor, a composition comprising an inhibitor or a combination therapy is administered to a subject that is, will or has undergone surgery, chemotherapy and/or radiation therapy. In certain embodiments, an inhibitor, a composition comprising an inhibitor or a combination therapy is administered to a subject that has cystic fibrosis, pulmonary fibrosis, or another disease which makes the subject susceptible to a viral infection. In certain embodiments, an inhibitor, a composition comprising an inhibitor or a combination therapy is administered to a subject that has, will have or had a tissue transplant. In some embodiments, an inhibitor, a composition comprising an inhibitor or a combination therapy is administered to a subject that lives in a nursing home, a group home (i.e., a home for 10 or more subjects), or a prison. In some embodiments, an inhibitor, a composition comprising an inhibitor or a combination therapy is administered to a subject that attends school (e.g., elementary school, middle school, junior high school, high school or university) or daycare. In some embodiments, an inhibitor, a composition comprising an inhibitor or a combination therapy is administered to a subject that works in the healthcare area, such as a doctor or a nurse, or in a hospital. In certain embodiments, an inhibitor, a composition comprising an inhibitor or a combination therapy is administered to a subject that is pregnant or plans on becoming pregnant.

In some embodiments, a patient is administered an inhibitor, a composition comprising an inhibitor or a combination therapy before any adverse effects or intolerance to therapies other than inhibitor develops. In some embodiments, an inhibitor, a composition comprising an inhibitor or a combination therapy is administered to refractory patients. In a certain embodiment, refractory patient is a patient refractory to a standard antiviral therapy. In certain embodiments, a patient with a viral infection, is refractory to a therapy when the infection has not significantly been eradicated and/or the symptoms have not been significantly alleviated. The determination of whether a patient is refractory can be made either in vivo or in vitro by any method known in the art for assaying the effectiveness of a treatment of infections, using art-accepted meanings of "refractory" in such a context. In various embodiments, a patient with a viral infection is refractory when viral replication has not decreased or has increased.

In some embodiments, an inhibitor, a composition comprising an inhibitor or a combination therapy is administered to a patient to prevent the onset or reoccurrence of a negative-sense, single-stranded RNA virus infection in a patient at risk of developing such infections. In some embodiments, an inhibitor, a composition comprising an inhibitor or a combination therapy is administered to a patient who is susceptible to adverse reactions to conventional therapies.

In some embodiments, an inhibitor, a composition comprising an inhibitor or a combination therapy is administered to a patient who has proven refractory to therapies other than compounds, but are no longer on these therapies. In certain embodiments, the patients being managed or treated in accordance with the methods of this invention are patients already being treated with antibiotics, antivirals, antifungals, or other biological therapy/immunotherapy. Among these patients are refractory patients, patients who are too young for conventional therapies, and patients with reoccurring viral infections despite management or treatment with existing therapies.

In some embodiments, the subject being administered an inhibitor, a composition comprising an inhibitor or a combination therapy has not received a therapy prior to the administration of the inhibitor or composition or combination therapy. In other embodiments, an inhibitor, a composition comprising an inhibitor or a combination therapy is administered to a subject who has received a therapy prior to administration of the inhibitor, composition or combination therapy. In some embodiments, the subject administered an inhibitor, a composition comprising an inhibitor or a combination therapy was refractory to a prior therapy or experienced adverse side effects to the prior therapy or the prior therapy was discontinued due to unacceptable levels of toxicity to the subject.

5.5.2 Mode of Administration

When administered to a patient, an inhibitor is preferably administered as a component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of an inhibitor into the bloodstream.

In specific embodiments, it may be desirable to administer an inhibitor locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce an inhibitor into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, an inhibitor is formulated as a suppository, with traditional binders and vehicles such as triglycerides.

For viral infections with cutaneous manifestations, the inhibitor can be administered topically. Similarly, for viral infections with ocular manifestation, the inhibitor can be administered ocularly. For viruses with pulmonary manifestations, the inhibitor can be administered intranasally or by an inhaler or nebulizer.

In another embodiment, an inhibitor is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327; See generally ibid.).

In another embodiment, an inhibitor is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising an inhibitor is placed in close proximity to the tissue infected with a virus to be prevented, treated and/or managed. In accordance with this embodiment, the close proximity of the controlled-release system to the infection may result in only a fraction of the dose of the inhibitor required if it is systemically administered.

In certain embodiments, it may be preferable to administer an inhibitor via the natural route of infection of the virus against which an inhibitor has antiviral activity. For example, it may be desirable to administer an inhibitor into the lungs by any suitable route to treat or prevent an infection of the respiratory tract by viruses (e.g., influenza virus). Pulmonary administration can also be employed, e.g., by use of an inhaler or nebulizer, and formulation with an aerosolizing agent for use as a spray.

5.5.3 Agents for Use in Combination with Inhibitors

Therapeutic or prophylactic agents that can be used in combination with inhibitors for the prevention, treatment and/or management of a negative-sense, single-stranded RNA virus infection include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such agents include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, and non-steroidal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Any therapy which is known to be useful, or which has been used or is currently being used for the prevention, management, and/or treatment of a negative-sense, single-stranded RNA virus or can be used in combination with inhibitors in accordance with the invention described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 199 9; Cecil Textbook of Medicine, 20th Ed., Bennett and Plum (eds.), W.B. Saunders, Philadelphia, 1996, and Physicians' Desk Reference ($61^{st}$ ed. 1007) for information regarding therapies (e.g., prophylactic or therapeutic agents) which have been or are currently being used for preventing, treating and/or managing viral infections.

5.5.3.1 Antiviral Agents

Antiviral agents that can be used in combination with inhibitors include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination inhibitors include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.5.3.2 Antibacterial Agents

Antibacterial agents, including antibiotics, that can be used in combination with inhibitors include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracyclins, and analogs thereof. In some embodiments, antibiotics are administered in combination with an inhibitor to prevent and/or treat a bacterial infection.

In a specific embodiment, inhibitors are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is selected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with inhibitors include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithromycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamecillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.5.4 Dosages & Frequency of Administration

The amount of an inhibitor, or the amount of a composition comprising an inhibitor, that will be effective in the prevention, treatment and/or management of a negative-sense, single-stranded RNA virus infection can be determined by standard clinical techniques. In vitro or in vivo assays may optionally be employed to help identify optimal dosage ranges. The precise dose to be employed will also depend, e.g., on the route of administration, the type of invention, and the seriousness of the infection, and should be decided according to the judgment of the practitioner and each patient's or subject's circumstances.

In some embodiments, the dosage of an inhibitor is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m$^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005. In one embodiment, an inhibitor or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die ($LD_{10}$). In general the starting dose of a Phase I clinical trial is based on preclinical testing. A standard measure of toxicity of a drug in preclinical testing is the percentage of animals that die because of treatment. It is well within the skill of the art to correlate the $LD_{10}$ in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about 1/10 the murine $LD_{10}$, although it may be even lower if other species (i.e., dogs) were more sensitive to the inhibitor. In other embodiments, the standard conservative starting dose is about 1/100, 1/95, 1/90, 1/85, 1/80, 1/75, 1/70, 1/65, 1/60, 1/55, 1/50, 1/45, 1/40, 1/35, 1/30, 1/25, 1/20, 1/15, 2/10, 3/10, 4/10, or 5/10 of the murine $LD_{10}$. In other embodiments, an starting dose amount of an inhibitor in a human is lower than the dose extrapolated from animal model studies. In another embodiment, an starting dose amount of an inhibitor in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of inhibitors or compositions include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In another embodiment, the dosage is a unit dose of 5 mg, preferably 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 mg, about 150 mg to about 300 mg, about 150 mg to about 400 mg, 250 mg to about 500 mg, about 500 mg to about 800 mg, about 500 mg to about 1000 mg, or about 5 mg to about 1000 mg.

In certain embodiments, suitable dosage ranges for oral administration are about 0.001 milligram to about 500 milligrams of a compound, per kilogram body weight per day. In specific embodiments of the invention, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one compound is administered, then, in some embodiments, the dosages correspond to the total amount administered. In a specific embodiment, oral compositions contain about 10% to about 95% a compound of the invention by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration. Effective doses may be extrapolated from dose-response curves derived from in vitro or animal model test systems. Such animal models and systems are well known in the art.

In another embodiment, a subject is administered one or more doses of a prophylactically or therapeutically effective amount of an inhibitor or a composition, wherein the prophylactically or therapeutically effective amount is not the same for each dose.

In certain embodiments, a subject is administered an inhibitor or a composition in an amount effective to inhibit viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered an inhibitor or a composition in an amount effective to inhibit or reduce viral genome replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered a inhibitor or a composition in an amount effective to inhibit or reduce viral genome replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments, a subject is administered an inhibitor or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered an inhibitor or a composition in an amount effective to inhibit or reduce viral protein synthesis by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered an inhibitor or a composition in an amount effective to inhibit or reduce viral protein synthesis by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered an inhibitor or a composition in an amount effective to inhibit or reduce the spread of a virus from a cell, tissue, or organ to another cell, tissue or organ by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an inhibitor or a composition in an amount effective to inhibit or reduce the spread of a virus from a cell, tissue or organ to another cell, tissue or organ by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments, a subject is administered an inhibitor or a composition in an amount effective to inhibit or reduce viral titer by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an inhibitor or a composition in an amount effective to inhibit or reduce viral titer by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered an inhibitor or a composition in an amount effective to inhibit or reduce viral titer by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered an inhibitor or a composition in an amount effective to inhibit or reduce viral replication by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an inhibitor or a composition in an amount effective to inhibit or reduce viral replication by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered an inhibitor or a composition in an amount effective to inhibit or reduce viral replication by 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments, a subject is administered an inhibitor or a composition in an amount effective to inhibit or reduce the ability of the virus to spread to other individuals by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In other embodiments, a subject is administered an inhibitor or a composition in an amount effective to inhibit or reduce the ability of the virus to spread to other cells, tissues or organs in the subject by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art.

In certain embodiments, a dose of an inhibitor or a composition is administered to a subject every day, every other day, every couple of days, every third day, once a week, twice a week, three times a week, or once every two weeks. In other embodiments, two, three or four doses of an inhibitor or a composition is administered to a subject every day, every couple of days, every third day, once a week or once every two weeks. In some embodiments, a dose(s) of an inhibitor or a composition is administered for 2 days, 3 days, 5 days, 7 days, 14 days, or 21 days. In certain embodiments, a dose of an inhibitor or a composition is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a negative-sense, single-stranded RNA virus infection can be determined using references available to a clinician such as, e.g., the Physicians' Desk Reference ($61^{st}$ ed. 2007). In a specific embodiment, dosages lower than those which have been or are currently being used to prevent, treat and/or manage the infection are utilized in combination with one or more inhibitors or compositions.

For inhibitors which have been approved for uses other than prevention, treatment or management of viral infections, safe ranges of doses can be readily determined using references available to clinicians, such as e.g., the Physician's Desk Reference ($61^{st}$ ed. 2007).

The above-described administration schedules are provided for illustrative purposes only and should not be considered limiting. A person of ordinary skill in the art will readily understand that all doses are within the scope of the invention.

5.6 Use of Inhibitors in Cell Culture and as Disinfectants

The present invention provides for the use of inhibitors as ingredients in cell culture-related products in which it is desirable to have antiviral activity. In one embodiment, one or more inhibitors is added to cell culture media. In certain embodiments, inhibitors that prove too toxic or are not used in subjects are added to cell culture-related products, such as media. The present invention also provides for the use of inhibitors as ingredients in disinfectants and soaps.

5.7 Uses of Enhancers of Viral Replication

The present invention provides for the use of enhancers as ingredients viral substrate-related products (e.g., cell culture-related products) in which it is desirable to have increased replication of a negative-sense, single-stranded RNA virus. In one embodiment, an enhancer is added to cell culture media. In a specific embodiment, an enhancer is used in compositions to increase the replication of vaccine strains of negative-sense, single-stranded RNA viruses. In such an embodiment, the enhancer is intended to enhance the manufacture of negative-sense, single-stranded RNA virus vaccines, particularly vaccines comprising attenuated negative-sense, single-stranded RNA viruses that are difficult to grow in, e.g., cell-based systems.

In one embodiment, a method for enhancing the replication of a negative, single-stranded RNA virus in a substrate for propagating virus, comprises contacting the substrate with an enhancer of virus replication. The substrate may be contacted with the enhancer before, concurrently and/or after infection with a negative-sense, single-stranded RNA virus. In some embodiments, the substrate is infected before (e.g., 5 minutes, 10 minutes, 30 minutes, 45 minutes, 1 hour, 3 hours, 6 hours, 12 hours, 16 hours, 24 hours, 48 hours or 72 hours before) infecting the substrate with a negative-sense, single-stranded RNA virus. In other embodiments, the substrate is contacted with the enhancer concurrently with infection with a negative-sense, single-stranded RNA virus. In yet another embodiments, the substrate is contacted with the enhancer after (e.g., 5 minutes, 10 minutes, 15 minutes, 30 minutes, 45 minutes, 1 hour, 3 hours, 6 hours, 12 hours, 16 hours, 24 hours or 48 hours after) infection with a negative-sense, single-stranded RNA virus.

Non-limiting examples of non-segmented, negative-sense, single-stranded RNA viruses whose replication may be enhanced include: rhabdoviruses (e.g., vesicular stomatitis virus (VSV), rabies, and rabies-related viruses), paramyxoviruses (e.g., Newcastle Disease Virus (NDV), measles virus, mumps virus, parainfluenza viruses such as Sendai virus, and pneumoviruses such as respiratory syncytial virus (RSV) and metapneumovirus), filoviruses (e.g., Ebola virus and Marburg virus), hepatitis delta virus, and bornaviruses. Non-limiting examples of segmented, negative-sense, single-stranded RNA viruses whose replication may be enhanced include: Non-limiting examples of segmented, negative-sense, single-stranded RNA viruses that may be prevented, treated and/or managed by the administration of one or more inhibitors or a composition comprising one or more inhibitors include: orthomyxoviruses (e.g., influenza A virus, influenza B virus, influenza C virus, thogoto virus, and infectious salmon anemia virus), bunyaviruses (e.g., bunyamwera virus, Hantaan virus, Dugbe virus, Rift Valley fever virus, and tomato spotted wilt virus), and arenaviruses (e.g., Lassa virus, Junin virus, Machupo virus, and lymphocytic choriomeningitis virus). In a specific embodiment, the negative-sense, single-stranded RNA virus is an enveloped virus. In another specific embodiment, the negative-sense, single-stranded RNA virus is influenza virus (e.g., an influenza A virus, influenza B virus or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus, a measles virus, a mumps virus or a respiratory syncytial virus (RSV). In one embodiment, the parainfluenza virus is a Sendai virus. In one embodiment, the parainfluenza virus is a human parainfluenza virus (HPIV). In specific embodiments the HPIV is HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the negative-sense, single-stranded RNA virus infects humans. In certain embodiments, the negative-sense, single-stranded RNA virus is not a Sendai virus. In some embodiments, the negative-sense, single-stranded RNA virus is a naturally occurring strain, variant or mutant of a negative-sense, single-stranded RNA virus, a mutagenized negative-stranded RNA virus, a reassortant negative-sense, single-stranded RNA virus and/or a genetically engineered negative-sense, single-stranded RNA virus. In some embodiments, the negative-sense, single-stranded RNA virus is a vaccine strain, such as an attenuated virus.

The enhancer may be added to any substrate contemplated for use in the growth of a negative-sense, single-stranded RNA virus. For example, the enhancer may be added to any of the following substrates: cells (e.g. avian cells, chicken cells (e.g., primary chick embryo cells or chick kidney cells), Vero cells, MDCK cells, human respiratory epithelial cells (e.g., A549 cells), calf kidney cells, mink lung cells, etc.) that are susceptible to infection by a negative-sense, single-stranded RNA virus, embryonated eggs, or animals (e.g., birds).

In some embodiments, the cell, embryonated egg, or animal to be treated with the enhancer is infected with a negative-sense, single-stranded RNA virus. In some embodiments, the cell, embryonated egg, or animal is treated with the enhancer prior to infection with the virus. In some embodiments, the cell, embryonated egg, or animal is treated with the enhancer concurrently with infection with the virus. In some embodiments, the cell, embryonated egg, or animal is treated with the enhancer after infection with the virus. In specific embodiments, the substrate is infected with one of the following exemplary non-segmented negative-sense, single-stranded RNA viruses: a rhabdovirus (e.g., vesicular stomatitis virus (VSV) or a rabies or rabies-related virus), a paramyxovirus (e.g., Newcastle Disease Virus (NDV), measles virus, mumps virus, a parainfluenza virus such as Sendai virus, or a pneumovirus such as respiratory syncytial virus (RSV) and metapneumovirus), filovirus (e.g., Ebola virus and Marburg virus), hepatitis delta virus, or bornavirus. In specific embodiments, the substrate is infected with one of the following exemplary segmented, negative-sense, single-stranded RNA viruses: an orthomyxovirus (e.g., influenza A virus, influenza B virus, influenza C virus, thogoto virus, or infectious salmon anemia virus), a bunyavirus (e.g., a bunyamwera virus, Hantaan virus, Dugbe virus, Rift Valley fever virus, or tomato spotted wilt virus), or an arenavirus (e.g., Lassa virus, Junin virus, Machupo virus, or lymphocytic choriomeningitis virus). In a specific embodiment, the negative-sense, single-stranded RNA virus is an enveloped virus. In another specific embodiment, the negative-sense, single-stranded RNA virus is influenza virus (e.g., an influenza A virus, influenza B virus, or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus or a respiratory syncytial virus (RSV). In one embodiment, the parainfluenza virus is a human parainfluenza virus (HPIV). In specific embodiments the HPIV is Sendai virus, HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B. In a specific embodiment, the negative-sense, single-stranded RNA virus infects humans. In certain embodiments, the negative-sense, single-stranded RNA virus is not a Sendai virus. In some embodiments, the negative-sense, single-stranded RNA virus is a naturally occurring strain, variant or mutant of a negative-sense, single-stranded RNA virus, a mutagenized negative-sense, single-stranded RNA virus, a reassortant negative-sense, single-stranded RNA virus and/or a genetically engineered negative-sense, single-stranded RNA virus. In some embodiments, the negative-sense, single-stranded RNA virus is a vaccine strain, such as an attenuated virus.

In some embodiments, the invention encompasses viral growth substrates (e.g., cells and eggs) treated with an enhancer. In other embodiments, the invention encompasses viral growth substrates (e.g., cells and eggs) treated with an enhancer that are infected with a negative-sense, single-stranded RNA virus.

In different embodiments of the invention, the enhancer may positively affect one or more stages of the viral life cycle, such as, for example, virus attachment to the host cell surface, penetration or entry of the host cell (e.g., through receptor mediated endocytosis or membrane fusion), uncoating (the process whereby the viral capsid is removed is degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In a specific embodiment, the enhancer increases viral genome replication. In another embodiment, the enhancer increases the synthesis of viral mRNA and/or viral protein synthesis.

In some embodiments, an enhancer specifically enhances the replication of a negative-sense, single-stranded RNA virus. In other embodiments, an enhancer enhances the replication of more than one negative-sense, single-stranded RNA virus. The enhancer may enhance the replication of one or more of the following non-segmented negative-sense, single-stranded RNA viruses: a rhabdovirus (e.g., vesicular stomatitis virus (VSV) or a rabies, or rabies-related virus), a paramyxovirus (e.g., Newcastle Disease Virus (NDV), measles virus, mumps virus, a parainfluenza virus such as Sendai virus, or a pneumovirus such as respiratory syncytial virus (RSV) or metapneumovirus), filovirus (e.g., Ebola virus and Marburg virus), hepatitis delta virus, or bornavirus. The enhancer may enhance the replication of one or more of the following segmented, negative-sense, single-stranded RNA viruses: an orthomyxovirus (e.g., influenza A virus, influenza B virus, influenza C virus, thogoto virus, or infectious salmon anemia virus), a bunyavirus (e.g., a bunyamwera virus. Hantaan virus, Dugbe virus, Rift Valley fever virus, or tomato spotted wilt virus), or an arenavirus (e.g., Lassa virus, Junin virus, Machupo virus, or lymphocytic choriomeningitis virus). In a specific embodiment, the negative-sense, single-stranded RNA virus is an enveloped virus. In another specific embodiment, the negative-sense, single-stranded RNA virus is influenza virus (e.g., an influenza A virus, influenza B virus, or influenza C virus). In one embodiment, the influenza A virus is an H5N1 isolate. In another embodiment, the influenza A virus is an H1N1 isolate. In another embodiment, the negative-sense, single-stranded RNA virus is a parainfluenza virus or a respiratory syncytial virus (RSV). In one embodiment, the parainfluenza virus is a human parainfluenza virus (HPIV). In specific embodiments the HPIV is Sendai virus, HPIV type 2 (HPIV-2), HPIV type 3 (HPIV-3), or HPIV type 4 (HPIV-4). In one embodiment, the HPIV-4 is subtype A. In another embodiment, the HPIV-4 is subtype B.

The invention encompasses vaccine formulations comprising viruses, in particular, attenuated viruses, wherein the viruses have been grown on substrates treated with the enhancers. The virus used in the vaccine formulation may be selected from naturally occurring mutants or variants, mutagenized viruses or genetically engineered viruses. Attenuated strains of segmented, negative, stranded RNA viruses can also be generated via reassortment techniques, or by using a combination of the reverse genetics approach and reassortment techniques. Naturally occurring variants include viruses isolated from nature as well as spontaneous occurring variants generated during virus propagation. The attenuated virus can itself be used as the active ingredient in the vaccine formulation. Alternatively, the attenuated virus can be used as the vector or "backbone" of recombinantly produced vaccines. To this end, recombinant techniques such as reverse genetics (or, for segmented viruses, combinations of the reverse genetics and reassortment techniques) may be used to engineer mutations or introduce foreign antigens into the attenuated virus used in the vaccine formulation. In this way, vaccines can be designed for immunization against strain variants, or in the alternative, against completely different infectious agents or disease antigens.

Virtually any heterologous gene sequence may be constructed into the viruses for use in vaccines. Preferably, epitopes that induce a protective immune response to any of a variety of pathogens, or antigens that bind neutralizing antibodies may be expressed by or as part of the viruses. For example, heterologous gene sequences that can be constructed into the viruses of the invention for use in vaccines include but are not limited to epitopes of human immunodeficiency virus (HIV) such as gp120; hepatitis B virus surface antigen (HBsAg); the glycoproteins of herpes virus (e.g. gD, gE); VP 1 of poliovirus; antigenic determinants of non-viral pathogens such as bacteria and parasites, to name but a few. In another embodiment, all or portions of immunoglobulin genes may be expressed. For example, variable regions of anti-idiotypic immunoglobulins that mimic such epitopes may be constructed into the viruses of the invention. In yet another embodiment, tumor associated antigens may be expressed.

The vaccine formulations include an attenuated negative-sense, single-stranded RNA virus, wherein the attenuation results from a mutation in a gene required for efficient replication. The invention also encompasses vaccine formulations comprised of an attenuated negative-sense, single-stranded RNA virus wherein the attenuation results from a combination of one or more mutations in other viral genes.

Vaccine formulations may include genetically engineered negative strand RNA viruses that have mutations in the NS1 gene or any other gene that leads to attenuation and does not impair the ability of the host to launch an immune response against the virus, including but not limited to the influenza mutants with truncated or deleted NS1 genes described in issued patents U.S. Pat. No. 6,468,544, issued Oct. 22, 2002, U.S. Pat. No. 6,866,853, issued Mar. 15, 2005, and U.S. Pat. No. 6,669,943, issued Dec. 30, 2003 and copending application U.S. Patent Application Publication No. US 2004-0109877, published Jun. 10, 2004. The vaccine formulations may also be formulated using natural variants, such as the A/turkey/Ore/71 natural variant of influenza A, or B/201, and B/AWBY-234, which are natural variants of influenza B. When formulated as a live virus vaccine, a range of about $10^4$ pfu to about $5 \times 10^6$ pfu per dose should be used.

The invention also includes vaccine formulations which are chimeric viruses. A chimeric virus could be comprised of any virus where the interferon antagonist gene is derived from either a different virus or a different strain of the same virus.

The invention includes a vaccine formulation comprising an attenuated negative-sense, single-stranded RNA virus for treating or preventing any infectious disease. The infectious disease could be a virus. By way of example, but not as a limitation the vaccine formulation could be used to treat or prevent infection with influenza virus, Ebola virus, respiratory syncytial virus, HIV, herpes virus, hepatitis C virus or hepatitis B virus. The infectious disease could consist of a bacterium or a parasite. Additionally the vaccine could be used to treat or prevent cancer or tumor growth.

The invention includes the use of an enhancer to increase the propagation of negative-sense, single-stranded RNA viruses for use as either live viral vaccines or inactivated viral vaccines. The production of a live vaccine may be preferred because multiplication in the host leads to a prolonged stimulus of similar kind and magnitude to that occurring in natural infections, and therefore, confers substantial, long-lasting immunity.

In a specific embodiment, the invention provides a method for enhancing the production of a negative, single-stranded RNA virus for use in a vaccine formulation, comprising contacting an enhancer of virus replication with a substrate infected with the negative, single-stranded RNA virus. In some embodiments, the substrate is contacted with the enhancer before infection with the virus, the virus is permitted to replicate under conditions suitable for virus replication, and the progeny virus is purified. In some embodiments, the enhancer and the virus are concurrently contacted with the substrate, the virus is permitted to replicate under conditions suitable for virus replication, and the progeny virus is purified. In a specific embodiment, the substrate contacted with the enhancer is a cell that is infected with the virus, the cell is incubated under conditions that permit viral replication, e.g., for 18 hours at 37° C., and the virus-containing supernatant is collected. In certain embodiments, progeny virus is plaque purified using techniques known to one of skill in the art, such as those described herein.

In one embodiment, a method for manufacture of a negative-sense, single-stranded RNA virus vaccine is provided, comprising: (i) contacting a PKC activator with a substrate infected with a negative-sense, single-stranded RNA virus under conditions that permit the negative-sense, single-stranded RNA virus to replicate; and (ii) purifying the negative-sense, single-stranded RNA virus. In another embodiment, a method for manufacture of a negative-sense, single-stranded RNA virus vaccine is provided, comprising: (i) contacting a sodium channel inhibitor with a substrate infected with a negative-sense, single-stranded RNA virus under conditions that permit the negative-sense, single-stranded RNA virus to replicate; and (ii) purifying the negative-sense, single-stranded RNA virus. In another embodiment, a method for manufacture of a negative-sense, single-stranded RNA virus vaccine is provided, comprising: (i) contacting a calcium channel inhibitor with a substrate infected with a negative-sense, single-stranded RNA virus under conditions that permit the negative-sense, single-stranded RNA virus to replicate; and (ii) purifying the negative-sense, single-stranded RNA virus. In another embodiment, a method for manufacture of a negative-sense, single-stranded RNA virus vaccine is provided, comprising: (i) contacting a PKC activator with a substrate that permits replication of the negative-sense, single-stranded RNA virus; (ii) infecting the substrate with the negative-sense, single-stranded RNA virus; and (iii) purifying the negative-sense, single-stranded RNA virus. In another embodiment, a method for manufacture of a negative-sense, single-stranded RNA virus vaccine is provided, comprising: (i) contacting a sodium channel inhibitor with a substrate that permits replication of the negative-sense, single-stranded RNA virus; (ii) infecting the substrate with the negative-sense, single-stranded RNA virus; and (iii) purifying the negative-sense, single-stranded RNA virus. In another embodiment, a method for manufacture of a negative-sense, single-stranded RNA virus vaccine is provided, comprising: (i) contacting a calcium channel inhibitor with a substrate that permits replication of the negative-sense, single-stranded RNA virus; (ii) infecting the substrate with the negative-sense, single-stranded RNA virus; and (iii) purifying the negative-sense, single-stranded RNA virus. In certain of these embodiments, the negative-sense, single-stranded RNA virus is influenza virus, VSV or NDV. In certain embodiments, the virus is attenuated. In certain embodiments, said method for the manufacture of a negative-sense, single-stranded RNA virus vaccine further comprises inactivating the virus.

In certain embodiments, the invention provides a method for manufacture of an influenza virus vaccine, comprising: (i) contacting PMA, mezerein, phenamil, 2',4'-dichlorobenzamil or 3',4'-dichlorobenzamil with a substrate infected with an influenza virus under conditions that permit the influenza virus to replicate; and (ii) purifying the influenza virus. In certain embodiments, the invention provides a method for manufacture of an influenza virus vaccine, comprising: (i) contacting PMA, mezerein, phenamil, 2',4'-dichlorobenzamil or 3',4'-dichlorobenzamil with a substrate that permits replication of influenza virus; (ii) infecting the substrate with the influenza virus; and (iii) purifying the influenza virus. In certain embodiments, the virus is attenuated. In certain embodiments, said method for the manufacture of an influenza virus vaccine further comprises inactivating the virus.

In one embodiment, the invention provides a method for the manufacture of a negative-sense, single-stranded RNA virus vaccine, comprising: (a) contacting an enhancer of virus replication with a substrate infected with an attenuated negative, single-stranded RNA virus; and (b) purifying the virus from the substrate. In another embodiment, the invention provides a method for the manufacture of an inactivated negative, single-stranded RNA virus, comprising: (a) contacting an enhancer of virus replication with a substrate infected with a negative, single-stranded RNA virus; (b) purifying the virus from the substrate; and (c) inactivating the virus. In certain embodiments, the enhancer is a sodium channel inhibitor, such as phenamil or 2',4'-dichlorobenzamil. In other embodiments, the enhancer is a PKC activator, such as PMA or mezerein.

The vaccine formulations manufactured using an enhancer may be administered to a subject by a method known to one of skill in the art, including, but are not limited to, intranasal, intratracheal, oral, intradermal, intramuscular, intraperitoneal, intravenous, and subcutaneous routes. It may be preferable to introduce the virus vaccine formulation via the natural route of infection of the pathogen for which the vaccine is designed, or via the natural route of infection of the parental attenuated virus. Where a live influenza virus vaccine preparation is used, it may be preferable to introduce the formulation via the natural route of infection for influenza virus. The ability of influenza virus to induce a vigorous secretory and cellular immune response can be used advantageously. For example, infection of the respiratory tract by influenza viruses may induce a strong secretory immune response, for example in the urogenital system, with concomitant protection against a particular disease causing agent.

A vaccine formulation manufactured using an enhancer may comprise $10^4$-$5\times10^6$ pfu of virus, and can be administered once. Alternatively, a vaccine formulation manufactured using an enhancer may comprise $10^4$-$5\times10^6$ pfu of virus, and can be administered twice or three times with an interval of 2 to 6 months between doses. Alternatively, a formulation manufactured using an enhancer may comprise $10^4$-$5\times10^6$ pfu of virus, and can be administered as often as needed to an animal, preferably a mammal, and more preferably a human being.

5.8 Kits

The present invention provides kits that can be used in the above methods. In one embodiment, the kit comprises an inhibitor contained in an appropriate package. In another embodiment, a kit comprises an enhancer contained in an appropriate package. In specific embodiments, a kit comprises an inhibitor and enhancer, each contained in an appropriate package. In some embodiments, a kit further comprises a negative control and/or a positive control, in an appropriate package(s). In some embodiments, the kit further comprises a negative-sense, single-stranded RNA virus. In certain embodiments, the kit further comprises a mini-genome reporter construct, in an appropriate package. In specific embodiments, the kit contains instructions for use.

6. EXAMPLE

This example describes the identification of compounds that modulate the replication of influenza virus, a negative-sense, single-stranded RNA virus. In particular, this example describes the identification of protein kinase C (PKC) activators and sodium channel inhibitors that increase influenza virus replication. This example also describes the identification of PKC inhibitors and a sodium channel opener as compounds that inhibit influenza virus replication.

6.1 MATERIALS AND METHODS

Cell lines, viruses and plasmids. Human alveolar basal epithelial (A549) cells, African green monkey kidney (Vero) cells, chicken embryo fibroblast (DF1) cells and Madin-Darby canine kidney (MDCK) cells, were obtained from the American Type Culture Collection (ATCC, Manassas, Va.). A549 cells, Vero cells and DF1 cells were cultured in Dulbecco's modified Eagle's medium (DMEM) (Invitrogen Corp., Carlsbad, Calif.) supplemented with 10% fetal bovine serum (FBS) (HyClone; South Logan, Utah) and 100 U/mL penicillin G sodium and 100 μg/mL streptomycin sulfate (Invitrogen Corp., Carlsbad, Calif.). MDCK cells were cultured in Minimum Essential Medium (MEM) (Invitrogen Corp., Carlsbad, Calif.) supplemented with 10% FBS, 2 mM L-glutamine (Invitrogen Corp., Carlsbad, Calif.), 100 U/mL penicillin G sodium and 100 mg/L streptomycin sulfate and 0.15% $NaHCO_3$ (Invitrogen Corp., Carlsbad, Calif.).

Influenza A/WSN/33 virus and influenza B/Yamagata/88 virus were grown in MDCK cells in MEM-post-infection medium (MEM supplemented with 0.3% bovine serum albumin (BSA), 0.1% FBS, 2 mM L-glutamine, 100 U/mL penicillin G sodium and 100 μg mL streptomycin sulfate and 0.15% $NaHCO_3$). Viruses were titered by standard plaque assay in MDCK cells. Vesicular stomatitis virus expressing the green fluorescent protein (VSV-GFP) was provided by John Hiscott (McGill University, Montreal, Canada), and was grown and titered in Vero cells. Newcastle disease virus strain B1 (rNDV/B1) was grown in 10-day-old embryonated hens' eggs and titered in DF1 cells. The human isolates influenza A/Moscow/10/99 and A/Wyoming/03/2003 viruses were grown in 8-day-old embryonated hens' eggs and titered in MDCK cells. The recombinant 6:2 influenza A/PR/8/34 virus reassortant expressing the hemagglutinin (HA) and the neuraminidase (NA) of influenza ANN/1203/04 virus (referred to as H5N1/PR8 in this study) was rescued using reverse genetics (Fodor et al., 1999). The HA of influenza A/VN/1203/04 virus was mutated by removing the multibasic cleavage site which is associated with high pathogenicity in chickens (Senne et al., 1996). Briefly, expression plasmids and pPol I plasmids encoding the HA and NA genes of influenza A/VN/1203/04 virus were co-transfected into 293T cells together with ambisense pDZ plasmids encoding the PB1, PB2, PA, NP, M and NS segments of influenza A/PR/8/34 virus. The supernatant was transferred 48 hours later into 8-day-old embryonated hens' eggs to allow the recombinant virus to propagate. The egg-grown virus stock was sequenced and titered in MDCK cells.

For the construction of the influenza mini-genome reporter construct (pPolI-358Luc) the firefly luciferase open reading frame from pGL3 (Promega Corp., Madison, Wis.) was amplified by PCR and the 5' and 3' ends of the cRNA promoter of the influenza A/WSN/33 virus NP segment were incorporated on either end (Neumann and Hobom, 1995). This product was then inserted into the pPolI vector (Pleschka et al., 1996) with the luciferase gene in the negative sense.

Small molecular weight compounds. The Prestwick Chemical Library (1120 compounds; Prestwick Chemical, Inc., Washington, D.C.), the NINDS custom collection 2 (1040 compounds; National Institute of Neurological Disorders and Stroke; Bethesda, Md.) and BIOMOL Known Bioactives-2 library (480 compounds; BIOMOL, Plymouth Meeting, Pa.) were provided by The Institute of Chemistry and Cell Biology (ICCB), National Screening Laboratory for the Regional Centers of Excellence in Biodefense and Emerging Infectious Disease (NSRB) (Harvard University, Boston, Mass.). The compounds were dissolved in DMSO at 2 mg/mL for the Prestwick library, 5 mg/mL for the BIOMOL2 library and at 10 mM for the NINDS2 library.

For secondary analyses 2',4'-dichlorobenzamil and SDZ-201106 were purchased from BIOMOL (Plymouth Meeting, Pa.) while 3',4'-dichlorobenzamil, phenamil, phorbol 12-myristate 13-acetate (PMA), mezerein, rottlerin, staurosporin, ouabain and lanatoside C were purchased from Sigma-Aldrich (St. Louis, Mo.). All compounds were dissolved in either water or dimethyl sulfoxide (DMSO) to a stock concentration of 10 mM. The final concentration of DMSO in the culture medium did not exceed 0.004%.

High-throughput screening. The assay was performed in duplicate using solid white 384-well tissue culture treated plates (Corning Life Sciences; Lowell, Mass.). A549 cells were cultured to 90% confluency, trypsinized with 0.05% Trypsin-EDTA (Invitrogen Corp., Carlsbad, Calif.), and resuspended in phenol red-free DMEM growth medium supplemented with 10% FBS at $7.2 \times 10^5$ cells/mL. Transfections were done in bulk and for each well, 12.5 ng of the reporter pPolI-358Luc was diluted in 6.25 μL OptiMEM (Invitrogen Corp., Carlsbad, Calif.) and mixed with 6.25 μL OptiMEM containing 0.025 μL Lipofectamine-2000 (Invitrogen Corp., Carlsbad, Calif.). The transfection mix was incubated for 20 min before adding 12.5 μL of resuspended A549 cells (approximately $9 \times 10^3$ cells). The medium also included 0.25 μg/mL Scriptaid (BIOMOL, Plymouth Meeting, Pa.) and 1.0 μg/mL 5-aza-2'-deoxycytidine (Sigma-Aldrich; St. Louis, Mo.), which were added to enhance reproducibility of the assay (Hellebrekers et al., 2007). The mix of cells and reporter DNA was transferred into 384-well plates using the Matrix Wellmate plate filler. Loaded plates were subsequently centrifuged at 1000 rpm for 5 min to ensure an equal distribution of cells within each well. The cells were incubated for 18 hours at 37° C., 5% $CO_2$, 95% humidity before the addition of 100 nL of compounds by the Epson compound transfer robot (Epson America, Inc.; Long Beach, Calif.). The cells were incubated for a further 6 hours before infection with influenza A/WSN/33 virus directly into the medium at an MOI of 2.5. The virus was added automatically to the plates using the Matrix Wellmate plate filler and the plates were subsequently centrifuged at 1000 rpm for 2 min. Each plate also contained mock-infected cells that were used as a positive control and cells that were infected but untreated, which were used as a negative control. Infection was allowed to proceed for 18-20 hours at 37° C., 5% $CO_2$, 95% humidity. At that time 50% of the medium in each well was removed and the plates were equilibrated to room temperature for at least 20 min. The Matrix Wellmate plate filler was used to add 16 µL of BrightGloLuciferase reagent (Promega Corp., Madison, Wis.) to each well automatically and following a 2 min centrifugation at 2000 rpm, luminescence was measured for 0.1 s/well with the EnVision2 plate reader (Perkin Elmer Inc., Waltham, Mass.).

To eliminate cytotoxic compounds that appear as false positives, a counter screen was performed in parallel. This consisted of A549 cells transfected with pGL3 and seeded at a density of 2500 cells per well of a 384-well plate. The remainder of the assay was performed as described above except that the cells were not infected.

Data analysis. To evaluate the HTS assay robustness, 384-well plates containing no compounds were run separately on two different days. Statistical parameters were determined as follows: $Z'=1-((3\sigma i+3\sigma m)/|\mu i-\mu m|)$, where $\mu i$ is the mean signal for the negative control (infected cells), $\sigma i$ the standard deviation for the negative control, $\mu m$ the mean signal for the positive control (mock infected cells), and $\sigma m$ is the standard deviation for the positive control. The percent coefficient of variation $(CV)=\sigma i/\mu i \times 100$, the signal-to-background ratio $(S/B)=\mu i/\mu m$ and the signal-to-noise ratio $(S/N)=(\mu i-\mu m)/((\sigma i)2+(\sigma m)2)1/2$ (Ghosh et al., 2005; Zhang et al., 1999).

The data from the influenza HTS assay and counter screen data were analyzed with Microsoft Office Excel. The average of the negative control of each plate was set at 100% luminescence and the percent luminescence of each compound-containing well was determined in relation to this internal control. The average percent luminescence for the duplicate screenings was calculated and the compounds were classified into strong or medium inhibitors based on a 90-100% or 70-89% reduction in luminescence, respectively. Compounds leading to an increase in luminescence were considered as enhancers with at least a 2 fold induction above the negative control. The HTS data were compared to the corresponding data from the counter screen. A reduction in luminescence greater than 20-30% in the counter screen was considered to be caused by cytotoxicity and therefore the compound was defined as a false positive and eliminated from further analysis. This threshold was decreased down to 50% in cases where the compound caused a >95% reduction of luminescent signal in the influenza HTS assay.

Cell viability assay. The CellTiter 96 AQueous One Solution Cell Proliferation Assay (referred to as the MTS assay in this study) (Promega Corp., Madison, Wis.) was used to detect cell viability according to the specifications of the manufacturer. Briefly, A549 cells were seeded into 96-well plates (Corning Life Sciences, Lowell, Mass.) at $5 \times 10^3$ cells per well and allowed to incubate for 24 hours at 37° C., 5% $CO_2$. After incubation, the medium was aspirated and replaced with 100 µL of fresh DMEM containing the compounds at various concentrations. Following a further 24 hour incubation, the MTS solution was added to each well and left to incubate for 2 hours before measuring absorbance at 450 nm using a Beckman Coulter DTX 880 plate reader (Beckman Coulter, Inc., Fullerton, Calif.).

Viral growth assays in the presence of inhibitors or enhancers. A549 cells were seeded into 6-well plates at $5 \times 10^5$ cells per well. After incubation for 24 hours at 37° C. and 5% $CO_2$, the cells were washed with phosphate buffered saline (PBS) (Invitrogen Corp., Carlsbad, Calif.) and the medium was replaced with DMEM supplemented with 0.3% BSA, 0.1% FBS and 100 U/mL penicillin G sodium and 100 µg/mL streptomycin sulfate containing the compound of interest. Compounds that enhance viral replication were used at their most potent concentration (400 nM for 2',4'-dichlorobenzamil and 3',4'-dichlorobenzamil, 10 µM for phenamil, 250 nM for mezerein and 250 nM for PMA). Compounds that inhibit viral replication were used at their most potent, but non-toxic, concentration (12.5 µM for SDZ-201106 and 1.25 µM for rottlerin). Cardioactive glycosides were tested at concentrations that maintained at least an 80% cell viability (20 nM for ouabain and 78 nM for lanatoside C). The cells were incubated in the compound-containing media for 6 hours prior to infection. When testing the response of influenza A/WSN/33 virus and of H5N1/PR8 virus to enhancers, infections were done at a multiplicity of 0.001, whereas a multiplicity of 1 was used when testing the response of influenza A/WSN/33 virus to inhibitors. For the human isolates, influenza viruses A/Moscow/10/99 and A/Wyoming/03/2003, infections were done at an MOI of 0.01 when testing enhancers. For influenza B/Yamagata/88 virus, infections were done at a multiplicity of 5 when testing inhibitors and a multiplicity of 0.1 when testing enhancers. Compounds were absent during the 1 hour incubation with the virus but were present in the post-infection medium (DMEM supplemented with 0.3% BSA, 0.1% FBS and 100 U/mL penicillin G sodium and 100 µg/mL streptomycin sulfate). For infection with influenza B virus, the human influenza A virus isolates and the H5N1/PR8 virus this post-infection medium also contained 1 µg/ml TPCK-treated trypsin (Sigma-Aldrich; St. Louis, Mo.). The infected cells were incubated at 37° C. with the exception for influenza B virus infected cells, which were incubated at 33° C. The viral titers for all viruses were determined at various times post infection by standard plaque assay in MDCK cells. When testing the effects of the cardioactive glycosides on the growth of NDV and VSV-GFP, infections were performed at an MOI of 1. Viral titers were determined at 24 hours post infection by standard plaque assay in Vero cells for VSV-GFP and in DF1 cells for NDV/B1. The NDV plaques were visualized by immuno-staining with an anti-NP antibody (Matrosovich et al., 2006).

Apoptosis assay. The Caspase-3 Colorimetric Assay (R&D Systems, Inc., Minneapolis, Minn.) was used to detect whether the compounds have pro- or anti-apoptotic effects. A549 cells were seeded into 60 mm tissue culture treated dishes (Corning Life Sciences, Lowell, Mass.) at $1.5 \times 10^6$ cells per dish and allowed to incubate for 24 hours at 37° C., 5% $CO_2$. After incubation, the medium was aspirated and the cells were washed with PBS. Fresh DMEM post-infection medium was added, containing compounds at the same concentrations as were used for the viral infections. As a positive control for the induction of apoptosis, the cells were treated with staurosporin at a concentration of 5 µM. Cells were incubated for 6 hours at 37° C., 5% $CO_2$. Subsequently, they were harvested, washed twice with PBS, lysed and incubated with the DEVD-AFC substrate for an additional hour at 37° C., 5% $CO_2$ before measuring fluorescence at 500 nm using a Versa Fluor Fluorometer (BioRad; Hercules, Calif.).

6.2 RESULTS

6.2.1 A High-Throughput Screen Identifies Compounds that Modulate Influenza Virus Growth A cell-based HTS assay for the identification of small molecules that can negatively or positively affect influenza A virus replication was developed. An influenza mini-genome reporter construct was designed encoding firefly luciferase in the negative sense in between the cRNA promoter of the influenza A/WSN/33 virus NP segment. This construct was cloned into a plasmid flanked by a human RNA polymerase I promoter and the hepatitis D virus (HDV) ribozyme (FIG. 1A). Upon transfection of this reporter into human lung epithelial (A549) cells, RNA polymerase I transcription generates an RNA segment that mimics viral RNA. When these cells are subsequently infected with influenza virus, this segment is recognized by the viral polymerase resulting in the production of firefly luciferase mRNA. Luciferase activity therefore serves as a measurement of influenza virus replication and decreases or increases in this signal that are observed in the presence of specific compounds are indicative of inhibitory or enhancing activities, respectively. Due to the fact that a high multiplicity of infection provided the greatest reproducibility, the assay is preferred for detecting compounds that act on steps up to and including translation. To detect inhibitors of the later stages such as assembly, budding and release, a multicycle format would be preferred. This is because this assay differs from other cell-based HTS assays for influenza virus that rely on virus-induced cytopathic effect (CPE) as readout and use a low multiplicity of infection (Noah et al., 2007). Such assays can only be performed in Madin-Darby canine kidney (MDCK) cells, which display significant CPE in response to influenza virus infection. In contrast, this cell-based HTS assay can be performed in cells that are a biologically relevant cell type for influenza virus infection, such as A549 cells. The assay was initially optimized in 96-well format and its validity for use in a high-throughput screen was confirmed by demonstrating a Z' factor (Zhang et al., 1999) of 0.74. For screening purposes the assay was further adapted to 384-well format. Table 1 below shows the statistical parameters used to evaluate the robustness of the assay in this format. Here the Z' factor was determined as 0.55 and 0.56 in two separate runs. The discrepancy between the Z' factor values determined in 96-well plates and 384-well plates can be explained by the "edge effect" and higher variability in the miniaturized 384-well format. However, both formats meet the requirements for high-throughput screening. Assays with a Z' factor value of $1>Z'\geq 0.5$ are considered to be excellent for use in HTS and the larger the value, the higher the data quality (Zhang et al., 1999). Additional parameters which verify that the assay is robust are the coefficient of variation, CV (14.9±0.2%), the signal-to-background ratio, S/B ($>10^4$) and the signal-to-noise ratio, S/N (6.7±0.1). The S/N ratio is slightly below the ratio of another reported HTS for influenza virus (S/N>10) (Noah et al., 2007) and reflects a higher signal deviation in this assay which nonetheless is still better compared to a HTS assay for SARS coronavirus (S/N>3) (Severson et al., 2007). Recently, a number of cell-based HTS assays were developed for screening compounds against different viruses. The S/B ratio of this assay of $>10^4$ is strongly above those of other HTS assays reported for influenza virus (S/B>30) (Noah et al., 2007), for SARS coronavirus (S/B=~10) (Severson et al., 2007), for human immunodeficiency virus (HIV-1) (S/B>100) (Blair et al., 2005), for hepatitis C virus (HCV) (S/B>13) (Zuck et al., 2004) and for dengue virus (S/B=8) (Chu and Yang, 2007). This high S/B ratio in addition to a CV of ~15% proves the suitability of our assay for use in a high-throughput screen. Subsequently a screen was conducted at the Harvard Institute for Cell and Chemical Biology (ICCB) in which where 2 library plates (704 compounds) were tested in duplicate. When screening a library plate containing uncharacterized compounds, one strong inhibitor was found (0.28%) while 18 strong inhibitors (~5%) were detected when screening compounds of known bioactivity. Overall, 19 strong inhibitors were identified, which equals a hit rate of 2.7%. This rate may be explained in part by the fact that cytotoxic compounds were included in these hits; thus, in order to eliminate the false positives, a counter screen was run in parallel (as described in the next paragraph) in future screens.

TABLE 1

Summary of statistical parameters to assess the
robustness of the HTS assay in 384-well format

|  | Z'[a] | % CV[b] | S/B[c] | S/N[d] |
|---|---|---|---|---|
| Screen 1 | 0.56 | 14.7 | 14586 | 6.8 |
| Screen 2 | 0.55 | 15.1 | 10734 | 6.6 |

[a] $Z' = 1 - ((3\sigma_i + 3\sigma_m)/|\mu_i - \mu_m|)$ where $\sigma_i$ is the standard deviation for the negative control, $\sigma_m$ is the standard deviation for the positive control, $\mu_i$ is the mean signal for the negative control (infected cells) and $\mu_m$ the mean signal for the positive control (mock infected cells).
[b] % CV (coefficient of variation) = $\sigma_i/\mu_i \times 100$
[c] S/B (signal-to-background ratio) = $\mu_i/\mu_m$
[d] S/N (signal-to-noise ratio) = $(\mu_i - \mu_m)/((\sigma_i)^2 + (\sigma_m)^2)^{1/2}$ Initially, three compound libraries consisting of collections from NINDS, Prestwick and BIOMOL, were screened, totaling 2640 small molecules. All of these compounds have known biological activity (i.e. their cellular targets are known) which facilitates the downstream analyses. A549 cells transfected with the reporter plasmid in bulk were plated in solid white 384-well plates and incubated overnight at 37° C. Six hours prior to infection, 100 nL of the test compounds in library-defined concentrations were added automatically to each well, in duplicate. Influenza A/WSN/33 virus was added to the media at a multiplicity of infection (MOI) of 2.5, and infection was allowed to proceed for 18-20 hours at 37° C. After adding the luciferase substrate, luminescence was measured and compared to control wells that received no compound as well as to the results of the counter screen for elimination of false positives. From the 2640 screened compounds, 59 (2.2%) were identified as strong inhibitors with the luciferase signal reduced by 90-100%. An additional 43 compounds (1.6%) were found to reduce the signal by 70-89% and 4 of the compounds (0.15%) increased luminescence by at least two-fold (FIG. 1B). Some of the same compounds were present in either two or all of the libraries and were identified as hits independently two or three times. Therefore in total, identified 47 (1.8%) unique strong inhibitors, 37 (1.4%) unique moderate inhibitors, and 4 (0.15%) enhancers were identified.

Table 2 shows the functional classes of the hit compounds that were identified as inhibitors in the HTS screen. About 24% of the inhibitors are compounds that interfere with DNA. Another group of 21% consist of antibiotics, antifungals and antiparasitic drugs. Roughly 13% of the inhibitors target different cellular kinases like protein kinase A, protein kinase C and receptor tyrosine kinases and more than 8% of the inhibitory compounds are $Na^+/K^+/ATPase$ pump inhibitors (ouabain, lanatoside C, digoxin, strophanthidin), known as cardioactive glycosides. The initial effect of these compounds and of SDZ-201106, a sodium channel opener which was also identified as an inhibitor, is to raise the intracellular $Na^+$ concentration. One of the compounds that resulted in increased luciferase signals (phenamil) is an amiloride analogue that acts as a sodium channel inhibitor. These opposing effects, by compounds that have contrasting effects on sodium channels, indicate that influenza virus is sensitive to changes in intracellular ion concentrations and that this may be a way of modulating influenza virus replication. In support of this, it has been reported that influenza virus can inhibit these amiloride-sensitive sodium channels in the respiratory epithelium (Chen et al., 2004; Kunzelmann et al., 2000).

Amongst the group of inhibitory compounds were also found several protein kinase C (PKC) inhibitors, the strongest of which was rottlerin.

TABLE 2

Functional categories of the hit compounds with inhibitory activity.

| Functional category | Number of compounds | % of total |
|---|---|---|
| DNA interfering compounds | 20 | 23.8 |
| Antibiotics/Antifungals/Antiparasitics | 18 | 21.4 |
| Kinase inhibitors | 11 | 13.1 |
| Cardioactive glycosides | 7 | 8.3 |
| Cell redox metabolism interfering compounds | 4 | 4.8 |
| Other compounds | 24 | 28.5 |
| Total number of inhibitory compounds | 84 | 100 |

6.2.2 Inhibition of RNA Viruses by Sodium Potassium ATPase Pump Inhibitors

The Na$^+$/K$^+$/ATPase pump inhibitors, ouabain, lanatoside C, strophanthidin, and digoxin were identified as potential influenza virus inhibitors in the HTS. These cardioactive glycosides have used in the treatment of congestive heart failure and cardiac arrhythmia.

The ability of ouabain and lanatoside C to inhibit influenza virus replication was next examined. The $CC_{50}$ (concentration of 50% cytotoxicity) for ouabain and lanatoside C on A549 cells was determined to be 47 nM and 210 nM, respectively (data not shown) and for the viral replication assays a $CC_{20}$ was used for each compound. A549 cells were infected at an MOI of 1 with influenza A/WSN/33 virus in the presence of 20 nM ouabain or 78 nM lanatoside C and at 24 hours post infection the viral titers were found to be decreased by 99.1% with ouabain treatment and by 95.9% with lanatoside C treatment, compared to the untreated control (FIG. 2A). The effect of these compounds was next shown to extend to other RNA viruses. Both ouabain and lanatoside C significantly inhibited the replication of Newcastle disease virus (NDV) (FIG. 2B) and vesicular stomatitis virus (VSV) (FIGS. 2C and 2D). Therefore, these Na+/K+/ATPase pump inhibitors can inhibit multiple members of both RNA and DNA virus families. To address the possibility that the broad antiviral activity may be related to the induction of interferon, the effects of the compounds on influenza virus replication in Vero cells, which do not produce interferon, was examined. A similar level of inhibition as in A549 cells (data not shown) was observed, thereby suggesting that there is another mechanism shared among viruses targeted by these compounds.

6.2.3 Inhibition of Influenza A and B Virus Replication by a Sodium Channel Opener and a PKC Inhibitor The high-throughput assay revealed that the sodium channel opener, SDZ-201106, and the PKC inhibitor, rottlerin, are potential influenza virus inhibitors. To confirm the specificity of these compounds, the cytotoxicity profiles of the compounds were evaluated. A549 cells were seeded into 96-well plates and treated with increasing concentrations of SDZ-201106 or rottlerin for 24 hours before performing an MTS assay to determine cell viability. The $CC_{50}$ of SDZ-201106 was determined to be 29 μM and concentrations up to 12.5 μM were found to be non-toxic (FIG. 3A). The $CC_{50}$ of rottlerin was determined to be 18.2 μM and concentrations up to 1.28 μM did not decrease cell viability (FIG. 3B). All further experiments with rottlerin were performed using a maximum concentration of 1.25 μM. To determine the $IC_{50}$ (half maximal inhibitory concentration) for both inhibitors, A549 cells were infected for 24 hours with influenza A/WSN/33 virus at an MOI of 1 in the presence of increasing compound concentrations. Viral titers were determined by plaque assay. The $IC_{50}$ for SDZ-201106 was determined to be 4.1 μM (FIG. 3C). This results in a selective index (SI=$CC_{50}$/$IC_{50}$) of 7, which classifies this sodium channel opener as a weak inhibitor. The $IC_{50}$ for rottlerin was determined to be 465 nM (FIG. 3D). With an SI of 39, this PKC inhibitor is considered to be a moderate inhibitor. Table 3 below summarizes the $CC_{50}$, $IC_{50}$ and SI values for both inhibitors. Both compounds were then tested at their highest, non-toxic concentrations for their inhibitory activity against both influenza A/WSN/33 virus and influenza B/Yamagata/88 virus (FIG. 4). In the presence of 12.5 μM SDZ-201106 there is an 85% reduction in titers of influenza A/WSN/33 virus compared to the untreated control and the growth of influenza B/Yamagata/88 virus is reduced by 72%. Compared to the untreated controls, titers of influenza A/WSN/33 virus and influenza B/Yamagata/88 virus are significantly reduced by 93% and 80%, respectively, in the presence of 1.25 μM rottlerin.

TABLE 3

Potency of the inhibitors against influenza A virus in A549 cells

| | $CC_{50}$ [μM] [a] | $IC_{50}$ [μM] [b] | SI [$CC_{50}$/$IC_{50}$] [c] |
|---|---|---|---|
| SDZ-201106 | 29 | 4.1 | 7 |
| Rottlerin | 18.2 | 0.46 | 39 |

[a] $CC_{50}$—compound concentration of 50% cytotoxicity
[b] $IC_{50}$—compound concentration of 50% inhibition of viral replication
[c] SI—selective index 6.2.4 Enhancement of Influenza A and B Virus Replication by Sodium Channel Inhibitors and PKC Activators Identification of enhancers is preferably performed under multi-cycle replication conditions, because the HTS assay, which is performed with a high MOI, allows for the detection of strong enhancers. The effects of the PKC activators PMA and mezerein were evaluated, due to the link between PKC activity and sodium channel regulation and the fact that PKC inhibitors can downregulate influenza virus growth. For the sodium channel inhibitors, in addition to phenamil, which was identified in the screen as a potential enhancer, the effects of a related sodium channel inhibitor, dichlorobenzamil, were evaluated. A549 cells were infected with influenza A/WSN/33 virus at a low multiplicity in the presence of increasing concentrations of each compound in order to find the most effective concentration (data not shown). Multicycle growth assays for influenza A/WSN/33 virus were then performed in the presence of 400 nM 2',4'-dichlorobenzamil, 10 μM phenamil, 250 nM PMA or 250 nM mezerein (FIG. 5). The growth of influenza A/WSN/33 virus was greatly enhanced in the presence of the sodium channel inhibitors. Compared to the untreated control, the viral titer was increased 10$^3$ fold in the presence of 400 nM 2',4'-dichlorobenzamil and 16 fold in the presence of 10 μM phenamil at 48 hours post infection (FIG. 5A). In the presence of the PKC activators, the titers of influenza A/WSN/33 virus increased 17 fold with 250 nM mezerein and 12 fold with 250 nM PMA, compared to untreated cells at 48 hours post infection (FIG. 5B). The enhancing effects of these compounds on the replication of influenza B/Yamagata/88 virus were also examined (FIG. 6). In the presence of 400 nM 2',4'-dichlorobenzamil, the viral titer increased 4 fold at 48 hours post infection compared to untreated cells. With mezerein, the viral growth enhancement is seen much earlier with an 8 fold increase at 12 and 24 hours post infection. Therefore the growth of both influenza A and B viruses is enhanced by the addition of sodium channel inhibitors and PKC activators.

Although the HTS assay of this example was performed with a high multiplicity infection and therefore probably only strong enhancers could be detected, which is advantageous for, e.g., enhancing virus replication in vaccine manufacturing applications, the identification of enhancers could be optimized though the use of multi-cycle replication conditions. Furthermore, compounds with enhancing activity may be marked as false negatives if the concentration at which the screen is performed is cytotoxic. For example, PMA was not originally recognized in the screen as an enhancer because, most likely, the initial concentration of PMA used in the screen (~6 µM) was toxic.

Whether the growth-enhancing effects of these compounds could be observed with human isolates of influenza virus that have not been adapted to cell culture was also examined. For this purpose, the growth of influenza A/Moscow/10/99 and A/Wyoming/03/2003 viruses was compared in the absence and presence of mezerein and 2',4'-dichlorobenzamil. These viruses grew poorly in A549 cells but a significant increase in the maximum viral titers in the presence of mezerein and 2',4'-dichlorobenzamil compared to untreated cells was observed (FIGS. 7A and B). Thus, the ability of these compounds to boost virus replication is a property that extends to different influenza virus strains, which will be beneficial if used for production of influenza vaccines that change every year. For the current egg-grown vaccines, the seed strains for influenza A viruses are 6:2 reassortant viruses that contain the HA and NA genes of the vaccine virus in the background of influenza A/PR/8/34 virus. This is done to obtain high titers in eggs and to avoid the need to adapt each new virus strain.

The same strategy is used for the H5N1 influenza vaccine that has been approved by the FDA, with the addition that the multibasic cleavage site present in the HA (which is associated with high pathogenicity in chickens) has been removed (Subbarao et al., 2003; Treanor et al., 2006). The growth properties of this H5N1/PR8 vaccine virus in A549 cells that had been treated with 2',4'-dichlorobenzamil was examined and the titers were increased by ~20 fold compared to in untreated cells (FIG. 7C). A significant increase in viral titers in the presence of 2',4'-dichlorobenzamil and mezerein (11 fold and 15 fold, respectively) was also observed when influenza A/WSN/33 virus was grown in Vero cells, which is one of the approved cell lines for vaccine production (data not shown).

To address the question of whether there is a correlation between the viral inhibitory or enhancing activities of these compounds and their ability to induce or inhibit apoptosis, the activity of caspase-3, an indicator of apoptosis induction, was monitored. To mimic the condition of the cells at the time of infection, A549 cells were incubated with the compounds for 6 hours and staurosporin (5 µM) was used as a positive control to induce apoptosis. Phenamil (which enhances influenza virus growth) showed a very slight induction (1.3 fold) of apoptosis during this time period, whereas all the other compounds did not display any significant increases or decreases in fluorescence compared to the untreated cells, indicating the absence of pro-apoptotic or anti-apoptotic activity (data not shown).

The effects of 2',4'-dichlorobenzamil versus 3',4'-dichlorobenzamil for their ability to enhance influenza virus growth was compared (FIG. 8). Both compounds boost influenza virus replication above that obtained with the untreated control, but the change of a chloride from position 2 in the benzyl group to position 3 makes it 10 times less efficient. Therefore, it is useful to modulate the activities of drug candidates by making small changes to the structure of the compound.

6.2.5 Effect of Passaging Influenza Virus in the Presence of Inhibitors

Figure 9:
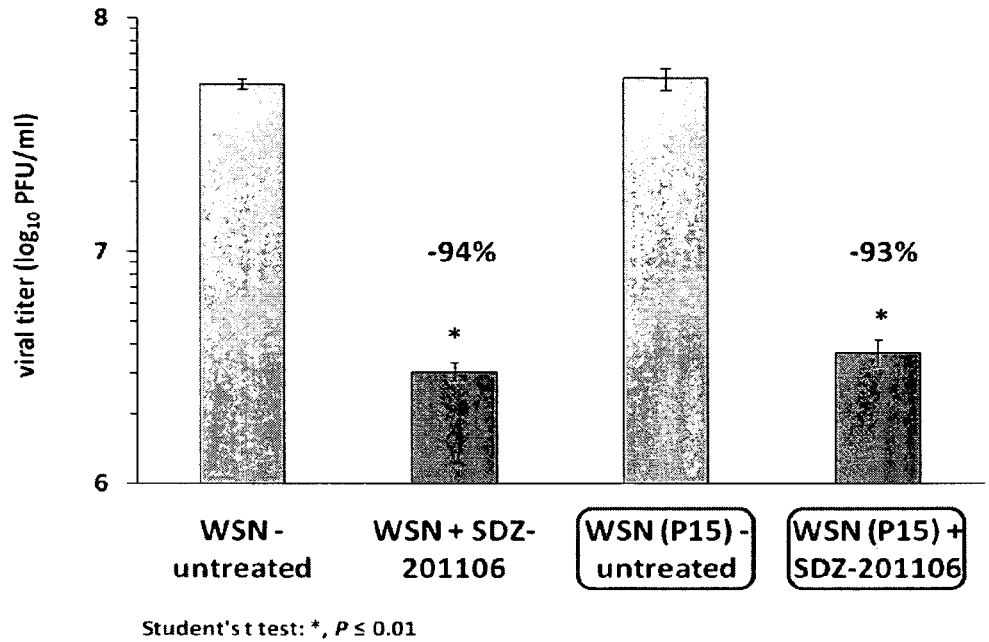
Figure 9:
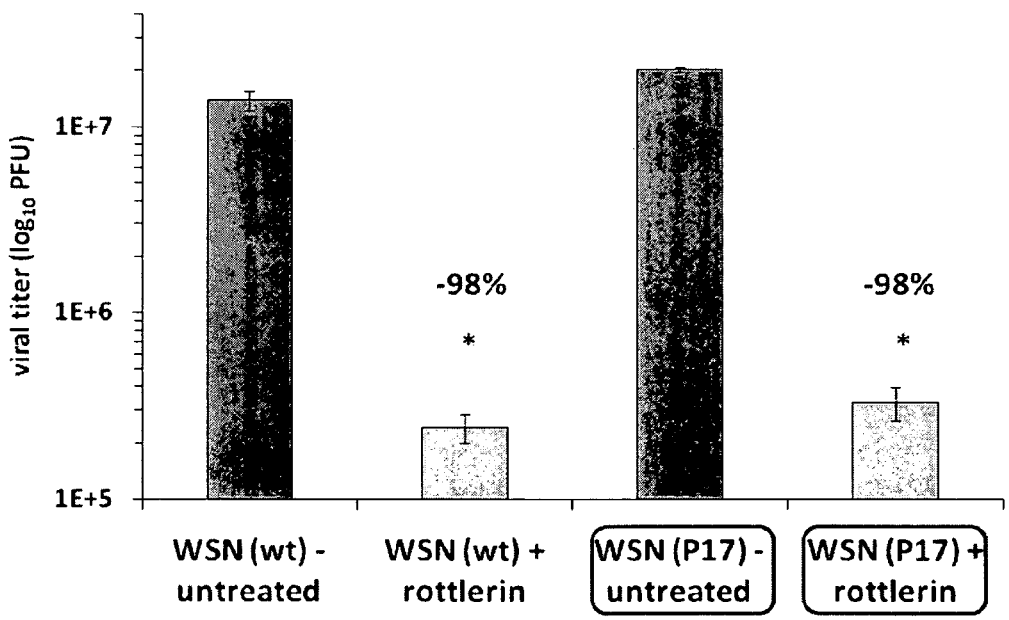

A549 cells were infected with influenza virus in the absence or presence of the inhibitors SDZ-201106 (used at 12.5 µM) or rottlerin (used at 1.25 µM). After 24 hours, the virus was collected. This virus was designated as passage 1 (P1) and was then used for a second round of infection and a 3rd, $4^{th}$, etc. After 15 passages in the absence or presence of SDZ-201106 or after 17 passages in the absence or presence of rottlerin, the susceptibility of the P15 or P17 viruses to the compounds was determined. The growth of the passaged viruses in the presence of compound was compared to that of unpassaged virus (titers were determined by plaque assay in MDCK cells). No difference between the susceptibility of the passaged viruses and unpassaged virus to either SDZ-201106 or rottlerin was observed, indicating that the virus had failed to develop resistance (FIGS. 9A and 9B, respectively).

6.3 DISCUSSION

An influenza pandemic caused by a virus of avian origin could not only have the potential to cause millions of deaths worldwide but could also affect the poultry industry which is crucial for the production of egg-derived vaccines. The primary concerns that need to be addressed in preparation for the next influenza epidemic or pandemic are the abilities of the manufacturers to produce enough doses of vaccine for the susceptible population and the availability of more antiviral compounds that are effective at preventing influenza virus infection. In the luciferase-based, high-throughput screen of 2640 compounds with known biological activity described in this example, 84 unique compounds with at least 70% reduction in luciferase activity and 4 compounds that increased luciferase activity at least 2 fold have been identified. The results of the experiments presented in this example support the rationale that compounds found to suppress influenza virus replication are potential anti-influenza virus drugs, whereas those that enhance influenza replication could be used as a tool to boost the growth of vaccine viruses in tissue culture. Moreover, because the biological targets of these compounds are known, it also provides clues as to which cellular pathways and components are crucial for influenza virus replication. In some respects, the use of antiviral drugs that target cellular proteins is an advantage over the current drugs that target viral proteins and against which resistance is far more likely to develop. Of particular interest was the finding that sodium channel inhibitors and a sodium channel opener had opposing effects on viral replication. By adding 2',4'-dichlorobenzamil, an amiloride-analogue that inhibits epithelial $Na^+$ channels (ENaC) and $Na^+/Ca^{+2}$ exchange channels (Kleyman and Cragoe, 1988), viral replication of influenza A/WSN/33 virus was enhanced $10^3$ fold. In direct contrast, using the sodium channel opener SDZ-201106 at non-toxic concentrations, the titers of influenza A/WSN/33 virus could be decreased by 85%. The effects of these compounds on influenza B virus replication were less dramatic (4 fold increase with 2',4'-dichlorobenzamil and 72% decrease with SDZ-201106), but the overall trend was similar, suggesting that the cellular pathways affected by these compounds are important for both influenza A and B viruses. The fact that influenza virus has been shown to inhibit amiloride-sensitive sodium channels upon infection (Chen et al., 2004; Kunzelmann et al., 2000) suggests that through doing so, the virus creates a cellular environment that is conducive to viral replication. It is therefore likely that the addition of chemical $Na^+$ channel inhibitors (such as phenamil or 2',4'-dichlorobenzamil) prior to infection creates pre-optimized conditions and thereby boosts virus replication.

Finally, it was shown that after 15 or 17 passages of influenza virus in the presence of the sodium channel opener SDZ-201106 or rottlerin, respectively, the emergence of resistant viruses was not observed. This indicates that resistance is less likely to develop if the inhibitory drug targets a cellular protein.

Without being bound by any theory, the data presented in this example indicate that an increase in the intracellular $Na^+$ concentration caused by opening the sodium channels leads to a decline in influenza virus titers, whereas a decreased intracellular $Na^+$ concentration caused by the inhibition of sodium channels can boost viral replication. Another possibility is that, because the different intracellular ion currents are tightly linked to one another, there may be a contribution of $Ca2^+$ to these effects, due to regulation of the $Na^+/Ca2^+$ exchange channel. Although many compounds can target more than one type of channel, several of the amiloride analogues have more potent activity against a specific channel. In this example, 2', 4'-dichlorobenzamil shows slightly stronger pro-viral activity than phenamil. A comparison of their reported potencies against ENaC or the $Na^+/Ca2^+$ exchange channel indicates that phenamil is more specific for ENaC while 2',4'-dichlorobenzamil is more specific for the $Na^+/Ca2^+$ exchange channel (Kleyman and Cragoe, 1988). Another amiloride analogue, 3',4'-dichlorobenzamil, is, compared with 2',4'-dichlorobenzamil, less effective at enhancing virus replication and has less potent activity against the $Na^+/Ca2^+$ exchange channel than 2',4'-dichlorobenzamil (Kleyman and Cragoe, 1988). Therefore, again without wishing to be bound by any theory of the inhibitors' mechanisms of action, it appears that the ability to enhance the growth of influenza virus correlates with the strength of inhibition of the $Na^+/Ca2^+$ exchange channel.

In contrast to findings presented herein, amiloride derivatives have been reported to inhibit the replication of several RNA viruses such as human immunodeficiency virus (HIV-1) (Ewart et al., 2004), human rhinovirus (Gazina et al., 2005), coxsackievirus (Harrison et al., 2008) and coronaviruses (Stevens et al., 2006). For HIV-1 (Ewart et al., 2002), coronaviruses, hepatitis C virus (Premkumar et al., 2004) and dengue virus (Premkumar et al., 2005). These compounds have been shown to act by inhibiting the formation of the viral ion channel. There is no evidence that the influenza virus M2 ion channel activity is adversely affected by amilorides and the results presented herein show that for influenza virus, these compounds have a pro-viral effect.

The data presented herein demonstrate that influenza replication is inhibited in the presence of a PKC inhibitor (rottlerin) but, conversely, is enhanced in the presence of a PKC activator (PMA or mezerein). Without being bound by any theory, it appears that there is a connection between the activation status of PKC and the transport of $Na^+$ and that influenza virus replication favors the presence of activated PKC and a low intracellular $Na^+$ concentration.

This example further demonstrates that the $Na^+/K^+/ATPase$ pump inhibitors, ouabain and lanatoside C, inhibit the replication of influenza virus, NDV and VSV, representatives of three different RNA virus families. This data indicates that these cardioactive glycosides have antiviral activity for negative-sense, single-stranded RNA viruses. Through the use of Vero cells, it has been determined that these compounds do not act by inducing interferon, as the same degree of virus inhibition was observed in these cells as seen in A549 cells. Another common feature shared by these viruses is that they all possess a lipid envelope, however data on ouabain-mediated inhibition of HSV-1 indicates that it acts at a post-entry stage of the viral life cycle (Dodson et al., 2007). The main function of the $Na^+/K^+/ATPase$ pump is to pump $Na^+$ out of the cell and $K^+$ into the cell to maintain the cell potential as a driving force for several membrane transport proteins (e.g. the $Na^+$-glucose symporter, the $Na^+$-amino acid symporter or the $Na^+$-hydrogen antiporter). This gradient is also important for the removal of $Ca^{2+}$ by the $Na^+/Ca^{+2}$ exchange channel. Thus, in the presence of an inhibitor such as ouabain, there is an increase in the intracellular $Na^+$ concentration as well as the $Ca^{2+}$ concentration and this is probably similar to the effects of a sodium channel opener such as SDZ-201106, which also inhibits influenza virus replication.

This example has shown that influenza viruses are sensitive to changes in intracellular ion concentrations and this may be a suitable target for novel antiviral drugs. Similarly, knowledge of these crucial factors that are required for optimal virus growth may be used to boost virus production. This technology could be used for the production of influenza virus vaccines which will most likely make the transition to in vitro culture systems in the near future. As a demonstration of this potential application, which would require activity for a wide range of influenza viruses, the enhancing compounds identified in the study were shown to boost the replication of different influenza A viruses, influenza B virus, and the FDA-approved H5N1 vaccine virus strain.

6.4 REFERENCES

The references listed in this section include those cited in this example.

Arora, D. J. and Gasse, N. (1998) Influenza virus hemagglutinin stimulates the protein kinase C activity of human polymorphonuclear leucocytes. Arch Virol 143(10), 2029-37.

Blair, W. S., Isaacson, J., Li, X., Cao, J., Peng, Q., Kong, G. F. and Patick, A. K., 2005. A novel HIV-1 antiviral high throughput screening approach for the discovery of HIV-1 inhibitors. Antiviral Res 65(2), 107-16

Booth, R. E. and Stockand, J. D. (2003) Targeted degradation of ENaC in response to PKC activation of the ERK1/2 cascade. Am J Physiol Renal Physiol 284(5), F938-47.

Bright, R. A., Shay, D. K., Shu, B., Cox, N. J. and Klimov, A. I. (2006) Adamantane resistance among influenza A viruses isolated early during the 2005-2006 influenza season in the United States. JAMA 295(8), 891-4.

Chen, G. W., Yang, C. C., Tsao, K. C., Huang, C. G., Lee, L. A., Yang, W. Z., Huang, Y. L., Lin, T. Y. and Shih, S. R. (2004) Influenza A virus PB1-F2 gene in recent Taiwanese isolates. Emerg Infect Dis 10(4), 630-6.

Cheung, C. L., Rayner, J. M., Smith, G. J., Wang, P., Naipospos, T. S., Zhang, J., Yuen, K. Y., Webster, R. G., Peiris, J. S., Guan, Y. and Chen, H. (2006) Distribution of amantadine-resistant H5N1 avian influenza variants in Asia. J Infect Dis 193(12), 1626-9.

Claas, E. C., Osterhaus, A. D., van Beek, R., De Jong, J. C., Rimmelzwaan, G. F., Senne, D. A., Krauss, S., Shortridge, K. F. and Webster, R. G. (1998) Human influenza A H5N1 virus related to a highly pathogenic avian influenza virus. Lancet 351(9101), 472-7.

Chu, J. J. and Yang, P. L., 2007. c-Src protein kinase inhibitors block assembly and maturation of dengue virus. Proc Natl Acad Sci USA 104(9), 3520-5.

Deng, L., Dai, P., Ciro, A., Smee, D. F., Djaballah, H. and Shuman, S. (2007) Identification of novel antipoxviral agents: mitoxantrone inhibits vaccinia virus replication by blocking virion assembly. J Virol 81(24), 13392-402.

Dodson, A. W., Taylor, T. J., Knipe, D. M. and Coen, D. M. (2007) Inhibitors of the sodium potassium ATPase that impair herpes simplex virus replication identified via a chemical screening approach. Virology 366(2), 340-8.

Ewart, G. D., Mills, K., Cox, G. B. and Gage, P. W. (2002) Amiloride derivatives block ion channel activity and enhancement of virus-like particle budding caused by HIV-1 protein Vpu. Eur Biophys J 31(1), 26-35.

Ewart, G. D., Nasr, N., Naif, H., Cox, G. B., Cunningham, A. L. and Gage, P. W. (2004) Potential new anti-human immunodeficiency virus type 1 compounds depress virus replication in cultured human macrophages. Antimicrob Agents Chemother 48(6), 2325-30.

Fodor, E., Devenish, L., Engelhardt, O. G., Palese, P., Brownlee, G. G. and Garcia-Sastre, A. (1999) Rescue of influenza A virus from recombinant DNA. J Virol 73(11), 9679-82.

Garman, E. and Layer, G. (2004) Controlling influenza by inhibiting the virus's neuraminidase. Curr Drug Targets 5(2), 119-36.

Gazina, E. V., Harrison, D. N., Jefferies, M., Tan, H., Williams, D., Anderson, D. A. and Petrou, S. (2005) Ion transport blockers inhibit human rhinovirus 2 release. Antiviral Res 67(2), 98-106.

Ghosh, R. N., DeBiasio, R., Hudson, C. C., Ramer, E. R., Cowan, C. L. and Oakley, R. H., 2005. Quantitative cell-based high-content screening for vasopressin receptor agonists using transfluor technology. J Biomol Screen 10(5), 476-84.

Harrison, D. N., Gazina, E. V., Purcell, D. F., Anderson, D. A. and Petrou, S. (2008) Amiloride derivatives inhibit coxsackievirus B3 RNA replication. J Virol 82(3), 1465-73.

Hellebrekers, D. M., Griffioen, A. W. and van Engeland, M. (2007) Dual targeting of epigenetic therapy in cancer. Biochim Biophys Acta 1775(1), 76-91.

Kleyman, T. R. and Cragoe, E. J., Jr. (1988) The mechanism of action of amiloride. Semin Nephrol 8(3), 242-8.

Kunzelmann, K., Beesley, A. H., King, N. J., Karupiah, G., Young, J. A. and Cook, D. I. (2000) Influenza virus inhibits amiloride-sensitive Na+ channels in respiratory epithelia. Proc Natl Acad Sci USA 97(18), 10282-7.

Kurokawa, M., Ochiai, H., Nakajima, K. and Niwayama, S. (1990) Inhibitory effect of protein kinase C inhibitor on the replication of influenza type A virus. J Gen Virol 71 (Pt 9), 2149-55.

Le, Q. M., Kiso, M., Someya, K., Sakai, Y. T., Nguyen, T. H., Nguyen, K. H., Pham, N. D., Ngyen, H. H., Yamada, S., Muramoto, Y., Horimoto, T., Takada, A., Goto, H., Suzuki, T., Suzuki, Y. and Kawaoka, Y. (2005) Avian flu: isolation of drug-resistant H5N1 virus. Nature 437(7062), 1108.

Matrosovich, M., Matrosovich, T., Garten, W. and Klenk, H. D., 2006. New low-viscosity overlay medium for viral plaque assays. Virol J 3, 63.

Nagai, Y., Maeno, K., Iinuma, M., Yoshida, T. and Matsumoto, T. (1972) Inhibition of virus growth by ouabain: effect of ouabain on the growth of HVJ in chick embryo cells. J Virol 9(2), 234-43.

Neumann, G. and Hobom, G., 1995. Mutational analysis of influenza virus promoter elements in vivo. J Gen Virol 76 (Pt 7), 1709-17.

Noah, J. W., Severson, W., Noah, D. L., Rasmussen, L., White, E. L. and Jonsson, C. B., 2007. A cell-based luminescence assay is effective for high-throughput screening of potential influenza antivirals. Antiviral Res 73(1), 50-9.

Oxford, J. S., Manuguerra, C., Kistner, O., Linde, A., Kunze, M., Lange, W., Schweiger, B., Spala, G., Rebelo de Andrade, H., Perez Brena, P. R., Beytout, J., Brydak, L., Caraffa de Stefano, D., Hungnes, O., Kyncl, J., Montomoli, E., Gil de Miguel, A., Vranckx, R. and Osterhaus, A. (2005) A new European perspective of influenza pandemic planning with a particular focus on the role of mammalian cell culture vaccines. Vaccine 23(46-47), 5440-9.

Palese, P. and Shaw, M. L. (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689.

Paltauf-Doburzynska, J., Frieden, M., Spitaler, M. and Graier, W. F. (2000) Histamine-induced Ca2+ oscillations in a human endothelial cell line depend on transmembrane ion flux, ryanodine receptors and endoplasmic reticulum Ca2+-ATPase. J Physiol 524 Pt 3, 701-13.

Pinto, L. H. and Lamb, R. A. (1995) Understanding the mechanism of action of the anti-influenza virus drug amantadine. Trends Microbiol 3(7), 271.

Pleschka, S., Jaskunas, R., Engelhardt, 0.0., Zurcher, T., Palese, P. and Garcia-Sastre, A. (1996) A plasmid-based reverse genetics system for influenza A virus. J Virol 70(6), 4188-92.

Premkumar, A., Horan, C. R. and Gage, P. W. (2005) Dengue virus M protein C-terminal peptide (DVM-C) forms ion channels. J Membr Biol 204(1), 33-8.

Premkumar, A., Wilson, L., Ewart, G. D. and Gage, P. W. (2004) Cation-selective ion channels formed by p7 of hepatitis C virus are blocked by hexamethylene amiloride. FEBS Lett 557(1-3), 99-103.

Romanova, J., Katinger, D., Ferko, B., Vcelar, B., Sereinig, S., Kuznetsov, O., Stukova, M., Erofeeva, M., Kiselev, O., Katinger, H. and Egorov, A. (2004) Live cold-adapted influenza A vaccine produced in Vero cell line. Virus Res 103(1-2), 187-93.

Root, C. N., Wills, E. G., McNair, L. L. and Whittaker, G. R. (2000) Entry of influenza viruses into cells is inhibited by a highly specific protein kinase C inhibitor. J Gen Virol 81(Pt 11), 2697-705.

Rott, O., Charreire, J., Semichon, M., Bismuth, G. and Cash, E. (1995) B cell superstimulatory influenza virus (H2-subtype) induces B cell proliferation by a PKC-activating, Ca(2+)-independent mechanism. J Immunol 154(5), 2092-103.

Senne, D. A., Panigrahy, B., Kawaoka, Y., Pearson, J. E., Suss, J., Lipkind, M., Kida, H. and Webster, R. G., 1996. Survey of the hemagglutinin (HA) cleavage site sequence of H5 and H7 avian influenza viruses: amino acid sequence at the HA cleavage site as a marker of pathogenicity potential. Avian Dis 40(2), 425-37.

Severson, W. E., Shindo, N., Sosa, M., Fletcher, T., 3rd, White, E. L., Ananthan, S, and Jonsson, C. B., 2007. Development and validation of a high-throughput screen for inhibitors of SARS CoV and its application in screening of a 100,000-compound library. J Biomol Screen 12(1), 33-40.

Sieczkarski, S. B., Brown, H. A. and Whittaker, G. R. (2003) Role of protein kinase C betaII in influenza virus entry via late endosomes. J Virol 77(1), 460-9.

Stockand, J. D., Bao, H. F., Schenck, J., Malik, B., Middleton, P., Schlanger, L. E. and Eaton, D. C. (2000) Differential effects of protein kinase C on the levels of epithelial Na+ channel subunit proteins. J Biol Chem 275(33), 25760-5.

Subbarao, K., Chen, H., Swayne, D., Mingay, L., Fodor, E., Brownlee, G., Xu, X., Lu, X., Katz, J., Cox, N. and Matsuoka, Y. (2003) Evaluation of a genetically modified reassortant H5N1 influenza A virus vaccine candidate generated by plasmid-based reverse genetics. Virology 305(1), 192-200.

Takada, A., Kuboki, N., Okazaki, K., Ninomiya, A., Tanaka, H., Ozaki, H., Itamura, S., Nishimura, H., Enami, M., Tashiro, M., Shortridge, K. F. and Kida, H. (1999) Avirulent Avian influenza virus as a vaccine strain against a potential human pandemic. J Virol 73(10), 8303-7.

Tomita, Y. and Kuwata, T. (1978) Suppression of murine leukaemia virus production by ouabain and interferon in mouse cells. J Gen Virol 38(2), 223-30.

Treanor, J. J., Campbell, J. D., Zangwill, K. M., Rowe, T. and Wolff, M. (2006) Safety and immunogenicity of an inactivated subvirion influenza A (H5N1) vaccine. N Engl J Med 354(13), 1343-51.

Tree, J. A., Richardson, C., Fooks, A. R., Clegg, J. C. and Looby, D. (2001) Comparison of large-scale mammalian cell culture systems with egg culture for the production of influenza virus A vaccine strains. Vaccine 19(25-26), 3444-50.

Wharton, S. A., Belshe, R. B., Skehel, J. J. and Hay, A. J. (1994) Role of virion M2 protein in influenza virus uncoating: specific reduction in the rate of membrane fusion between virus and liposomes by amantadine. J Gen Virol 75 (Pt 4), 945-8.

Wilson L., Gage P. and Ewart G (2006) Hexamethtlene amiloride blocks E protein ion channels and inhibits coronavirus replication. Virology 353(2):294-306.

World Health Organization (2003) Influenza: Overview; http://www.who.int/mediacentre/factsheets/fs211/en/; March 2003.

World Health Organization (2008) Influenza A (H1N1) virus resistance to oseltamivir; http://www.who.int/csr/disease/influenza/h1n1_table/en/index.html; Feb. 28, 2008.

Yamagata, T., Yamagata, Y., Masse, C., Tessier, M. C., Brochiero, E., Dagenais, A. and Berthiaume, Y. (2005) Modulation of Na+ transport and epithelial sodium channel expression by protein kinase C in rat alveolar epithelial cells. Can J Physiol Pharmacol 83(11), 977-87.

Zhang, J. H., Chung, T. D. and Oldenburg, K. R. (1999) A Simple Statistical Parameter for Use in Evaluation and Validation of High Throughput Screening Assays. Biomol Screen 4(2), 67-73.

Zuck, P., Murray, E. M., Stec, E., Grobler, J. A., Simon, A. J., Strulovici, B., Inglese, J., Flores, O. A. and Ferrer, M., 2004. A cell-based beta-lactamase reporter gene assay for the identification of inhibitors of hepatitis C virus replication. Anal Biochem 334(2), 344-55.

7. EXAMPLE

Identification of Inhibitors in a Screen of Approximately 73,000 Compounds

In a second HTS assay, using the same Materials and Methods as used in Section 6.1 supra (unless otherwise indicated), approximately 73,000 compounds were screened of which 61,174 were compounds of commercial library plates with unknown biological properties. The commercial libraries screened included Asinex 1—(12,378 compounds screened out of 12,378) by ASINEX, Winston-Salem, N.C.; ChemDiv 3—(1,760 compounds screened out of 16,544) by ChemDiv Inc., San Diego, Calif.; ChemDiv 4—(14,677 compounds screened out of 14,677) by ChemDiv Inc., San Diego, Calif.; ChemDiv 5—(1,249 compounds screened out of 1,249) by ChemDiv Inc., San Diego, Calif.; ENAMINE 2—(352 compounds screened out of 26,576) by ENAMINE Ltd., Kiev, Ukraine; Maybridge 4—(4,576 compounds screened out of 4,576) by Maybridge Ltd., Trevillet, UK; Maybridge 5—(3,212 compounds screened out of 3,212) by Maybridge Ltd., Trevillet, UK; ActiMol TimTec 1—(8,517 compounds screened out of 8,517) by TimTec Inc., Newark, Del.; ChemBridge 3—(10,560 compounds screened out of 10,560) by ChemBridge Corp., San Diego, Calif.; LifeChemicals 1—(3,893 compounds screened out of 3,893) by LifeChemicals Inc., Burlington, Canada. 146 compounds met the criteria of at least a 90% reduction in luminescence signal and were defined as a hit.

The cytotoxicity of each compound was determined for a 24 hour period in A549 cells in a concentration range from 0.1-300 μM. For further tissue culture studies, the individual compound concentration never exceeded the $CC_{10}$. The $CC_{10}$ is the concentration of 10% cytotoxicity (in other words the concentration with 90% cell viability compared to untreated cells).

To validate the inhibitory potential of the compounds, A549 cells were pretreated for 4-6 hours at increasing concentrations of each compound. Subsequently, the cells were infected with influenza A virus at an MOI of 1 and incubated for another 20-24 hours. The compounds were present throughout the course of infection. Viral replication and release of viral particles was determined by hemagglutination assays using 0.5% chicken red blood cells. A compound was followed up further if it reduced viral replication by at least 2 wells of HA, which equals about a 75% reduction in viral titers. Two additional criteria used were that the $IC_{50}$ (half maximal inhibitory concentration) was below 10 μM and that the SI, the selective index ($CC_{50}/IC_{50}$), was above 10. 18 compounds able to inhibit influenza A virus replication in A549 cells at non-cytotoxic concentrations were identified.

All compounds were further tested for their effect on the other negative-sense, single-stranded RNA viruses influenza B virus, NDV and VSV (FIGS. 13 and 14). The cytotoxicity of the compounds was also determined in different cell lines (MDCK, MEF, 293T, HUH 7.5, Detroit, HTBE) and their effect on viral replication was determined.

The following assays were performed to narrow down the site of action for each compound. In particular, entry assay studies were performed. RNA replication and transcription were also measured, using influenza virus mini-genome assays as described in Pleschka et al., 1996, "A plasmid-based reverse genetics system for influenza A virus," *J. Virol.* 70:4188-92. Such mini-genome assays enable the identification of inhibitors of the viral polymerase or inhibitors of cellular proteins that are involved in viral replication, translation and RNA trafficking. The compounds were also tested in kinetic studies in which they were added prior to and post infection at different times and virus growth was assayed using a plaque assay.

Three lead compounds which display high potency in inhibiting viral replication in A549 cells and primary lung cells, such as human tracheobronchial epithelial (HTBE) cells, were identified. As shown in Table 4 below, the ability of three compounds, 2-(5-(2,3-dimethyl-1H-indol-5-yl)-1,3,4-oxadiazol-2-ylthio)-1-(pyrrolidin-1-yl)ethanone ("A3"); 4-(4-bromophenyl)-N-methyl-N-(tetrahydro-1,1-dioxido-3-thienyl)-2-thiazolamine ("A35"); and 9-(benzo[d][1,3]dioxol-5-yl)-4-hydroxy-6,7-dimethoxynaphtho[2,3-c]furan-1(3H)-one ("C2") to inhibit influenza viruses A and B ("FluA" and "FluB," respectively) was tested in different cell types. Cells were infected at an MOI of 1 and viral titers were determined 24 hours post-infection.

TABLE 4

| compound | CC$_{50}$ | IC$_{50}$ | SI | inhibition of FluA | inhibition of FluB |
|---|---|---|---|---|---|
| A3 | 268 μM (A549) | 0.54 μM (A549)* | 496 (A549) | 97% (A549)* | 94% (A549)* |
|  | >100 μM (MDCK) | 0.82 μM (MDCK)** | >122 (MDCK) | ~99.6% (MDCK)** |  |
|  | >100 μM (MEF) | 3.6 μM (MEF)** | >28 (MEF) | ~91.2% (MEF)** |  |
|  | 108 μM (HTBE) | 0.042 μM (HTBE)* | 2571 (HTBE) | 99.99% (HTBE)* |  |
| A35 | 110 μM (A549) | 2.1 μM (A549)* | 53 (A549) | 99.988% (A549)* | 63% (A549)* |
|  | 26.8 μM (MDCK) | 3.91 μM (MDCK)** | 7 (MDCK) | ~75% (MDCK)** |  |
|  | 96.6 μM (MEF) | 2.64 μM (MEF)** | 37 (MEF) | ~99.6% (MEF)** |  |
|  | 29.3 μM (293T) | 6.2 μM (293T)** | 5 (293T) | ~50% (293T)** |  |
|  | 79.7 μM (Detroit) | 2.07 μM (Detroit)** | 39 (Detroit) | ~95.6% (Detroit)** |  |
|  | 59 μM (HUH7.5) | 3.97 μM (HUH7.5)** | 15 (HUH7.5) | ~98.4% (HUH7.5)** |  |
|  | 119 μM (HTBE) | 1.98 μM (HTBE)* | 60 (HTBE) | 99.98% (HTBE)* |  |
| C2 | 131 μM (A549) | 1.6 μM (A549)** | 82 (A549) | 94.7% (A549)* | 63% (A549)* |
|  | 0.67 μM (MDCK) | 0.15 μM (MDCK)** | 4 (MDCK) | ~87.5% (MDCK)** |  |
|  | 4.85 μM (MEF) | 0.34 μM (MEF)** | 14 (MEF) | ~96% (MEF)** |  |
|  | 20.6 μM (HTBE) | 0.059 μM (HTBE)* | 349 (HTBE) | 99.96% (HTBE)* |  |

*viral titer determined by plaque assay
**viral titer determined by HA assay

Figure 10:
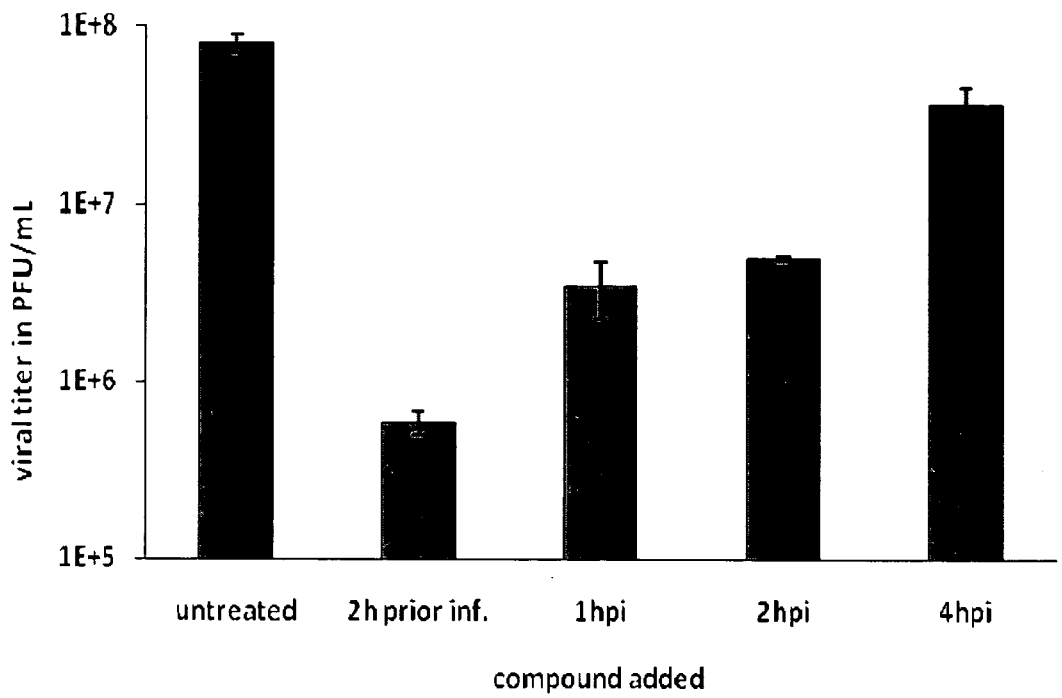
Figure 13:
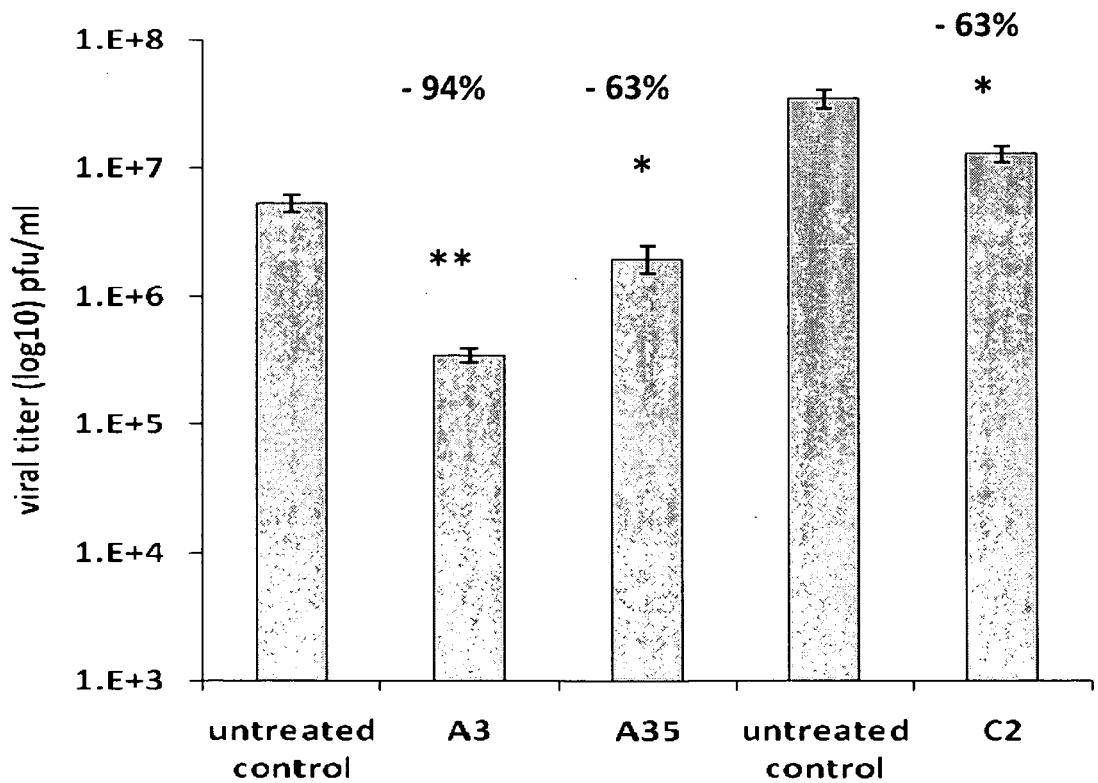
Figure 15:
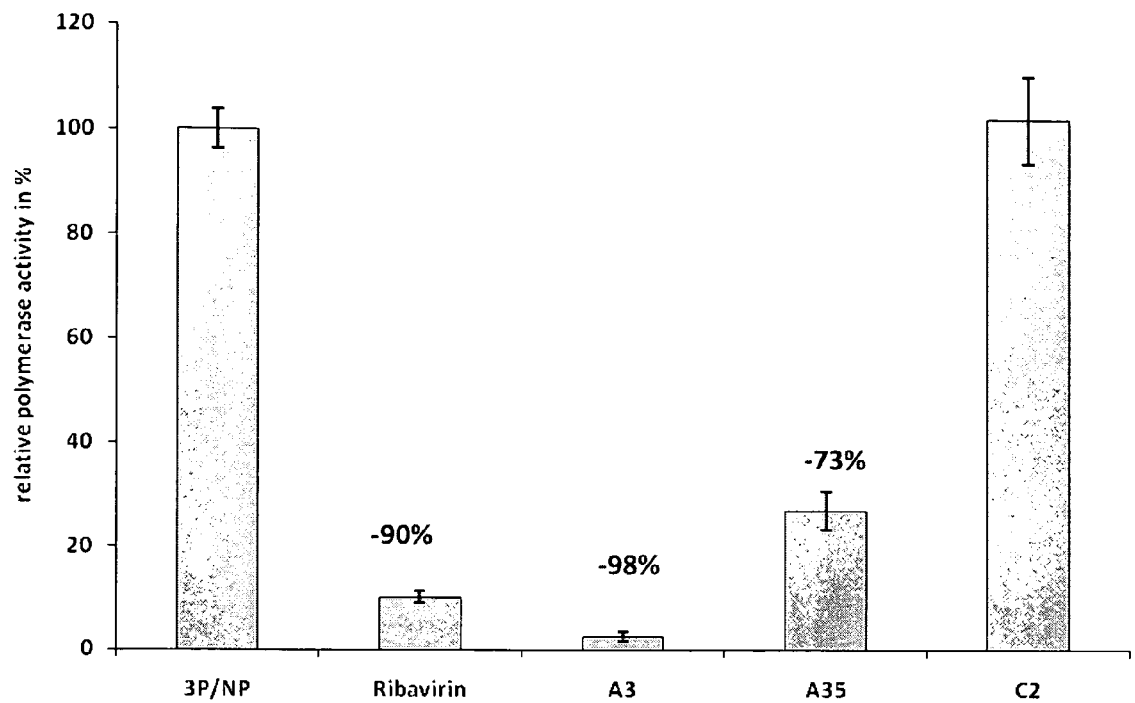
Figure 16:
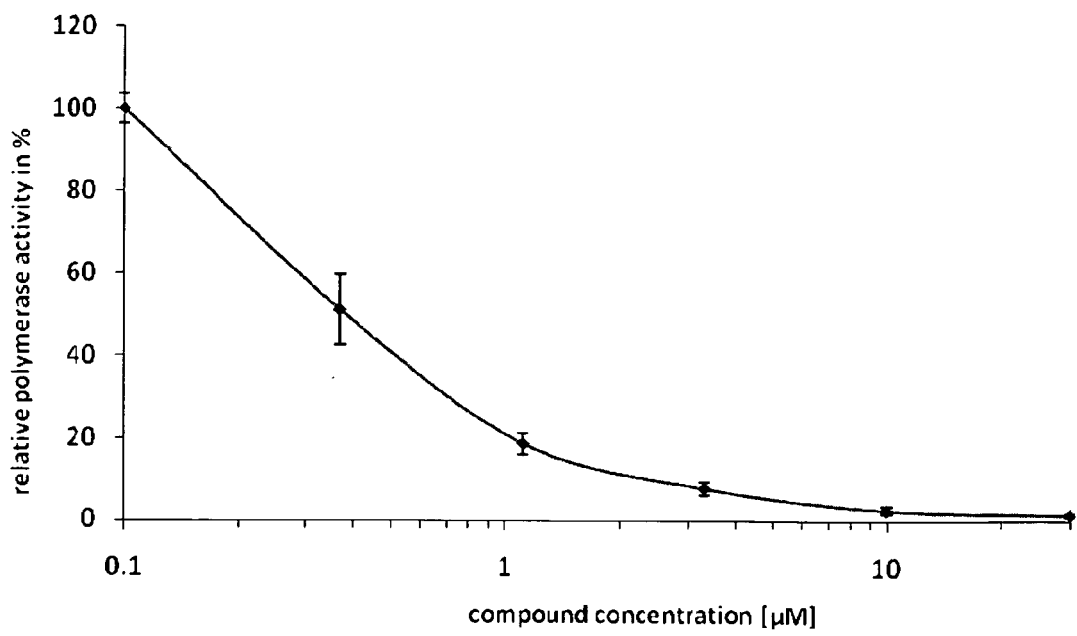

Lead compound A3 was identified in a screen of the Asinex 1 source library (12,378 compounds; ASINEX, Winston-Salem, N.C., USA). In kinetic studies using A549 cells infected with influenza strain WSN (MOI=1), A3 was found to inhibit viral replication by approximately 2 logs when added 2 hours prior to infection and by 1 log when added up to 2 hours post infection (FIG. 10). In studies using an influenza virus mini-genome reporter construct, A3 was found to inhibit viral RNA polymerase activity by up to 99% at 10 μM, whereas ribavirin, a known polymerase inhibitor, was found to inhibit only 90% of the activity at 100 μM (FIG. 15). A3 was tested in dose response experiments and at all A3 concentrations (0.4-30 μM), the overall host cell replication machinery was not affected as monitored by the expression of a renilla luciferase control plasmid (FIG. 16). In viral entry assays performed, A3 did not inhibit viral entry. A3, at a concentration of 10 μM, was found to inhibit influenza A viruses and influenza B viruses similarly (see, e.g., Table 4). As shown in FIG. 13, A3 inhibited the growth of influenza B virus in A549 cells by about 1.5 logs (FIG. 13). The IC$_{50}$ of A3 in HTBE cells was found to be 42 nM and the SI was measured as 2571.

Figure 11:
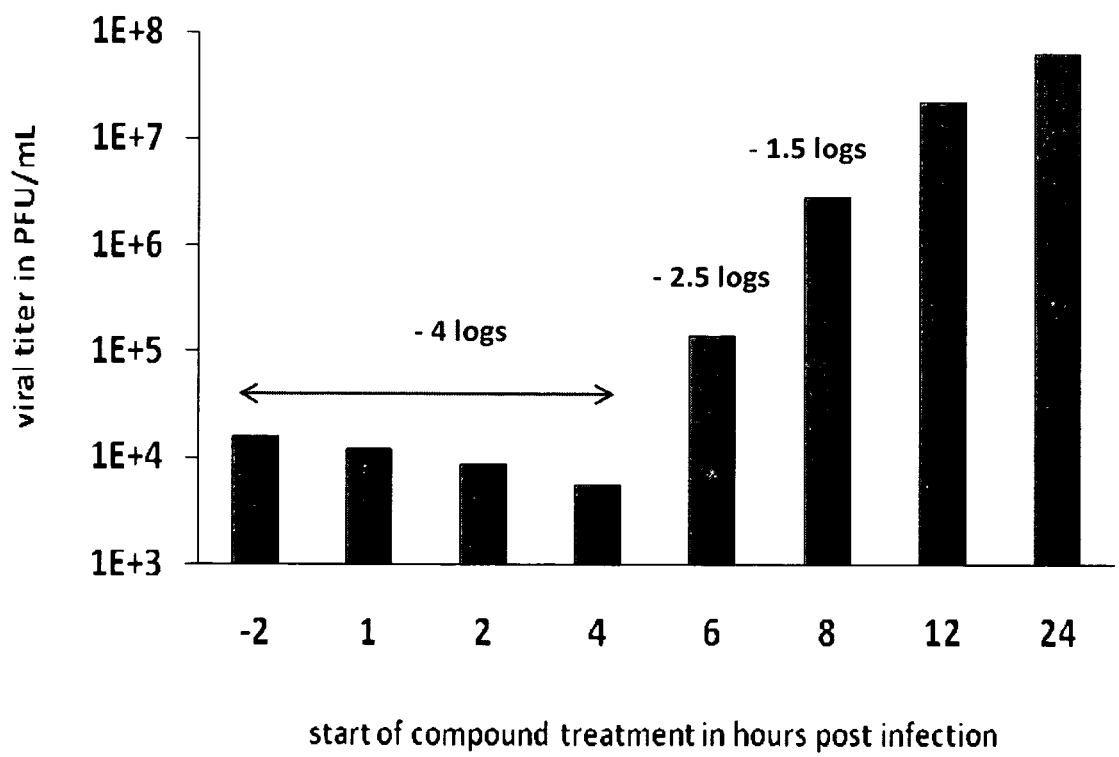
Figure 14:
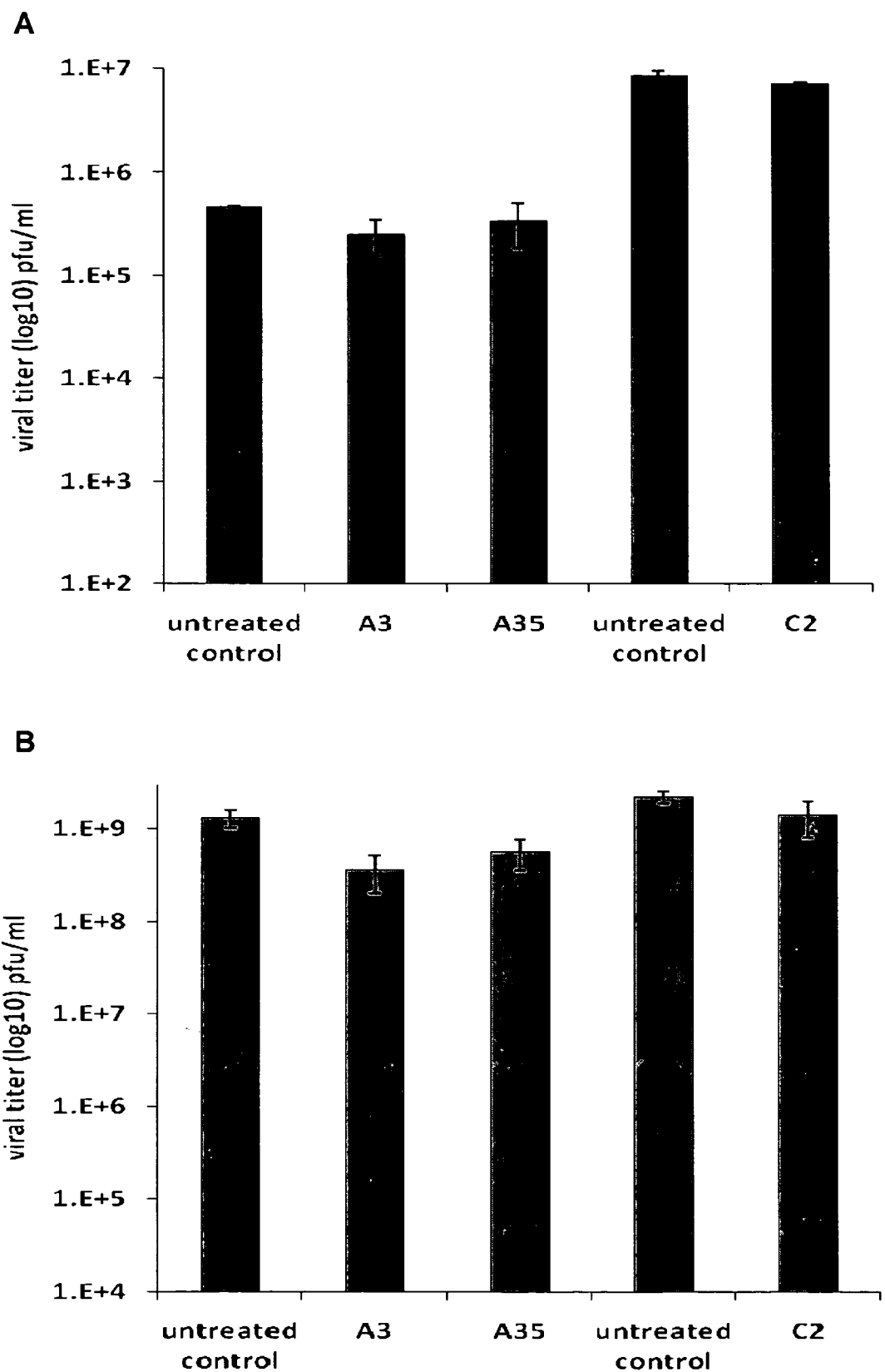

Lead compound A35 was identified in a screen of the Asinex 1 source library (12,378 compounds; ASINEX, Winston-Salem, N.C., USA). A35 was found to be highly potent in a variety of different cell lines with an inhibition of influenza virus replication of up to 4 logs (in A549 and HTBE cells). In viral entry assay studies performed, A35 did not affect the entry step of influenza virus. In kinetic studies using A549 cells infected with influenza strain WSN (MOI=1), when A35 was added prior to infection or even up to 4 hours post infection, inhibition of viral replication was unaltered (4 logs; FIG. 11). Thus, A35 is likely to target a crucial step in the viral life cycle. Without being bound by any theory, these experiments suggest that A35 affects RNA trafficking and/or packaging. At a concentration of 11.2 μM, A35 inhibits influenza A virus with high specificity, but has a less significant inhibition of influenza B virus (FIG. 13), NDV (FIG. 14A) and VSV (FIG. 14B).

Figure 12:
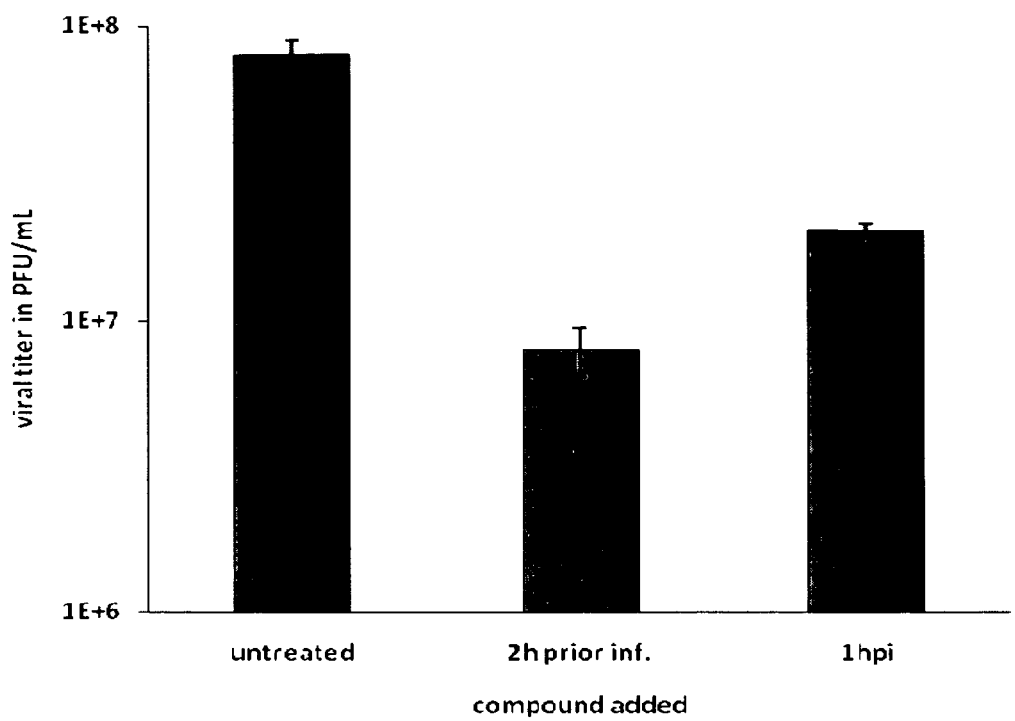

Lead compound C2 was identified in a screen of the ChemDiv 4 source library (14,677 compounds; ChemDiv Inc., San Diego, Calif., USA). C2, at a concentration of 2 μM, was found to potently inhibit influenza virus replication in HTBE cells by up to 3.5 logs. The IC$_{50}$ of C2 in HTBE cells was determined to be 59 nM and the SI was found to be approximately 350. In kinetic studies, addition of C2 to infected cells at 1 hour post infection did not affect the course of infection (FIG. 12). In viral entry assay studies performed, it was found that entry of influenza virus and VSV, which both enter the cell by endocytosis, was inhibited in the presence of C2 whereas entry of the retrovirus MLV, which fuses with the plasma membrane, was unaffected. Therefore, without being bound by any theory, it appears that C2 targets an early step in the viral life cycle, the endocytosis of the viral particles.

For two compounds, A3 and A35, a number of their derivatives were tested for cytotoxicity and inhibition of viral replication in order to identify related structures that can be used as inhibitors of viral replication. The results from these experiments are shown in Table 5 below.

TABLE 5

| Name | Structure | CC$_{10}$ (A549) | CC$_{50}$ (A549) | IC$_{50}$ (A549) | SI (A549) | Inhibition of FluA |
|---|---|---|---|---|---|---|
| A35 | (structure) | 11.2 μM | 110 μM | 2.1 μM* | 53 | 99.99%* |

TABLE 5-continued

| Name | Structure | CC$_{10}$ (A549) | CC$_{50}$ (A549) | IC$_{50}$ (A549) | SI (A549) | Inhibition of FluA |
|---|---|---|---|---|---|---|
| A35-1 | 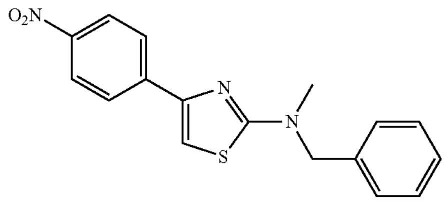 [SMILES: CN(Cc1ccccc1)c1nc(-c2ccc([N+](=O)[O-])cc2)cs1] | 10.8 μM | 201 μM | 3.24 μM | 62 | ~75% |
| A35-2 | 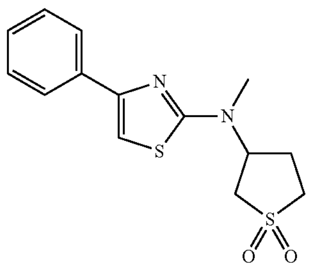 [SMILES: CN(c1nc(-c2ccccc2)cs1)C1CCS(=O)(=O)C1] | 12.2 μM | 148 μM | n/a | n/a | none** |
| A35-3 | 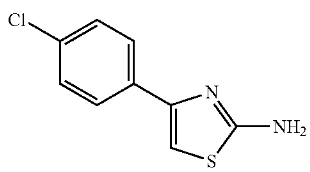 [SMILES: Nc1nc(-c2ccc(Cl)cc2)cs1] | 11.4 μM | 164.8 μM | n/a | n/a | none** |
| A35-4 | 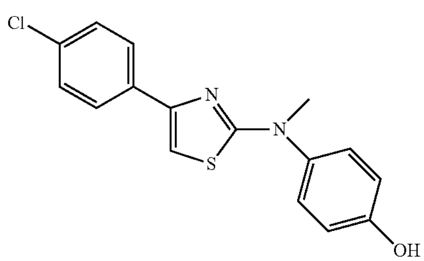 [SMILES: CN(c1ccc(O)cc1)c1nc(-c2ccc(Cl)cc2)cs1] | 6 μM | 30 μM | 6 μM | 5 | ~50% |
| A35-5 | 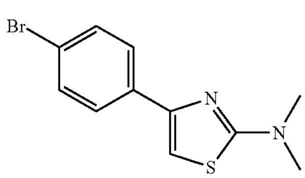 | 17.8 μM | 242.4 μM | 12.3 μM | 20 | ~65% |
| A3 | 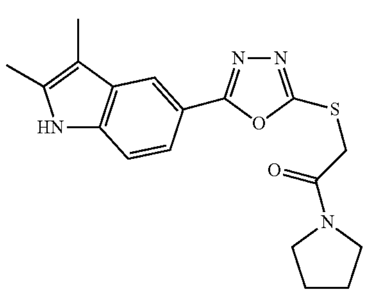 [SMILES: Cc1[nH]c2ccc(-c3nnc(SCC(=O)N4CCCC4)o3)cc2c1C] | 38 μM | 268 μM | 0.54 μM* | 496 | 99.2%* |

TABLE 5-continued
| Name | Structure | CC$_{10}$ (A549) | CC$_{50}$ (A549) | IC$_{50}$ (A549) | SI (A549) | Inhibition of FluA |
|---|---|---|---|---|---|---|
| A3-1 | 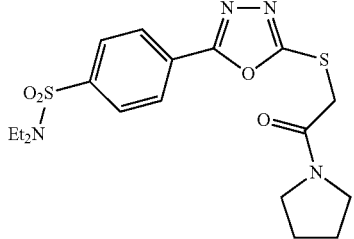 | 17.3 μM | 316 μM | n/a | n/a | ~29%** |
| A3-2 | 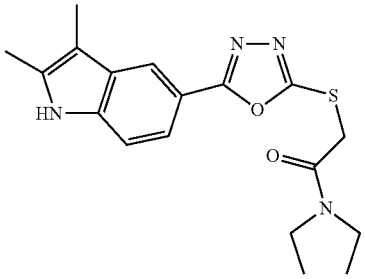 [SMILES: CCN(CC)C(=O)CSc1nnc(-c2ccc3[nH]c(C)c(C)c3c2)o1] | 29 μM | 198.5 μM | 1.2 μM | >165 | ~97% |
| A3-3 | 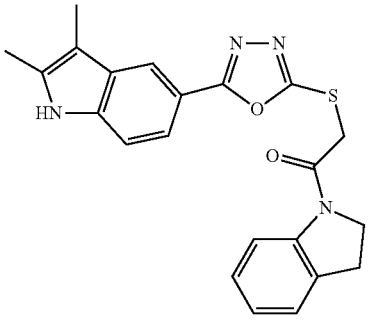 [SMILES: Cc1[nH]c2ccc(-c3nnc(SCC(=O)N4CCc5ccccc54)o3)cc2c1C] | 8.5 μM | 65 μM | 8.5 μM | 8 | ~50% |
| A3-4 | 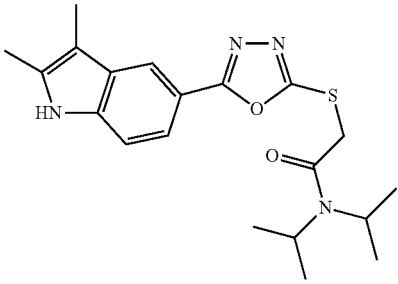 [SMILES: Cc1[nH]c2ccc(-c3nnc(SCC(=O)N(C(C)C)C(C)C)o3)cc2c1C] | 10.7 μM | 17.7 μM | 1.65 μM | 11 | ~87.5% |
| A3-5 | 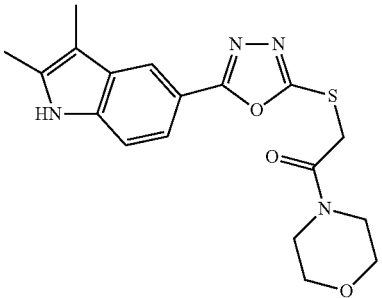 [SMILES: Cc1[nH]c2ccc(-c3nnc(SCC(=O)N4CCOCC4)o3)cc2c1C] | 10.2 μM | 256.8 μM | 0.5 μM | 514 | ~97% |

TABLE 5-continued

| Name | Structure | CC$_{10}$ (A549) | CC$_{50}$ (A549) | IC$_{50}$ (A549) | SI (A549) | Inhibition of FluA |
|---|---|---|---|---|---|---|
| A3-6 | 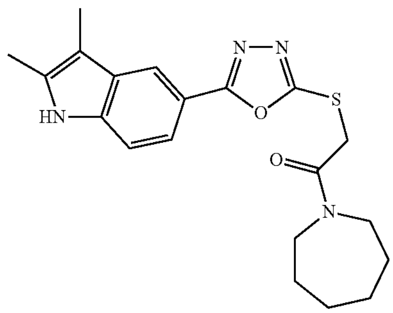 [SMILES: Cc1[nH]c2ccc(-c3nnc(SCC(=O)N4CCCCCC4)o3)cc2c1C] | 18.2 μM | 179 μM | 0.98 μM | 180 | ~87.5% |
| A3-7 | 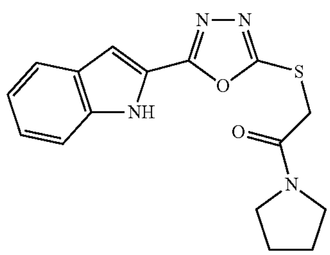 [SMILES: O=C(CSc1nnc(-c2cc3ccccc3[nH]2)o1)N1CCCC1] | 15.2 μM | 134 μM | n/a | n/a | ~29%** |
| A3-8 | 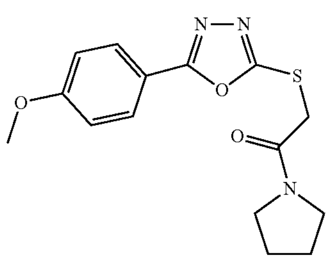 [SMILES: COc1ccc(-c2nnc(SCC(=O)N3CCCC3)o2)cc1] | 11.8 μM | 249.8 μM | n/a | n/a | none** |
| A3-9 | 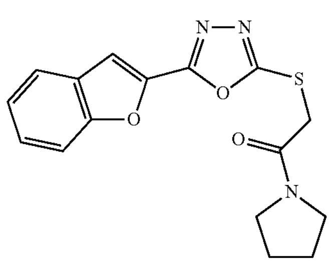 [SMILES: O=C(CSc1nnc(-c2cc3ccccc3o2)o1)N1CCCC1] | 10.9 μM | 197 μM | n/a | n/a | ~29%** |
| A3-11 | 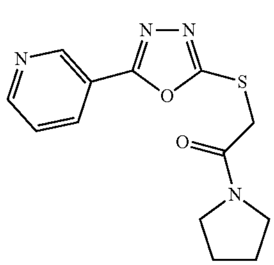 [SMILES: O=C(CSc1nnc(-c2cccnc2)o1)N1CCCC1] | 32.6 μM | 248.8 μM | n/a | n/a | none** |

TABLE 5-continued

| Name | Structure | CC$_{10}$ (A549) | CC$_{50}$ (A549) | IC$_{50}$ (A549) | SI (A549) | Inhibition of FluA |
|---|---|---|---|---|---|---|
| A3-12 | 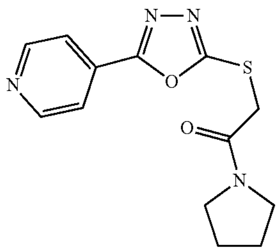 [SMILES: O=C(CSc1nnc(-c2ccncc2)o1)N1CCCC1] | 11.5 μM | 186 μM | n/a | n/a | ~29%** |

*-determined by plaque assay;
**-determined by HA assay;
n/a-not available

8. EQUIVALENTS

Those skilled in the art will recognize or be able to ascertain, using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed:

1. A method of inhibiting replication of a negative-sense, single-stranded RNA virus in an animal subject, or preventing, treating or managing an influenza virus infection comprising administering to an animal subject in need thereof an effective amount of a compound with the formula ("A3-G")

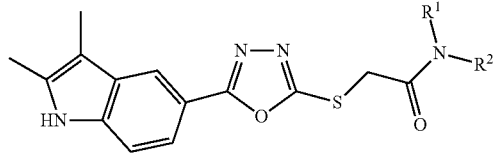

or a pharmaceutically acceptable salt, hydrate, solvate, prodrug or stereoisomer thereof, wherein:
 R$^1$ and R$^2$ are at each occurrence independently a C$_1$-C$_8$ alkyl group; or
 R$^1$ and R$^2$, together with the nitrogen atom R$^1$ and R$^2$ are bound to, form a 3 to 8 membered saturated heterocyclic ring.

2. The method of claim 1, wherein the compound is 2-(5-(2,3-dimethyl-1H-indol-5-yl)-1,3,4-oxadiazol-2-ylthio)-1-(pyrrolidin-1-yl)ethanone ("A3"); 2-(5-(2,3-dimethyl-1H-indol-5-yl-1,3,4-oxadiazol-2-ylthio-N,N-diethylacetamide ("A3-2"); 2-(5-(2,3-dimethyl-1H-indol-5-yl)-1,3,4-oxadiazol-2-ylthio)-1-(indolin-1-yl)ethanone ("A3-3"); 2-(5-(2,3-dimethyl-1H-indol-5-yl)-1,3,4-oxadiazol-2-ylthio)-N,N-diisopropylacetamide ("A3-4"); 2-(5-(2,3-dimethyl-1H-indol-5-yl)-1,3,4-oxadiazol-2-ylthio)-1-morpholinoethanone ("A3-5"); or 1-(azepan-1-yl)-2-(5-(2,3-dimethyl-1H-indol-5-yl)-1,3,4-oxadiazol-2-ylthio)ethanone ("A3-6").

3. The method of claim 2, wherein the compound is 2-(5-(2,3-dimethyl-1H-indol-5-yl)-1,3,4-oxadiazol-2-ylthio)-1-(pyrrolidin-1-yl)ethanone ("A3").

4. The method of claim 1, wherein the negative-sense, single-stranded RNA virus is a paramyxovirus or orthomyxovirus.

5. The method of claim 1, wherein the negative-sense, single-stranded RNA virus is influenza virus, NDV, VSV, or Sendai virus.

6. The method of claim 1, wherein the animal subject is a human subject.

* * * * *

UNITED STATES PATENT AND TRADEMARK OFFICE
CERTIFICATE OF CORRECTION

PATENT NO. : 8,629,283 B2  
APPLICATION NO. : 12/921077  
DATED : January 14, 2014  
INVENTOR(S) : Shaw et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,629,283 B2 | Page 1 of 1 |
| APPLICATION NO. | : 12/921077 | |
| DATED | : January 14, 2014 | |
| INVENTOR(S) | : Shaw et al. | |

It is certified that error appears in the above-identified patent and that said Letters Patent is hereby corrected as shown below:

In the Specification

Column 1, Line 10:

DELETE:

"This invention was made with government support under Grant Nos. AI057158, AI074539 and HHSN266200700010C awarded by the National Institutes of Health. The government has certain rights to the invention."

ADD:

--This invention was made with government support under U54 AI057158, U01 AI074539 and HHSN266200700010C awarded by the National Institutes of Health. The government has certain rights to the invention.--

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*